US011432870B2

(12) United States Patent
Schorr et al.

(10) Patent No.: US 11,432,870 B2
(45) Date of Patent: Sep. 6, 2022

(54) COOLED RF PROBES

(71) Applicant: Avent, Inc., Alpharetta, GA (US)

(72) Inventors: Phillip A. Schorr, Cumming, GA (US);
Eric A. Schepis, Alpharetta, GA (US);
Skyler Canute, Manlius, NY (US);
Joseph DiPietro, Ponte Vedra, FL (US);
Sara Kebede, New Orleans, LA (US);
Tyler West Crone, Atlanta, GA (US);
Elliot Blake Bourgeois, Huntsville, AL (US)

(73) Assignee: Avent, Inc., Alpharetta, GA (US)

( * ) Notice: Subject to any disclaimer, the term of this patent is extended or adjusted under 35 U.S.C. 154(b) by 432 days.

(21) Appl. No.: 16/338,600

(22) PCT Filed: Oct. 3, 2017

(86) PCT No.: PCT/US2017/054834
§ 371 (c)(1),
(2) Date: Apr. 1, 2019

(87) PCT Pub. No.: WO2018/067496
PCT Pub. Date: Apr. 12, 2018

(65) Prior Publication Data
US 2019/0239941 A1  Aug. 8, 2019

Related U.S. Application Data

(60) Provisional application No. 62/403,876, filed on Oct. 4, 2016.

(51) Int. Cl.
*A61B 18/14* (2006.01)
*A61F 7/10* (2006.01)
*A61B 18/00* (2006.01)

(52) U.S. Cl.
CPC .......... *A61B 18/148* (2013.01); *A61F 7/106* (2013.01); *A61B 2018/00005* (2013.01);
(Continued)

(58) Field of Classification Search
CPC ...... A61F 2007/0054; A61F 2007/0093; A61F 2007/0094; A61F 2007/0095;
(Continued)

(56) References Cited

U.S. PATENT DOCUMENTS 4,290,435 A   9/1981   Waggott
5,139,496 A   8/1992   Hed
(Continued)

FOREIGN PATENT DOCUMENTS

JP   2005-137792   6/2005
JP   2010-012145   1/2010
(Continued)

OTHER PUBLICATIONS

Office Action dated Jun. 29, 2021, issued in related JP application No. 2019-515268, 4 pages.
(Continued)

*Primary Examiner* — Tigist S Demie
(74) *Attorney, Agent, or Firm* — Meunier Carlin & Curfman LLC

(57) ABSTRACT

An electrosurgical device is provided that includes a probe extending in a longitudinal direction and having a proximal region and a distal region. An inner diameter of the probe defines a lumen. The probe has an electrically insulated portion extending from the proximal region to the distal region and an electrically exposed conductive portion located at the distal region. The electrically exposed conductive portion delivers radiofrequency energy to an area of tissue adjacent the distal region. The device also includes a heat transfer system for removing thermal energy from the
(Continued)

area of tissue that is in thermal contact with the area of tissue. The heat transfer system removes from about 0.1 Watts to about 50 Watts of energy from the tissue. In addition, the heat transfer system can sufficiently draw heat away from the tissue without the use of a peristaltic pump for circulating a liquid inside the lumen.

30 Claims, 23 Drawing Sheets

(52) U.S. Cl.
CPC .............. *A61B 2018/0044* (2013.01); *A61B 2018/00047* (2013.01); *A61B 2018/00791* (2013.01); *A61B 2018/00815* (2013.01); *A61B 2018/00821* (2013.01); *A61B 2018/00875* (2013.01)

(58) Field of Classification Search
CPC ...... A61F 2007/0096; A61F 2007/0295; A61F 2007/0298; A61F 7/0053; A61F 7/0085; A61F 7/0097; A61F 7/08; A61G 2210/70; A61G 2210/90; A61G 7/05
See application file for complete search history.

(56) References Cited

U.S. PATENT DOCUMENTS

| | | |
|---|---|---|
| 5,190,539 A | 3/1993 | Fletcher et al. |
| 5,342,357 A | 8/1994 | Nardella |
| 5,431,168 A | 7/1995 | Webster, Jr. |
| 5,462,521 A | 10/1995 | Brucker et al. |
| 5,520,684 A | 5/1996 | Imran |
| 5,584,872 A | 12/1996 | LaFontaine et al. |
| 5,688,267 A | 11/1997 | Panescu et al. |
| 5,697,927 A | 12/1997 | Imran |
| 5,735,846 A | 4/1998 | Panescu et al. |
| 5,735,847 A | 4/1998 | Gough et al. |
| 5,779,715 A | 7/1998 | Tn |
| 5,782,760 A | 7/1998 | Schaer |
| 5,782,900 A | 7/1998 | de la Rama et al. |
| 5,785,706 A | 7/1998 | Bednarek |
| 5,792,140 A | 8/1998 | Tu et al. |
| 5,800,379 A | 9/1998 | Edwards |
| 5,800,428 A | 9/1998 | Nelson et al. |
| 5,800,432 A | 9/1998 | Swanson |
| 5,800,482 A | 9/1998 | Pomeranz et al. |
| 5,810,804 A | 9/1998 | Gough et al. |
| 5,843,021 A | 12/1998 | Edwards et al. |
| 5,843,152 A | 12/1998 | Tu et al. |
| 5,893,885 A | 4/1999 | Webster. , Jr. |
| 5,913,854 A | 6/1999 | Maguire et al. |
| 5,916,213 A | 6/1999 | Haissaguerre et al. |
| 5,951,546 A | 9/1999 | Lorentzen |
| 5,980,515 A | 11/1999 | Tu |
| 5,997,532 A | 12/1999 | McLaughlin et al. |
| 5,997,534 A | 12/1999 | Tu et al. |
| 6,002,968 A | 12/1999 | Edwards |
| 6,010,500 A | 1/2000 | Sherman et al. |
| 6,013,076 A | 1/2000 | Goble et al. |
| 6,014,579 A | 1/2000 | Pomeranz et al. |
| 6,030,379 A | 2/2000 | Panescu et al. |
| 6,033,403 A | 3/2000 | Tu et al. |
| 6,045,549 A | 4/2000 | Smethers et al. |
| 6,050,994 A | 4/2000 | Sherman |
| 6,053,912 A | 4/2000 | Panescu et al. |
| 6,056,744 A | 5/2000 | Edwards |
| 6,056,745 A | 5/2000 | Panescu et al. |
| 6,059,780 A | 5/2000 | Gough et al. |
| 6,090,105 A | 7/2000 | Zepeda et al. |
| 6,099,524 A | 8/2000 | Lipson et al. |
| 6,120,476 A | 9/2000 | Fung et al. |
| 6,120,500 A | 9/2000 | Bednarek et al. |
| 6,171,275 B1 | 1/2001 | Webster, Jr. |
| 6,171,305 B1 | 1/2001 | Sherman |
| 6,179,803 B1 | 1/2001 | Edwards et al. |
| 6,197,023 B1 | 3/2001 | Muntermann |
| 6,210,355 B1 | 4/2001 | Edwards et al. |
| 6,210,406 B1 | 4/2001 | Webster |
| 6,228,081 B1 | 5/2001 | Goble |
| 6,235,021 B1 | 5/2001 | Sieben |
| 6,241,666 B1 | 6/2001 | Pomeranz et al. |
| 6,254,598 B1 | 7/2001 | Edwards et al. |
| 6,280,441 B1 | 8/2001 | Ryan |
| 6,287,305 B1 | 9/2001 | Heim et al. |
| 6,322,560 B1 | 11/2001 | Garbagnati et al. |
| 6,332,881 B1 | 12/2001 | Carner et al. |
| 6,371,955 B1 | 4/2002 | Fuimaono et al. |
| 6,448,678 B1 | 9/2002 | Simpson |
| 6,458,123 B1 | 10/2002 | Brucker et al. |
| 6,475,214 B1 | 11/2002 | Moaddeb |
| 6,500,175 B1 | 12/2002 | Gough et al. |
| 6,514,251 B1 | 2/2003 | Ni et al. |
| 6,517,534 B1 | 2/2003 | McGovern et al. |
| 6,527,769 B2 | 3/2003 | Langberg et al. |
| 6,530,922 B2 | 3/2003 | Cosman et al. |
| 6,542,766 B2 | 4/2003 | Hall et al. |
| 6,544,264 B2 | 4/2003 | Levine et al. |
| 6,558,381 B2 | 5/2003 | Ingle et al. |
| 6,558,382 B2 | 5/2003 | Jahns et al. |
| 6,569,162 B2 | 5/2003 | He |
| 6,584,360 B2 | 6/2003 | Francischelli et al. |
| 6,592,580 B1 | 7/2003 | Stockert |
| 6,605,087 B2 | 8/2003 | Swartz et al. |
| 6,611,699 B2 | 8/2003 | Messing |
| 6,616,657 B2 | 9/2003 | Simpson et al. |
| 6,622,731 B2 | 9/2003 | Daniel et al. |
| 6,662,034 B2 | 12/2003 | Segner et al. |
| 6,662,054 B2 | 12/2003 | Kreindel et al. |
| 6,671,561 B1 | 12/2003 | Moaddeb |
| 6,673,070 B2 | 1/2004 | Edwards et al. |
| 6,712,814 B2 | 3/2004 | Edwards et al. |
| 6,770,070 B1 | 8/2004 | Balbierz |
| 6,780,184 B2 | 8/2004 | Tanrisever |
| 6,811,544 B2 | 11/2004 | Schaer |
| 6,814,731 B2 | 11/2004 | Swanson |
| 6,814,732 B2 | 11/2004 | Scbaer |
| 6,814,733 B2 | 11/2004 | Schwartz et al. |
| 6,821,275 B2 | 11/2004 | Truckai et al. |
| 6,840,937 B2 | 1/2005 | Van Wyk |
| 6,840,954 B2 | 1/2005 | Dietz et al. |
| 6,852,110 B2 | 2/2005 | Roy et al. |
| 6,881,214 B2 | 4/2005 | Cosman et al. |
| 6,918,903 B2 | 7/2005 | Bass |
| 6,918,907 B2 | 7/2005 | Kelly et al. |
| 6,952,615 B2 | 10/2005 | Satake |
| 6,955,675 B2 | 10/2005 | Jain |
| 6,974,450 B2 | 12/2005 | Weber et al. |
| 6,974,456 B2 | 12/2005 | Edwards |
| 6,979,330 B2 | 12/2005 | Kelly et al. |
| 6,986,769 B2 | 1/2006 | Nelson et al. |
| 7,022,121 B2 | 4/2006 | Stern et al. |
| 7,041,100 B2 | 5/2006 | Kreindel |
| 7,074,218 B2 | 7/2006 | Washington et al. |
| 7,087,051 B2 | 8/2006 | Bourne et al. |
| 7,112,198 B2 | 9/2006 | Satake |
| 7,115,123 B2 | 10/2006 | Knowlton et al. |
| 7,125,407 B2 | 10/2006 | Edwards et al. |
| 7,141,049 B2 | 11/2006 | Stern et al. |
| 7,156,843 B2 | 1/2007 | Skarda |
| 7,160,296 B2 | 1/2007 | Pearson et al. |
| 7,211,106 B2 | 5/2007 | Dobak, III et al. |
| 7,229,436 B2 | 6/2007 | Stern et al. |
| 7,238,184 B2 | 7/2007 | Megerman et al. |
| 7,255,696 B2 | 8/2007 | Goble et al. |
| 7,264,619 B2 | 9/2007 | Venturelli |
| 7,267,674 B2 | 9/2007 | Brucker et al. |
| 7,267,675 B2 | 9/2007 | Stern et al. |
| 7,276,061 B2 | 10/2007 | Schaer et al. |
| 7,282,049 B2 | 10/2007 | Orszulak et al. |
| 7,282,051 B2 | 10/2007 | Rioux et al. |
| 7,326,204 B2 | 2/2008 | Paul et al. |
| 7,371,233 B2 | 5/2008 | Swanson et al. |

(56) References Cited

U.S. PATENT DOCUMENTS

| | | |
|---|---|---|
| 7,416,552 B2 | 8/2008 | Paul et al. |
| 7,422,586 B2 | 9/2008 | Morris et al. |
| 7,438,714 B2 | 10/2008 | Phan |
| 7,452,358 B2 | 11/2008 | Stern et al. |
| 7,473,251 B2 | 1/2009 | Knowlton et al. |
| 7,481,809 B2 | 1/2009 | Stern et al. |
| 7,553,309 B2 | 6/2009 | Buysse et al. |
| 7,569,052 B2 | 8/2009 | Phan et al. |
| 7,585,296 B2 | 9/2009 | Edwards et al. |
| 7,591,816 B2 | 9/2009 | Wang et al. |
| 7,628,788 B2 | 12/2009 | Datta |
| 7,648,500 B2 | 1/2010 | Edwards et al. |
| 7,662,152 B2 | 2/2010 | Sharareh et al. |
| 7,670,336 B2 | 3/2010 | Young et al. |
| 7,684,865 B2 | 3/2010 | Aldrich et al. |
| 7,686,802 B2 | 3/2010 | Stevens-Wright |
| 7,815,635 B2 | 10/2010 | Wittkampf et al. |
| 7,819,860 B2 | 10/2010 | Wittenberger et al. |
| 7,819,866 B2 | 10/2010 | Bednarek |
| 7,824,406 B2 | 11/2010 | Wang et al. |
| 7,850,685 B2 | 12/2010 | Kunis et al. |
| 7,857,809 B2 | 12/2010 | Drysen |
| 7,879,030 B2 | 2/2011 | Paul et al. |
| 7,879,031 B2 | 2/2011 | Peterson |
| 7,883,508 B2 | 2/2011 | Thao et al. |
| 7,914,528 B2 | 3/2011 | Wang et al. |
| 7,918,851 B2 | 4/2011 | Webster, Jr. et al. |
| 7,925,341 B2 | 4/2011 | Fuimaono |
| 7,938,828 B2 | 5/2011 | Koblish |
| 7,947,039 B2 | 5/2011 | Sartor |
| 7,951,143 B2 | 5/2011 | Wang |
| 7,955,326 B2 | 6/2011 | Paul et al. |
| 7,976,537 B2 | 7/2011 | Lieber et al. |
| 7,998,139 B2 | 8/2011 | Rossetto et al. |
| 7,998,182 B2 | 8/2011 | Dobak, III et al. |
| 8,002,462 B2 | 8/2011 | Podhajsky et al. |
| 8,034,050 B2 | 10/2011 | Sharareh et al. |
| 8,043,978 B2 | 10/2011 | Miyazaki et al. |
| 8,052,684 B2 | 11/2011 | Wang et al. |
| 8,073,551 B2 | 12/2011 | McCann et al. |
| 8,088,127 B2 | 1/2012 | Mayse et al. |
| 8,092,449 B2 | 1/2012 | Desinger et al. |
| 8,118,809 B2 | 2/2012 | Paul et al. |
| 8,123,742 B2 | 2/2012 | Berger |
| 8,135,475 B2 | 3/2012 | Kreindel et al. |
| 8,182,433 B2 | 5/2012 | Leo et al. |
| 8,188,435 B2 | 5/2012 | Podhajsky et al. |
| 8,192,427 B2 | 6/2012 | Buysse |
| 8,206,380 B2 | 6/2012 | Lenihan et al. |
| 8,216,218 B2 | 7/2012 | Burns et al. |
| 8,216,219 B2 | 7/2012 | Desinger et al. |
| 8,221,410 B2 | 7/2012 | Knowlton et al. |
| 8,226,648 B2 | 7/2012 | Paul et al. |
| 8,235,986 B2 | 8/2012 | Kulesa et al. |
| 8,262,653 B2 | 9/2012 | Plaza |
| 8,267,930 B2 | 9/2012 | Ma et al. |
| 8,290,582 B2 | 10/2012 | Lin et al. |
| 8,292,881 B2 | 10/2012 | Brannan et al. |
| 8,295,902 B2 | 10/2012 | Salaheih et al. |
| 8,303,584 B2 | 11/2012 | Burdio Pinilla et al. |
| 8,328,800 B2 | 12/2012 | Brannan |
| 8,333,762 B2 | 12/2012 | Mest et al. |
| 8,343,145 B2 | 1/2013 | Brannan |
| 8,348,937 B2 | 1/2013 | Wang et al. |
| 8,353,907 B2 | 1/2013 | Winkler et al. |
| 8,394,087 B2 | 3/2013 | Willyard et al. |
| 8,409,188 B2 | 4/2013 | Kim et al. |
| 8,414,579 B2 | 4/2013 | Kim et al. |
| 8,414,580 B2 | 4/2013 | Rioux et al. |
| 8,435,236 B2 | 5/2013 | Mizrahi et al. |
| 8,439,907 B2 | 5/2013 | Auth et al. |
| 8,449,537 B2 | 5/2013 | Cao et al. |
| 8,454,595 B2 | 6/2013 | Edwards et al. |
| 8,460,285 B2 | 6/2013 | Wang et al. |
| 8,475,449 B2 | 7/2013 | Werneth et al. |
| 8,500,730 B2 | 8/2013 | Lee et al. |
| 8,504,132 B2 | 8/2013 | Friedman et al. |
| 8,517,999 B2 | 8/2013 | Pappone et al. |
| 8,518,032 B2 | 8/2013 | Edwards et al. |
| 8,556,889 B2 | 10/2013 | Brannan |
| 8,568,398 B2 | 10/2013 | Brannan |
| 8,608,739 B2 | 12/2013 | Sartor et al. |
| 8,628,520 B2 | 1/2014 | Sharareh et al. |
| 8,632,533 B2 | 1/2014 | Greeley et al. |
| 8,632,564 B2 | 1/2014 | Cunningham |
| 8,641,704 B2 | 2/2014 | Werneth et al. |
| 8,641,710 B2 | 2/2014 | Doty et al. |
| 8,652,127 B2 | 2/2014 | Prakash et al. |
| 8,652,129 B2 | 2/2014 | Wu et al. |
| 8,672,938 B2 | 3/2014 | Buysse et al. |
| 8,685,017 B2 | 4/2014 | Stern et al. |
| 8,690,870 B2 | 4/2014 | Wang et al. |
| 8,702,693 B2 | 4/2014 | Subramaniam et al. |
| 8,709,004 B2 | 4/2014 | Ferreira et al. |
| 8,728,068 B2 | 5/2014 | Nye et al. |
| 8,728,075 B2 | 5/2014 | Wu et al. |
| 8,734,442 B2 | 5/2014 | Cao et al. |
| 8,764,742 B2 | 7/2014 | Pappone et al. |
| 8,764,744 B2 | 7/2014 | Brannan |
| 8,777,857 B2 | 7/2014 | Sliwa et al. |
| 8,784,401 B2 | 7/2014 | Cambier et al. |
| 8,788,060 B2 | 7/2014 | Nebrigic et al. |
| 8,795,270 B2 | 8/2014 | Drake |
| 8,795,272 B2 | 8/2014 | Rioux et al. |
| 8,795,304 B2 | 8/2014 | Pippo Svendsen et al. |
| 8,801,701 B2 | 8/2014 | Chopra et al. |
| 8,801,706 B2 | 8/2014 | Rothstein et al. |
| 8,814,852 B2 | 8/2014 | Ma et al. |
| 8,814,856 B2 | 8/2014 | Elmouelhi et al. |
| 8,821,488 B2 | 9/2014 | Stewart et al. |
| 8,832,927 B2 | 9/2014 | Smith et al. |
| 8,834,461 B2 | 9/2014 | Werneth et al. |
| 8,858,548 B2 | 10/2014 | Asconeguy |
| 8,864,757 B2 | 10/2014 | Klimovitch et al. |
| 8,870,862 B2 | 10/2014 | Edwards et al. |
| 8,894,640 B2 | 11/2014 | Willyard et al. |
| 8,894,642 B2 | 11/2014 | Gibson et al. |
| 8,894,646 B2 | 11/2014 | Edwards et al. |
| 8,906,008 B2 | 12/2014 | Brannan et al. |
| 8,906,012 B2 | 12/2014 | Conley et al. |
| 8,920,414 B2 | 12/2014 | Stone et al. |
| 8,920,415 B2 | 12/2014 | Govari |
| 8,920,417 B2 | 12/2014 | Conley et al. |
| 8,932,281 B2 | 1/2015 | Brannan |
| 8,942,781 B2 | 1/2015 | Carpentier et al. |
| 8,945,015 B2 | 2/2015 | Rankin et al. |
| 8,945,113 B2 | 2/2015 | Brannan et al. |
| 8,945,117 B2 | 2/2015 | Bencini |
| 8,956,353 B2 | 2/2015 | Govari et al. |
| 8,961,511 B2 | 2/2015 | Parmer |
| 8,961,512 B2 | 2/2015 | Horlle et al. |
| 8,968,288 B2 | 3/2015 | Brannan |
| 8,979,833 B2 | 3/2015 | McGill et al. |
| 8,986,292 B2 | 3/2015 | Sliwa et al. |
| 8,986,298 B2 | 3/2015 | Lee |
| 8,986,303 B2 | 3/2015 | Jimenez et al. |
| 8,998,895 B2 | 4/2015 | Besch et al. |
| 9,011,426 B2 | 4/2015 | Van Wyk |
| 9,023,023 B2 | 5/2015 | McKay et al. |
| 9,023,031 B2 | 5/2015 | Ingle et al. |
| 9,028,485 B2 | 5/2015 | Edmunds et al. |
| 9,028,489 B2 | 5/2015 | Choi |
| 9,033,966 B2 | 5/2015 | McKay |
| 9,039,626 B2 | 5/2015 | Courtney |
| 9,039,688 B2 | 5/2015 | Palmer, III et al. |
| 9,039,693 B2 | 5/2015 | Behnke, II et al. |
| 9,039,700 B2 | 5/2015 | Kirschenman |
| 9,044,245 B2 | 6/2015 | Condie et al. |
| 9,055,952 B2 | 6/2015 | Ryan |
| 9,060,756 B2 | 6/2015 | Bencini et al. |
| 9,066,725 B2 | 6/2015 | Christian |
| 9,072,522 B2 | 7/2015 | Morejohn et al. |
| 9,078,663 B2 | 7/2015 | Geiselhart et al. |
| 9,084,590 B2 | 7/2015 | Wittenberger et al. |

(56) References Cited

U.S. PATENT DOCUMENTS

| | | | |
|---|---|---|---|
| 9,084,610 B2 | 7/2015 | Goshgarian et al. |
| 9,089,340 B2 | 7/2015 | Hastings et al. |
| 9,091,603 B2 | 7/2015 | Gliner et al. |
| 9,119,600 B2 | 7/2015 | Richardson et al. |
| 9,108,037 B2 | 8/2015 | Sliwa et al. |
| 9,113,888 B2 | 8/2015 | Orszulak et al. |
| 9,113,924 B2 | 8/2015 | Brannan et al. |
| 9,113,925 B2 | 8/2015 | Smith et al. |
| 9,113,930 B2 | 8/2015 | Reid, Jr. |
| 9,113,932 B1 | 8/2015 | Willyard et al. |
| 9,119,649 B2 | 9/2015 | van der Weide et al. |
| 9,119,650 B2 | 9/2015 | Brannan et al. |
| 9,127,989 B2 | 9/2015 | Brannan et al. |
| 9,131,980 B2 | 9/2015 | Bloom |
| 9,138,289 B2 | 9/2015 | Conley et al. |
| 9,149,321 B2 | 10/2015 | Stringham et al. |
| 9,149,328 B2 | 10/2015 | Dimmer et al. |
| 9,155,589 B2 | 10/2015 | Jenson |
| 9,161,802 B2 | 10/2015 | Przybyszewski |
| 9,161,814 B2 | 10/2015 | Brannan et al. |
| 9,168,093 B2 | 10/2015 | Mihalik et al. |
| 9,173,700 B2 | 11/2015 | Godara et al. |
| 9,179,967 B2 | 11/2015 | Wolf et al. |
| 9,179,968 B2 | 11/2015 | Leo et al. |
| 9,186,197 B2 | 11/2015 | McKay |
| 2001/0007070 A1 | 7/2001 | Stewart et al. |
| 2001/0039419 A1 | 11/2001 | Francischelli et al. |
| 2002/0019644 A1 | 2/2002 | Hastings et al. |
| 2002/0049438 A1 | 4/2002 | Sharkey et al. |
| 2002/0052601 A1 | 5/2002 | Goldberg et al. |
| 2002/0107512 A1 | 8/2002 | Edwards |
| 2002/0115991 A1 | 8/2002 | Edwards |
| 2002/0156471 A1 | 10/2002 | Stern et al. |
| 2002/0169444 A1 | 11/2002 | Mest et al. |
| 2002/0198520 A1 | 12/2002 | Coen et al. |
| 2003/0045872 A1 | 3/2003 | Jacobs et al. |
| 2003/0139740 A1 | 7/2003 | Kreindel |
| 2003/0153905 A1 | 8/2003 | Edwards et al. |
| 2004/0034344 A1 | 2/2004 | Ryba |
| 2004/0049147 A1 | 3/2004 | Edel et al. |
| 2004/0087935 A1 | 5/2004 | Taimisto et al. |
| 2004/0116921 A1 | 6/2004 | Sherman et al. |
| 2004/0147913 A1 | 7/2004 | Sinofsky |
| 2004/0147921 A1 | 7/2004 | Edwards et al. |
| 2004/0176761 A1 | 9/2004 | Desinger |
| 2004/0181214 A1 | 9/2004 | Garabedian et al. |
| 2004/0186467 A1 | 9/2004 | Swanson et al. |
| 2004/0193039 A1* | 9/2004 | Weber ............... G01R 33/285 977/960 |
| 2004/0267256 A1 | 12/2004 | Garabedian et al. |
| 2005/0004562 A1 | 1/2005 | Alcidi et al. |
| 2005/0059862 A1 | 3/2005 | Phan |
| 2005/0059963 A1 | 3/2005 | Phan et al. |
| 2005/0080410 A1 | 4/2005 | Rioux et al. |
| 2005/0096644 A1 | 5/2005 | Hall et al. |
| 2005/0171534 A1 | 8/2005 | Habib |
| 2005/0245920 A1 | 11/2005 | Vitullo et al. |
| 2005/0273093 A1 | 12/2005 | Patel et al. |
| 2005/0283215 A1 | 12/2005 | Desinger et al. |
| 2006/0004356 A1 | 1/2006 | Bilski et al. |
| 2006/0089637 A1 | 4/2006 | Werneth et al. |
| 2006/0122593 A1 | 6/2006 | Jun |
| 2006/0178666 A1 | 8/2006 | Cosman et al. |
| 2006/0253183 A1 | 11/2006 | Thagalingam et al. |
| 2006/0276781 A1 | 12/2006 | van der Weide et al. |
| 2007/0027449 A1* | 2/2007 | Godara ............... A61B 18/1482 606/41 |
| 2007/0049915 A1 | 3/2007 | Haemmerich et al. |
| 2007/0073282 A1 | 3/2007 | McGaffigan et al. |
| 2007/0078453 A1 | 4/2007 | Johnson et al. |
| 2007/0078454 A1 | 4/2007 | McPherson |
| 2007/0156134 A1 | 7/2007 | Rioux et al. |
| 2007/0213703 A1 | 9/2007 | Naam et al. |
| 2007/0265614 A1 | 11/2007 | Stern et al. |
| 2007/0282318 A1 | 12/2007 | Spooner et al. |
| 2007/0287995 A1* | 12/2007 | Mayse ............... A61B 18/1492 606/41 |
| 2008/0077126 A1 | 3/2008 | Rashidi |
| 2008/0103494 A1 | 5/2008 | Rioux et al. |
| 2008/0147056 A1 | 6/2008 | van der Weide et al. |
| 2008/0154257 A1 | 6/2008 | Sharareh et al. |
| 2008/0154258 A1 | 6/2008 | Chang et al. |
| 2008/0161890 A1 | 7/2008 | Lafontaine |
| 2008/0221566 A1 | 9/2008 | Krishnan |
| 2008/0262578 A1 | 10/2008 | Langberg et al. |
| 2008/0269851 A1 | 10/2008 | Deem et al. |
| 2009/0125017 A1 | 5/2009 | Wang et al. |
| 2009/0131854 A1 | 5/2009 | DiCarlo et al. |
| 2009/0149930 A1 | 6/2009 | Schenck |
| 2009/0177193 A1 | 7/2009 | Wang et al. |
| 2009/0187183 A1 | 7/2009 | Epstein |
| 2009/0198309 A1 | 8/2009 | Gowda et al. |
| 2009/0204064 A1 | 8/2009 | Farin et al. |
| 2009/0228003 A1 | 9/2009 | Sinelnikov |
| 2009/0248006 A1 | 10/2009 | Paulus et al. |
| 2009/0254078 A1 | 10/2009 | Just et al. |
| 2009/0254083 A1 | 10/2009 | Wallace et al. |
| 2009/0270849 A1 | 10/2009 | Truckai et al. |
| 2009/0287206 A1 | 11/2009 | Jun |
| 2009/0306652 A1 | 12/2009 | Buysse et al. |
| 2009/0306654 A1 | 12/2009 | Garbagnati |
| 2009/0312756 A1 | 12/2009 | Schlesinger et al. |
| 2010/0030209 A1 | 2/2010 | Govari et al. |
| 2010/0057072 A1 | 3/2010 | Roman et al. |
| 2010/0137837 A1 | 6/2010 | Govari et al. |
| 2010/0137855 A1 | 6/2010 | Berjano Zanon et al. |
| 2010/0168572 A1 | 7/2010 | Sliwa et al. |
| 2010/0168736 A1 | 7/2010 | Wang |
| 2010/0211064 A1 | 8/2010 | Mahapatra et al. |
| 2010/0268223 A1 | 10/2010 | Coe et al. |
| 2010/0312117 A1 | 12/2010 | Fernandez et al. |
| 2011/0009857 A1 | 1/2011 | Subramaniam et al. |
| 2011/0015620 A1 | 1/2011 | Oikonomidis |
| 2011/0022041 A1 | 1/2011 | Ingle et al. |
| 2011/0066147 A1 | 3/2011 | He et al. |
| 2011/0112529 A1 | 5/2011 | Shikhman |
| 2011/0118731 A1 | 5/2011 | Ladtkow |
| 2011/0152855 A1 | 6/2011 | Mayse et al. |
| 2011/0152857 A1 | 6/2011 | Ingle |
| 2011/0160726 A1 | 6/2011 | Ingle |
| 2011/0178584 A1 | 7/2011 | Parmer et al. |
| 2011/0196438 A1 | 8/2011 | Mnozil et al. |
| 2011/0201973 A1 | 8/2011 | Stephens et al. |
| 2011/0213365 A1 | 9/2011 | Eisele et al. |
| 2011/0224667 A1 | 9/2011 | Koblish et al. |
| 2011/0238055 A1 | 9/2011 | Kim et al. |
| 2011/0257649 A1 | 10/2011 | Geistert et al. |
| 2011/0264089 A1 | 10/2011 | Zirkie et al. |
| 2011/0270243 A1 | 11/2011 | Skarda et al. |
| 2011/0295246 A1 | 12/2011 | Prakash et al. |
| 2011/0295249 A1 | 12/2011 | Bloom et al. |
| 2011/0301589 A1 | 12/2011 | Podhajsky et al. |
| 2011/0301591 A1 | 12/2011 | Podhajsky et al. |
| 2011/0306969 A1 | 12/2011 | Coe et al. |
| 2011/0319880 A1 | 12/2011 | Prakash et al. |
| 2012/0029512 A1 | 2/2012 | Willard et al. |
| 2012/0035603 A1 | 2/2012 | Lenihan |
| 2012/0053577 A1 | 3/2012 | Lee et al. |
| 2012/0059286 A1 | 3/2012 | Hastings et al. |
| 2012/0059394 A1 | 3/2012 | Brenner et al. |
| 2012/0089123 A1 | 4/2012 | Organ et al. |
| 2012/0101413 A1 | 4/2012 | Beetel et al. |
| 2012/0123411 A1 | 5/2012 | Ibrahim et al. |
| 2012/0130368 A1 | 5/2012 | Jenson |
| 2012/0136351 A1 | 5/2012 | Weekamp |
| 2012/0143097 A1 | 6/2012 | Pike, Jr. |
| 2012/0143177 A1 | 6/2012 | Avitall |
| 2012/0150165 A1 | 6/2012 | Conley et al. |
| 2012/0172843 A1 | 7/2012 | Sliwa et al. |
| 2012/0172859 A1 | 7/2012 | Condie et al. |
| 2012/0172861 A1 | 7/2012 | Brannan |
| 2012/0203100 A1 | 8/2012 | Weiss et al. |
| 2012/0232544 A1 | 9/2012 | Willyard et al. |
| 2012/0232549 A1 | 9/2012 | Willyard et al. |

(56) References Cited

U.S. PATENT DOCUMENTS

| | | |
|---|---|---|
| 2012/0283725 A1 | 11/2012 | Knowlton et al. |
| 2013/0006238 A1 | 1/2013 | Ditter et al. |
| 2013/0018236 A1 | 1/2013 | Altshuler et al. |
| 2013/0030385 A1 | 1/2013 | Schultz et al. |
| 2013/0030425 A1 | 1/2013 | Stewart et al. |
| 2013/0060245 A1 | 3/2013 | Grunewald et al. |
| 2013/0096550 A1 | 4/2013 | Hill |
| 2013/0150730 A1 | 6/2013 | Altshuler et al. |
| 2013/0172742 A1 | 7/2013 | Rankin et al. |
| 2013/0172876 A1 | 7/2013 | Heard et al. |
| 2013/0253505 A1 | 9/2013 | Schultz |
| 2013/0253509 A1 | 9/2013 | Edwards et al. |
| 2013/0289558 A1 | 10/2013 | Reid, Jr. et al. |
| 2013/0303876 A1 | 11/2013 | Gelfand et al. |
| 2013/0317497 A1 | 11/2013 | Edwards et al. |
| 2013/0324910 A1 | 12/2013 | Ohri et al. |
| 2013/0345699 A1 | 12/2013 | Brannan et al. |
| 2014/0005657 A1 | 1/2014 | Brannan et al. |
| 2014/0012155 A1 | 1/2014 | Flaherty et al. |
| 2014/0012251 A1 | 1/2014 | Himmelstein et al. |
| 2014/0018677 A1 | 1/2014 | Sharonov |
| 2014/0018793 A1 | 1/2014 | Sharonov |
| 2014/0039480 A1 | 2/2014 | Van Wyk |
| 2014/0046174 A1 | 2/2014 | Ladtkow et al. |
| 2014/0066918 A1 | 3/2014 | Stern et al. |
| 2014/0081111 A1 | 3/2014 | Tun et al. |
| 2014/0081112 A1 | 3/2014 | Kim et al. |
| 2014/0081260 A1 | 3/2014 | Cosman, Jr. et al. |
| 2014/0088588 A1 | 3/2014 | Jarrard |
| 2014/0088630 A1 | 3/2014 | Tran et al. |
| 2014/0094684 A1 | 4/2014 | Govan et al. |
| 2014/0094792 A1 | 4/2014 | Sharonov |
| 2014/0094793 A1 | 4/2014 | Sharonov |
| 2014/0094799 A1 | 4/2014 | Ladtkow et al. |
| 2014/0100571 A1 | 4/2014 | Sartor et al. |
| 2014/0121658 A1 | 5/2014 | Cosman, Jr. et al. |
| 2014/0128944 A1 | 5/2014 | Stern et al. |
| 2014/0142431 A1 | 5/2014 | Brannan |
| 2014/0142565 A1 | 5/2014 | Doty et al. |
| 2014/0163360 A1 | 6/2014 | Stevens-Wright et al. |
| 2014/0171942 A1 | 6/2014 | Werneth et al. |
| 2014/0180266 A1 | 6/2014 | Buysse et al. |
| 2014/0200478 A1 | 7/2014 | Phan et al. |
| 2014/0207133 A1 | 7/2014 | Model et al. |
| 2014/0214017 A1 | 7/2014 | Brannan |
| 2014/0257265 A1 | 9/2014 | Godara et al. |
| 2014/0257271 A1 | 9/2014 | Mayse et al. |
| 2014/0257282 A1 | 9/2014 | Wang et al. |
| 2014/0262201 A1 | 9/2014 | Larson et al. |
| 2014/0288546 A1 | 9/2014 | Sherman et al. |
| 2014/0288548 A1 | 9/2014 | Kim et al. |
| 2014/0296680 A1 | 10/2014 | Asirvatham et al. |
| 2014/0296844 A1 | 10/2014 | Kevin et al. |
| 2014/0303616 A1 | 10/2014 | Shin et al. |
| 2014/0303619 A1 | 10/2014 | Pappone et al. |
| 2014/0324042 A1 | 10/2014 | Garabedian et al. |
| 2014/0336733 A1 | 11/2014 | Nebrigic et al. |
| 2014/0350536 A1 | 11/2014 | Allison |
| 2014/0271745 A1 | 12/2014 | Werneth et al. |
| 2015/0005767 A1 | 1/2015 | Werneth et al. |
| 2015/0018727 A1 | 1/2015 | Diederich et al. |
| 2015/0025604 A1 | 1/2015 | McClellan |
| 2015/0038963 A1 | 2/2015 | Panos et al. |
| 2015/0038965 A1 | 2/2015 | Iger |
| 2015/0045780 A1 | 2/2015 | Burnett et al. |
| 2015/0045857 A1 | 2/2015 | Britva et al. |
| 2015/0050614 A1 | 2/2015 | Liu et al. |
| 2015/0057651 A1 | 2/2015 | Bonn |
| 2015/0094708 A1 | 4/2015 | Sartor et al. |
| 2015/0094712 A1 | 4/2015 | Murdeshwar et al. |
| 2015/0119870 A1 | 4/2015 | Rudie |
| 2015/0126986 A1 | 5/2015 | Kelly et al. |
| 2015/0126991 A1 | 5/2015 | Brannan |
| 2015/0148796 A1 | 5/2015 | Bencini |
| 2015/0150627 A1 | 6/2015 | Brannan et al. |
| 2015/0150628 A1 | 6/2015 | Buysse et al. |
| 2015/0157389 A1 | 6/2015 | Ben-Ezra et al. |
| 2015/0157402 A1 | 6/2015 | Kimis et al. |
| 2015/0164571 A1 | 6/2015 | Saadat |
| 2015/0164584 A1 | 6/2015 | Davalos et al. |
| 2015/0164586 A1 | 6/2015 | Brannan |
| 2015/0164587 A1 | 6/2015 | Bonn et al. |
| 2015/0173828 A1 | 6/2015 | Avitall |
| 2015/0190188 A1 | 7/2015 | Lalonde |
| 2015/0190196 A1 | 7/2015 | Jimenez et al. |
| 2015/0202454 A1 | 7/2015 | Burnett |
| 2015/0202467 A1 | 7/2015 | Diederich et al. |
| 2015/0230851 A1 | 8/2015 | Lalonde et al. |
| 2015/0230860 A1 | 8/2015 | Koblish et al. |
| 2015/0238249 A1 | 8/2015 | Edmunds et al. |
| 2015/0238253 A1 | 8/2015 | Wu et al. |
| 2015/0265349 A1 | 9/2015 | Moss et al. |
| 2015/0265365 A1 | 9/2015 | Andrews et al. |
| 2015/0265366 A1 | 9/2015 | Andrews et al. |
| 2015/0272669 A1 | 10/2015 | Brucker et al. |
| 2015/0272671 A1 | 10/2015 | van der Weide et al. |
| 2015/0272672 A1 | 10/2015 | Brannan |
| 2015/0272673 A1 | 10/2015 | Cronin et al. |

FOREIGN PATENT DOCUMENTS

| | | |
|---|---|---|
| WO | WO 97/06739 A2 | 2/1997 |
| WO | WO 99/22659 A1 | 5/1999 |
| WO | 99/32042 | 7/1999 |
| WO | WO 99/35987 A1 | 7/1999 |
| WO | WO 99/44520 A1 | 9/1999 |
| WO | WO 99/48430 A1 | 9/1999 |
| WO | WO 03/053266 A2 | 7/2003 |
| WO | WO 03/053267 A1 | 7/2003 |
| WO | WO 2004/089460 A2 | 10/2004 |
| WO | WO 2007/113866 A1 | 10/2007 |
| WO | WO 2009/014312 A1 | 1/2009 |
| WO | WO 2010/137920 A2 | 12/2010 |
| WO | WO 2011/143468 A2 | 11/2011 |
| WO | WO 2012/086313 A1 | 5/2012 |
| WO | WO 2012/074296 A2 | 6/2012 |
| WO | WO 2012/138056 A1 | 10/2012 |
| WO | WO 2013/008204 A2 | 1/2013 |
| WO | WO 2013/049601 A2 | 4/2013 |
| WO | WO 2013/139178 A1 | 9/2013 |
| WO | WO 2013/140353 A2 | 9/2013 |
| WO | WO 2013/160772 A2 | 10/2013 |
| WO | WO 2013/160837 A1 | 10/2013 |
| WO | WO 2014/012282 A1 | 1/2014 |
| WO | WO 2014/036463 A1 | 3/2014 |
| WO | WO 2014/151510 A1 | 9/2014 |
| WO | WO 2014/151822 A2 | 9/2014 |
| WO | WO 2014/151876 A1 | 9/2014 |
| WO | WO 2014/152575 A2 | 9/2014 |
| WO | WO 2014/153082 A2 | 9/2014 |
| WO | WO 2014/160422 A1 | 10/2014 |
| WO | WO 2014/164445 A1 | 10/2014 |
| WO | WO 2014/166436 A1 | 10/2014 |
| WO | WO 2014/177663 A1 | 11/2014 |
| WO | WO 2014/197625 A1 | 12/2014 |
| WO | WO 2015/021434 A2 | 2/2015 |
| WO | WO 2015/035047 A1 | 3/2015 |
| WO | WO 2015/035287 A1 | 3/2015 |
| WO | WO 2015/057450 A1 | 4/2015 |
| WO | WO 2015/057916 A1 | 4/2015 |
| WO | WO 2015/061478 A1 | 4/2015 |
| WO | WO 2015/074038 A1 | 5/2015 |
| WO | WO 2015/080411 A1 | 6/2015 |
| WO | WO 2015/089377 A1 | 6/2015 |
| WO | WO 2015/1 170 26 A2 | 8/2015 |
| WO | WO 2015/13 8795 A1 | 9/2015 |
| WO | WO 2015/128056 A1 | 9/2015 |

(56) References Cited

OTHER PUBLICATIONS

International Search Report and Written Opinion for PCT/US2017/054834, dated Jan. 15, 2018, 16 pages.

\* cited by examiner

COOLED RF PROBES

RELATED APPLICATION

The present application is the national stage entry of International Patent Application No. PCT/US2017/054834 having a filing date of Oct. 3, 2017, which claims priority to U.S. Provisional Patent Application Ser. No. 62/403,876, filed on Oct. 4, 2016, both of which are incorporated herein in their entirety by reference thereto.

FIELD OF THE INVENTION

The present invention relates generally to electrosurgical devices and methods for the treatment of pain.

BACKGROUND

Electrosurgical procedures typically rely on the application of high frequency, for example radiofrequency (RF), energy to treat, cut, ablate or coagulate tissue structures such as, for example, neural tissue at a specific target site such as a lesion. The high frequency energy is often delivered to a region of tissue from an energy source such as a generator via an active electrode of a probe that is inserted into a patient's body via an introducer. The resistance of tissue that is located proximate the active electrode of the probe to the high frequency energy causes the tissue temperature to rise. If the temperature is increased past a certain tissue-dependent level, referred to as the lesioning temperature, tissue damage will occur, and a lesion will form. Often, the tissue proximate to the probe heats up faster than tissue farther away from the probe, and tissue carbonization and liquid vaporization may occur, all of which may limit the size of the lesion and thus the effectiveness of the treatment. Thus, in order to extend the size of a lesion, the RF treatment may be applied in conjunction with a cooling mechanism. By cooling the probe, the tissue temperature near the probe is moderately controlled. In turn, tissue carbonization and liquid vaporization is minimized, and more power can be applied to the target tissue, resulting in larger lesions and improved physician flexibility.

Several RF probes utilize cooling mechanisms that include a peristaltic pump that distributes coolant water through tubing inside the probe, where the coolant water then absorbs heat from the active electrode tip of the probe through convection. This configuration has addressed issues with carbonization and lesion size, but the pump and the extra tubing take up valuable space during procedures. In addition, when filled with water, the tubing weighs down on the probe and can result in movement of the probe during procedures, which is not ideal. Such movement disrupts the tissue-probe interface, and oftentimes the physician will need to reposition the probe, exposing the patient and physician to extra radiation since fluoroscopy is used to position the probe.

In light of the above, a need currently exists for an electrosurgical device that includes a cooling mechanism that is more patient and physician friendly that does not require repositioning and the unnecessary exposure to additional radiation that coincides with such repositioning.

SUMMARY

In accordance with one embodiment of the present invention, an electrosurgical device is contemplated. The device includes a probe extending in a longitudinal direction, wherein the probe includes a proximal region and a distal region, wherein an inner diameter of the probe defines a lumen, wherein the probe has an electrically insulated portion extending from the proximal region to the distal region and an electrically exposed conductive portion located at the distal region, wherein the electrically exposed conductive portion delivers radiofrequency energy to an area of tissue adjacent the distal region of the probe; and a heat transfer system for removing thermal energy from the area of tissue, wherein the heat transfer system is in thermal contact with the area of tissue, wherein the heat transfer system removes from about 0.1 Watts to about 50 Watts of energy from the area of tissue.

In one particular embodiment, the heat transfer system can remove from about 2 Watts to about 12 Watts of energy from the area of tissue.

In another embodiment, the heat transfer system is at least partially disposed within the lumen.

In yet another embodiment, the heat transfer system can be configured to absorb or remove thermal energy over a time period ranging from about 60 seconds to about 300 seconds.

In still another embodiment, the heat transfer system can include a heat removal material in thermal contact with the area of tissue. The heat removal material can be disposed within the lumen, and/or can be positioned on an exterior surface of the probe, an introducer, or a combination thereof.

Further, the heat removal material can include a heat transfer material, a heat sink, or a combination thereof.

In one particular embodiment, the heat transfer material can include a thermally conductive material, one or more Peltier circuits, or a combination thereof. The thermally conductive material can include a metal, a ceramic material, a conductive polymer, or a combination thereof.

When the thermally conductive material is a metal, the metal can include a silver paste.

Meanwhile, when the heat transfer material includes one or more Peltier circuits, the one or more Peltier circuits can be positioned within a hub of the electrosurgical device, a handle of the electrosurgical device, the distal region of the probe, the proximal region of the probe, or a combination thereof, wherein a connection exists between the one or more Peltier circuits and the distal region of the probe. Further, each Peltier circuit can include a hot side and a cold side, wherein the hot side faces the proximal region of the probe and the cold side faces the distal region of the probe.

In yet another embodiment, when the heat removal material includes a heat sink, the heat sink can include a phase change material. The phase change material can change phase at a temperature between about 40° C. and 100° C. In addition, the phase change material can have a heat of fusion ranging from about 150 Joules/gram to about 300 Joules/gram. Moreover, from about 1 gram to about 12 grams of the phase change material can be required to remove from about 2 Watts to about 12 Watts of energy from the probe over a 150 second time period. Further, the phase change material can include a paraffin wax. In one embodiment, the phase change material can surround a conductor extending from the electrically exposed conductive portion of the probe at the distal region of the probe towards a proximal end of the probe.

In still another embodiment, the heat sink can be a gas or a pressurized liquid, wherein the gas or the pressurized liquid is contained within the lumen. Further, the gas can be carbon dioxide or nitrogen and the liquid can be liquid carbon dioxide. The lumen can contain an inlet channel, wherein the gas or pressurized liquid is introduced into the lumen, and an outlet channel where the gas or pressurized liquid exits the lumen, wherein the inlet channel and the outlet channel are defined by a separator, wherein the inlet channel has a diameter that is smaller than a diameter of the outlet channel.

In yet another embodiment, the heat sink can include an endothermic reaction system, wherein the endothermic reaction system includes a first material separated from a second material, wherein an endothermic reaction occurs when the first material contacts the second material. The first material can include water and the second material can include ammonium nitrate. Further, the first material and the second material can be stored in a cartridge that can be inserted into the lumen prior to use of the electrosurgical device. Moreover, such a heat transfer system can further include a wire, where the wire facilitates the transfer of heat from the electrically exposed conductive portion of the probe to the endothermic reaction between the first material and the second material.

In yet another embodiment, wherein the heat transfer material can be in thermal communication with the heat sink.

In still another embodiment, the heat sink can be an external heat sink. Further, the heat transfer material can be in communication with the heat sink via one or more conductive wires or conduits.

In one more embodiment, the heat sink can include a series of fins, etchings, particulates, or a combination thereof so that the heat sink exhibits increased surface area to facilitate removal of heat from the tissue.

In one more embodiment, the area of tissue adjacent the distal region of the probe can be maintained at a temperature of less than about 90° C.

In yet another embodiment, the heat transfer system can be free of a circulating liquid.

In still another embodiment, the heat transfer system can be free of a pump.

Other features and aspects of the present disclosure are discussed in greater detail below.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Figure 1A:
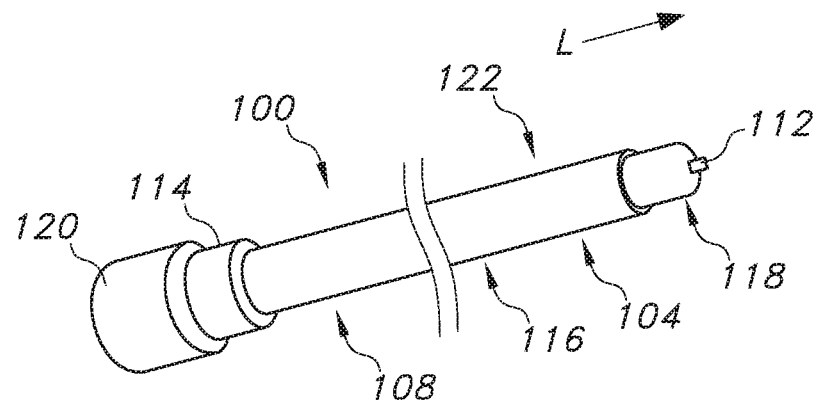
FIG. 1A is a perspective view of an embodiment of a probe that can be used in conjunction with one embodiment of the system contemplated by the present invention.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Generally, the present invention is directed to an electrosurgical device that includes a probe extending in a longitudinal direction, wherein the probe includes a proximal region and a distal region, and wherein an inner diameter of the probe defines a lumen. The probe has an electrically insulated portion extending from the proximal region to the distal region and an electrically exposed conductive portion located at the distal region, wherein the electrically exposed conductive portion delivers radiofrequency energy to an area of tissue. The electrosurgical device also includes a cooling or heat transfer system that is in thermal contact with the area of tissue, where the cooling or heat transfer system is capable of removing from about 0.1 Watts to about 50 Watts, such as from about 0.5 Watts to about 40 Watts, such as from about 1 Watt to about 25 Watts, such as from about 2 Watts to about 12 Watts from the area of tissue through the electrosurgical device in order to prevent charring or carbonization of the tissue. In addition, the cooling or heat transfer system can be designed in such a manner that it does not require the use of a peristaltic pump to circulate a liquid (e.g., water) inside a lumen of the probe in order to sufficiently cool the area of tissue being treated. In one particular embodiment, the cooling or heat transfer system can be at least partially disposed within a lumen of the probe, while in other embodiments, the cooling or heat transfer system can be positioned on an exterior surface of the probe, an introducer component of the electrosurgical device, or a combination thereof so long as the cooling or heat transfer system is in thermal communication with the area of tissue being treated, such as via a thermally conductive region of the probe located at the distal end or distal region of the probe.

For instance, the heat transfer system can include a heat removal material that can include a heat transfer material, a heat sink, or a combination thereof. The heat removal material can be placed in thermal contact with the area of tissue being treated and can be used to transfer heat away or absorb heat from an interface between the tissue and the probe of the electrosurgical device. Further, when the heat removal material includes both a heat transfer material and a heat sink, the heat transfer material can direct the heat towards the heat sink, which then absorbs the heat from the tissue. As discussed below, various types of materials can be used for the heat transfer material and the heat sink. Regardless of the specific material used for the heat transfer material specifically, the heat transfer material can have a heat transfer coefficient that is sufficiently high enough to maintain the tissue temperature at the tissue/probe interface below a desired temperature, such as below about 90° C., which is the temperature at which charring and carbonization of the tissue can occur and the temperature at which tissue impedance spikes. Specific embodiments contemplated by the present invention are discussed in detail below.

Figure 1B:
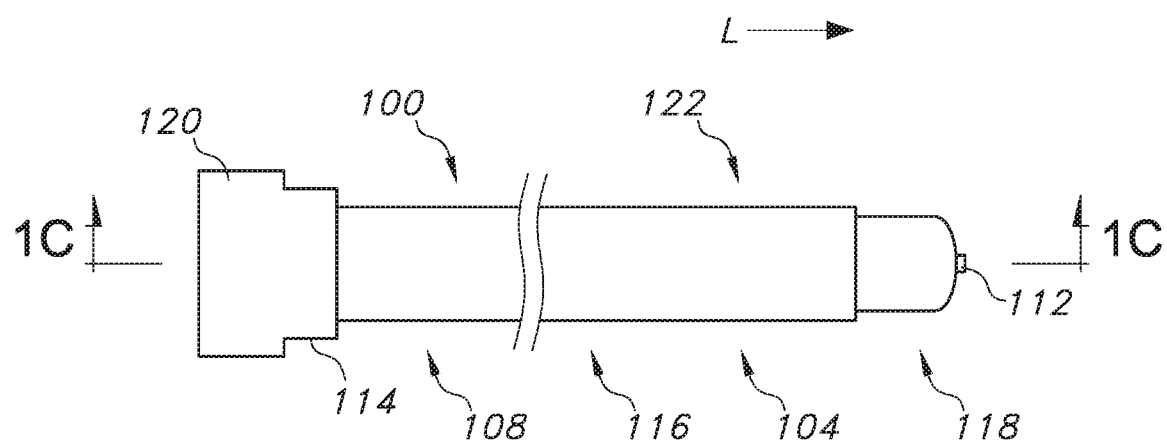
FIG. 1B is a top view of the embodiment of FIG. 1A.
Figure 2A:
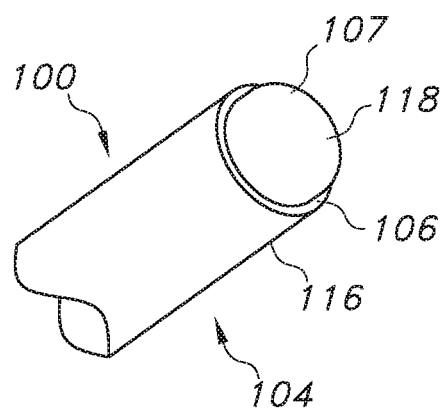
FIGS. 2A to 2D are perspective views showing configurations of electrically insulated portions and electrically exposed conductive portions (i.e., active electrode portions) of several embodiments of a probe that can be used in conjunction with the system contemplated by the present invention.
Figure 2B:
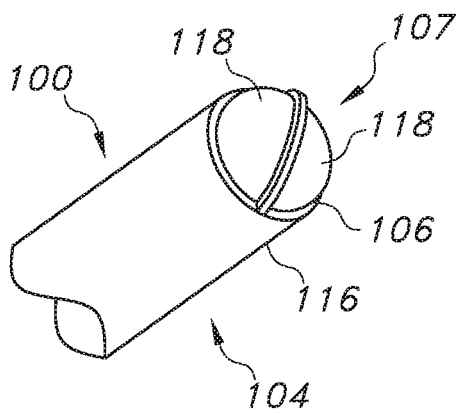
Figure 2C:
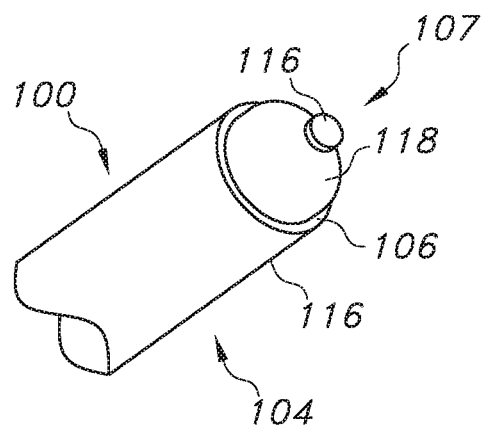
Figure 2D:
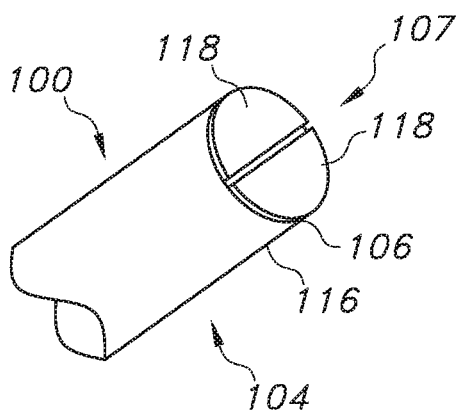

Referring now to the drawings, and beginning with FIGS. 1A and 1B, various features of the device are discussed in more detail. As shown, the electrosurgical instrument or device may be a probe 100; however, in other embodiments, the electrosurgical instrument or device may be a cannula, a catheter, or any other elongate member capable of delivering energy to a target site within a patient's body. For the sake of clarity, the term "probe" is used throughout the specification to describe any such device. The probe 100 may be an elongate member that can include a shaft 122, a distal region 104, a distal end 106, a distal face 107, a proximal region 108, and a proximal end 110. As used herein, the terms "distal" and "proximal" are defined with respect to the user and when the device is in use. That is, the term "distal" refers to the part or portion further away from the user and closest to the treatment site, while the term "proximal" refers to the part or portion closer to the user and farthest from the treatment site when the device is in use.

As shown in the embodiments contemplated by FIGS. 1A and 1B, the probe 100 can include an electrically insulated portion 116 and an electrically exposed conductive portion 118. The electrically exposed conductive portion 118 can also be referred to as an active electrode, and when the exposed conductive portion is located at the distal end of probe 100, it may be referred to as an active tip. In general, the electrically insulated portion 116 may extend from the proximal region 108 of the probe 100 to a location in the distal region 104 of the probe 100. The location to which electrically insulated portion 116 extends may depend on the application, as will be discussed in more detail below. Furthermore, the location to which electrically insulated portion 116 extends may not be fixed. In other embodiments, as shown in FIGS. 2A to 2D, the probe 100 can include more than one electrically insulated portion 116 and/or more than one electrically exposed conductive portion 118.

Figure 6:
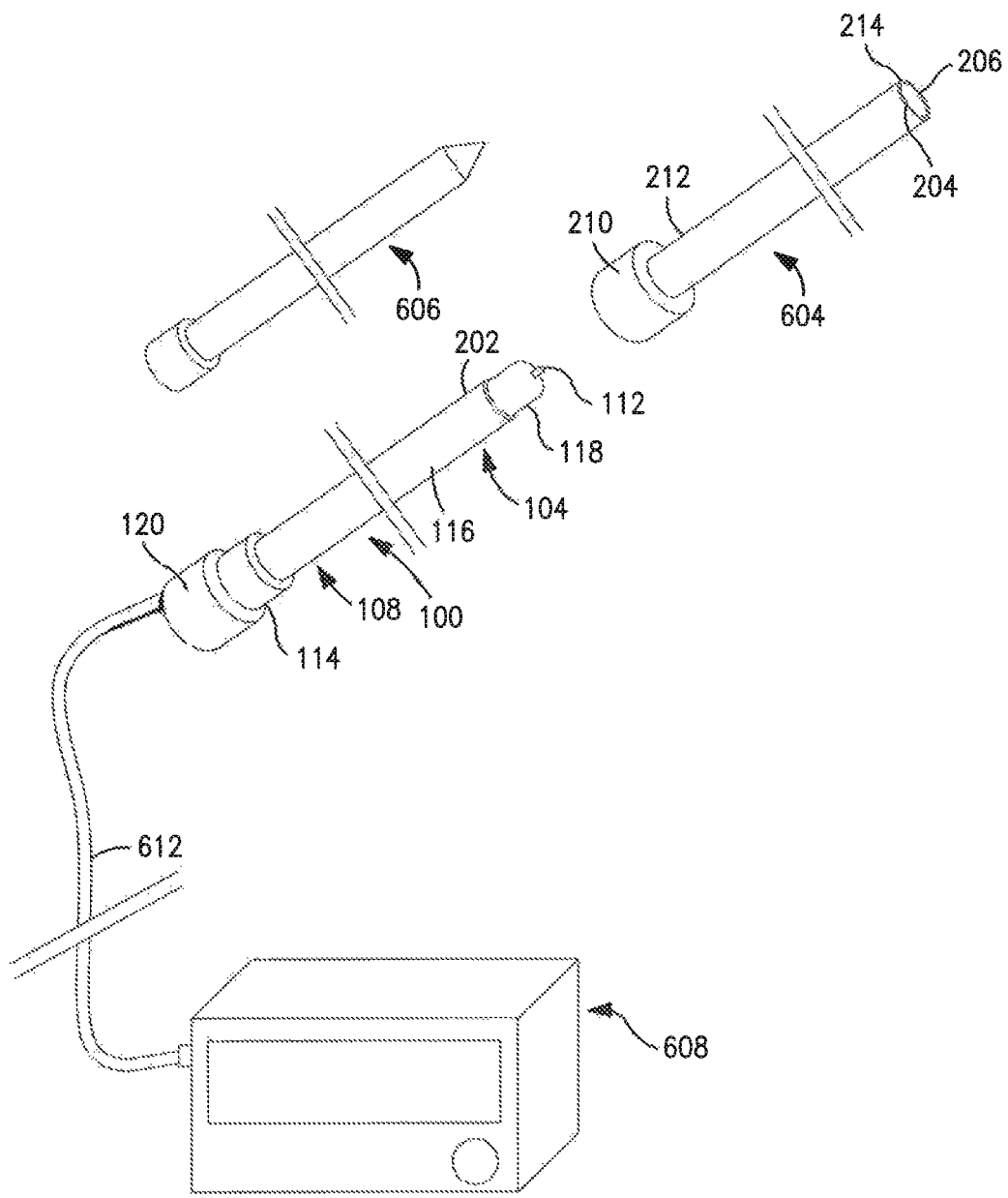
FIG. 6 is a perspective view of an embodiment of a system contemplated by the present invention.

In some embodiments, for example as shown in FIGS. 1A and 1B, the proximal region 108 of the probe 100 can include a hub 114. The hub 114 may be structured to securely connect other devices such as introducers, connector cables, cannulae, tubes, or other hubs, for example, to the probe 100. For example, as shown in FIG. 6 and discussed in further detail below, the probe 100 may be coupled to an energy source and/or to a source of cooling via respective connecting means (for example, an electrical cable and/or flexible tubing) which may be associated with the hub 114 (also shown in FIG. 3). The hub 114 may also serve as a handle or grip for the probe 100 and can serve as a locking mechanism to secure the probe 100 to an introducer 604, as discussed in more detail below with respect to FIGS. 17 to 21. The hub 114 may be manufactured from a number of different materials, including, but not limited to, plastics, polymers, metals, or combinations thereof. Furthermore, the hub 114 may be attached to probe 100 by a number of different means. For example, in one embodiment, the hub 114 may be made from polypropylene, and may be attached to probe 100 by any suitable fitting such as a luer fitting. Although the hub 114 can serve as a handle, it is also to be understood that a separate handle 120 is also contemplated (see FIG. 6).

The size and shape of the probe 100 may vary depending on the application, and the invention is not limited in this regard. For example, in some embodiments, the transverse cross sectional shape of the probe 100 may be substantially circular. In other embodiments, the cross-sectional shape may be substantially polygonal, elliptical, or any other desired shape. In some embodiments, the length from the distal end 106 to proximal end 110 of the probe 100 may be between about 5 centimeters (cm) and about 40 cm and the outer diameter of shaft 122 may be between about 0.65 millimeters (mm) and about 2.00 mm (between about 20 AWG and about 12 AWG). In one specific example, the length of the probe may be about 7.5 cm, the outer diameter may be about 1.5 mm, and the transverse cross-sectional shape may be substantially circular. Further, it is to be understood that the shape of the distal end 106 may vary depending on the application. Possible shapes include, but are not limited to, blunt, rounded, sharp, and beveled.

The probe 100 may be rigid or flexible and may be straight, bent or angled at one or more points along its length. As used herein, the term "bent" refers to any region of non-linearity or any deviation from a longitudinal axis, gradual or abrupt, and at any angle. In embodiments wherein the probe 100 is bent, the bend may be at various locations along the probe 100, for example in the distal region 104. Furthermore, the bend may be of a variety of degrees and lengths. For example, the bend may traverse about 25° of a circle, and occur over a length of about 5 mm. In addition, the probe 100 can include a plurality of bends, which may or may not be in the same plane. For example, in some embodiments, the probe 100 may be bent such that it is helical or "corkscrew" shaped. In some embodiments, the probe 100 may be structured such that its shape may be modified by a user before or during the course of a procedure. More specifically, the shape of the distal region 104, for example, may be modified such that it may change from a straight to a bent configuration using an actuating mechanism. This may aid in accessing difficult to reach sites within the body and can be accomplished by a variety of means. For example, the probe 100 can include at least one active shape control mechanism, including but not limited to one or more pull-wires, a hydraulic or piezoelectric device, or another actuating mechanism.

In one embodiment, the electrically insulated portion 116 may be formed by coating a portion of the shaft 122 with an electrically insulative coating, covering, or sheathing. In other words, the probe 100 can include electrically insulative material disposed on the surface of the elongate member. For example, in one embodiment, the shaft 122 of the probe 100 may be fabricated from a biocompatible metal or alloy, for example stainless steel, which may be overlaid in part by an insulating coating, for example polytetrafluoroethylene (PTFE). In other embodiments, the shaft 122 can be fabricated from another metal, such as nitinol or titanium, and/or another electrically insulating material, including but not limited to polyethylene terephthalate (PET), may be disposed thereon. In other embodiments, other metals or electrically insulating materials may be used, and the invention is not limited in this regard. Furthermore, the insulating material may be semi-porous, to allow for some leakage of current through the insulating material. In some embodiments, the material may also be a thermal insulator as well. In still other embodiments, different insulating materials can be used for different portions of the probe 100. The insulating coating may be applied to a portion of shaft 122 by dip-coating, spraying or heat shrinking, for example. Meanwhile, the remaining uncoated portion of the distal region of the shaft 122 may serve as a conductive portion 118.

In another embodiment, the shaft 122 of the probe 100 can be fabricated from an insulative or non-conductive material and may be furnished with one or more externally applied electrodes 118. In such embodiments, the probe 100 can include one or more wires that may be attached to the electrode(s) 118 at one end, and can run proximally along the shaft 122, such that a proximal portion of the wire(s) may be operatively connected to an energy source, thereby supplying energy to the electrodes 118. For example, the shaft 122 can be fabricated from Radel™ plastic, and the externally applied electrodes can be fabricated from stainless steel.

In alternate embodiments, the shaft 122 may be manufactured from a combination of materials. For example, the distal region 104 of the shaft 122 can be made from a material such as nitinol, such that the shape of the distal region 104 may be altered, and the remainder of shaft 122 may be made from stainless steel, such that the remainder of shaft 122 may be substantially fixed.

As discussed above, the electrosurgical device of the present invention contemplates a probe 100 that can include a heat transfer system to facilitate cooling of the area tissue being treated via various heat transfer materials, heat sinks, or a combination thereof. Several embodiments of the internal structure of the probe 100 of FIG. 1 incorporating various cooling or heat transfer systems contemplated by the present invention are shown FIGS. 3A to 3F, which represent cross-sectional view of the probe 100 of FIG. 1B at cut line 1C.

Figure 3A:
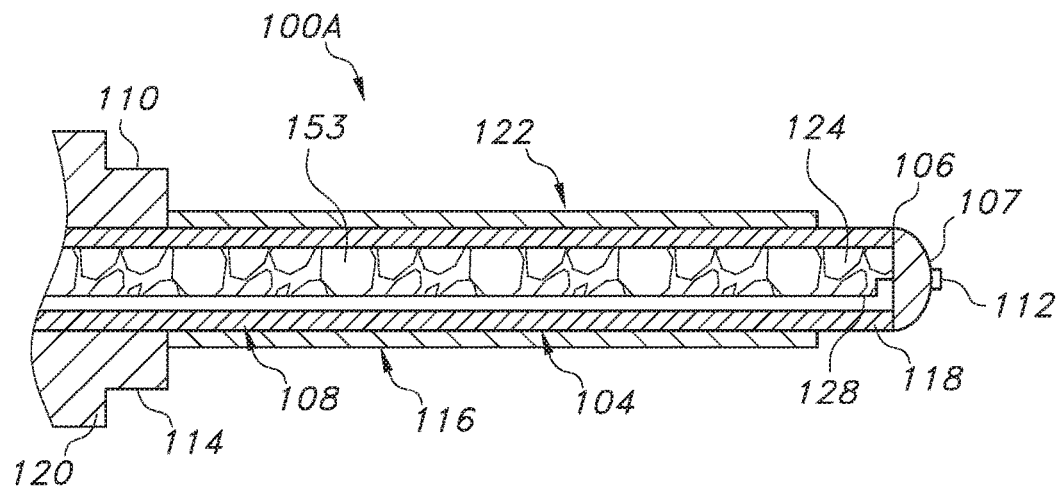
FIGS. 3A to 3F are cross sectional views of several embodiments of probes with internal cooling that can be used in the system contemplated by the present invention.

Turning first to FIG. 3A, an electrosurgical device including a probe 100A with one embodiment of a cooling or heat transfer system contemplated by the present invention is shown. In order to facilitate sufficient cooling of the tissue being treated during use of the electrosurgical device, the lumen 124 of the probe 100A can be filled with a heat transfer material such as a thermally conductive ceramic material 153 or any other suitable heat transfer material. Any suitable ceramic material can be used as long as it has a sufficiently high thermal conductivity to facilitate transfer of the heat from the tissue to the ceramic material 153. Examples include but are not limited to alumina, aluminum nitride, beryllium oxide, boron nitride or a combination thereof. Regardless of the particular ceramic material utilized, the ceramic material can have a thermal conductivity (sometimes called "Lambda") of at least about 20 W/mK (Watts per kelvin per meter), such as a thermal conductivity ranging from about 20 W/mK to about 400 W/m K, such as from about 25 W/mK to about 375 W/m K, such as from about 30 W/mK to about 350 W/m K.

Regardless of the particular type of ceramic material used for the thermally conductive ceramic material 153, the thermally conductive ceramic material 153 can be positioned inside the lumen 124 of the probe 100A. However, it is to be understood that the thermally conductive ceramic material 153 can be located on any suitable surface or within any component of the electrosurgical device so long as it is in communication with a thermally conductive region of the probe 100A in order to facilitate cooling of the tissue near the thermally conductive region of the probe 100A. For instance, it is also possible to wrap the exterior surface of the probe 100A with the thermally conductive ceramic material 153 in order to facilitate the transfer of the heat away from the tissue. In addition, other components of the electrosurgical device, such as the introducer 604 (see FIG. 6), can also be formed from the thermally conductive ceramic material 153 or can be in contact with the thermally conductive ceramic material 153 to facilitate heat transfer away from the tissue.

Figure 3B:
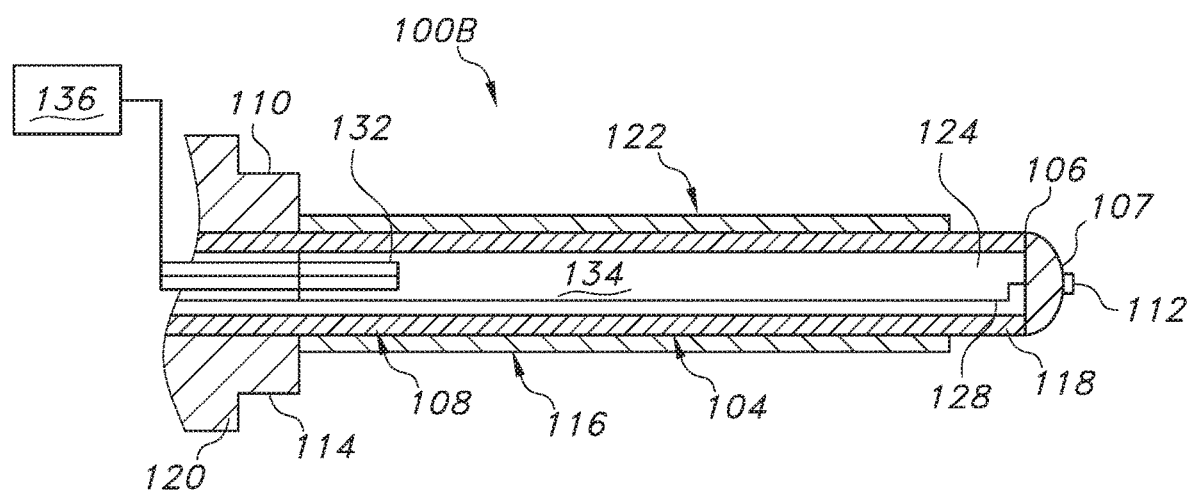

Further, the present invention also contemplates the use of any other thermally conductive material 134 (e.g., a metal, a conductive polymer, or a combination thereof) to cool a probe 100B, as shown in FIG. 3B, where the thermally conductive material 134 can be used to transfer heat away from a region of tissue and the distal face 107 of the probe 100B. Although FIG. 3B is discussed below with respect to a metal (e.g., silver paste), conductive polymers can also be used alone or in combination with a metal or any other thermally conductive material, such as the thermally conductive ceramic materials discussed above. The conductive polymer can be a pre-compounded polymer resin or can be a combination of a base polymer resin and one or more thermally conductive additives (e.g., boron nitride, carbon fibers, carbon powder, stainless steel fibers, nickel-coated graphite, etc. or a combination thereof).

Specifically, the lumen 124 of the probe 100B can be filled with the thermally conductive material 134. By filling the probe 100B with the thermally conductive material 134, heat can easily flow away from the active tip at the distal face 107 of the probe 100B and could be transferred to a heat sink, such as heat sink 136, which can be made from any of the heat sink materials discussed in the present application in more detail below. In one particular embodiment, the thermally conductive material 134 can include a metal, such as a silver paste, and thermally conductive wires 132 can be positioned in the paste, where the thermally conductive wires can exit the proximal end 110 of the probe 1006 and lead to the heat sink 136. Such an arrangement can provide for an external cooling source that is not confined by the space of the probe 1006 to allow for additional cooling, although it is to be understood that the heat sink 136 can alternatively be located within the probe or other components of the electrosurgical device (hub, handle, introducer/cannula, etc.). In addition, it is to be understood that the thermally conductive material 134 can be located on any suitable surface or within any component of the electrosurgical device so long as it is in communication with a thermally conductive region of the probe 1006 in order to facilitate cooling of the probe. For instance, the thermally conductive material 134 can be positioned on an exterior surface of the probe 1006, an introducer (see introducer 604 in FIG. 6), or a combination thereof. Moreover, it is to be understood that although the heat sink 136 is shown as being external, it can be located within the probe 100B or any of the other components of the electrosurgical device as well. Further, although the heat sink 136 is shown in use with a thermally conductive metal as the heat transfer material, the heat sink 136 can be used in conjunction with any of the heat transfer materials discussed with respect to FIGS. 3A-3C.

The heat sink 136 can be any material with a high specific heat, a phase change material, materials to initiate an endothermic chemical reaction, pressurized liquids, gases, or any other suitable material. In other words, the heat sink 136 can be formed from any material that can absorb heat away from the distal end 106 and/or distal region 104 of the probe 1006 and can that has a high heat capacity where the energy being transferred from the tissue through the heat transfer material (e.g., thermally conductive ceramic material, metal, thermally conductive polymer, etc.) to the heat sink 136 acts to slowly increase the temperature of the heat sink 136 such that the during the course of the radiofrequency treatment, the interface between the probe and the tissue is maintained at a temperature of less than about 90° C. Moreover, it should be understood that if a liquid is used in the heat sink 136, the liquid does not need to be circulated in and out of the heat sink 136 and can be stagnant and fully contained within the heat sink 136. In addition, the heat sink 136 can possess a high surface area where the energy being transferred from the tissue through the heat transfer material to the heat sink 136 is dissipated through convective or radiative cooling to the environment such that during the course of the radiofrequency treatment, the interface between the probe and the tissue is maintained at a temperature of less than about 90° C., where the high surface area can be created through a series of fins, etchings, particulate deposition steps, etc.

Figure 3C:
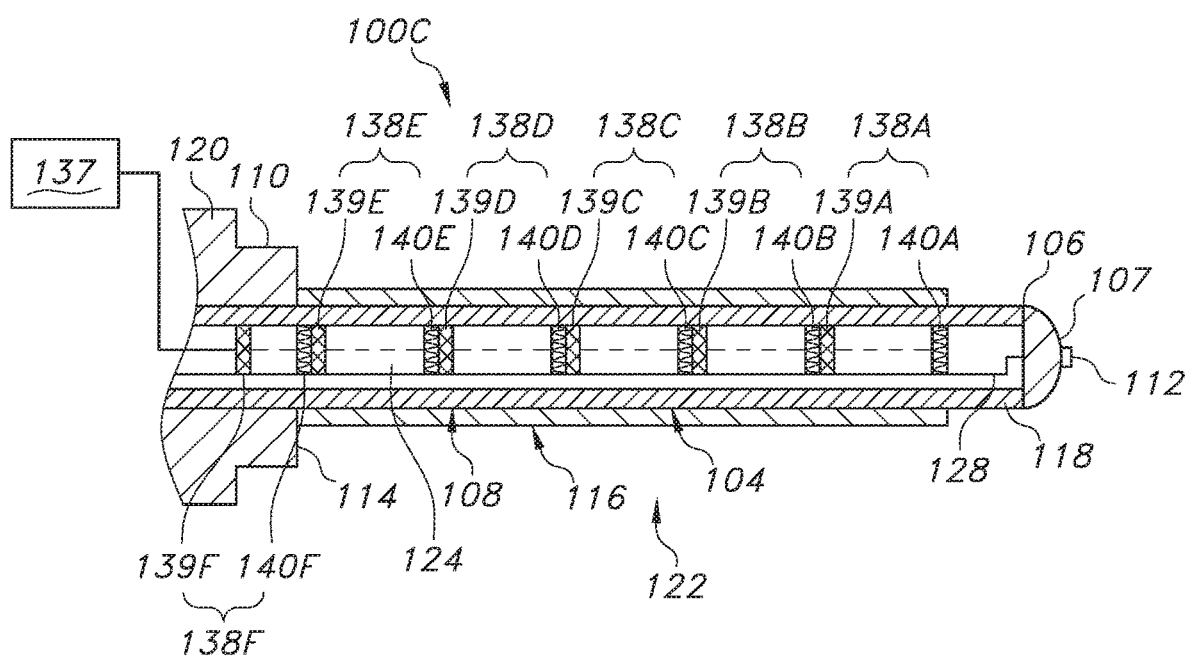

Referring now to FIG. 3C, the present invention also contemplates a probe 100C where the tissue being treated can be cooled by a thermoelectric circuit that includes one or more Peltier circuits, which can be arranged in series or in any other suitable arrangement. Specifically, the probe 100C may partially or fully house a circuit comprising two dissimilar metals or semiconductors, for example P- and N-doped bismuth-telluride, which are joined together at two junctions. When current passes through the circuit, heat may be transferred from one junction to the other. This phenomenon is known as the Peltier effect. The junction where the heat is transferred from may be located in the distal end 106 of the probe 100C, and the junction where the heat is transferred to may be located at a proximal end 110 of the probe 100C or externally to the probe 100C. Energy may be provided to the circuit by an external energy source (for example, the same energy source that delivers RF energy to the probe 100C), or an additional power source 137 such as an electrical generator or a battery, for example.

In one particular embodiment, at least two Peltier circuits 138A and 138B are positioned within the lumen 124 of the probe 100C. The Peltier circuit 138A includes a hot side 139A and a cold side 140A, while the Peltier circuit 138B includes a hot side 139B and a cold side 140B, where the hot sides 139A and 139B are heated up and may be in thermal contact with any of the heat sinks discussed herein in order to facilitate cooling of the cold sides 140A and 140B, which are positioned closer to the distal end 106 of the probe 100C to cool the distal face 107 and tissue adjacent thereto. In other embodiments, additional Peltier circuits 138C, 138D, 138E, and 138F can also be utilized to provide additional cooling, where the circuits include hot sides 139C, 139D, 139E, and 139F positioned closer towards the proximal end 110 of the probe 100C and cold sides 140C, 140D, 140E, and 140F positioned closer towards the distal end 106 of the probe 100C. By utilizing a series of Peltier circuits as discussed above, such as at the individual Peltier circuits can use less energy and have smaller temperature differences, which translates to the handle 120 not heating up so much that it could not be grasped by a user. Further, although the Peltier circuits 138A through 138F are shown as being positioned within the lumen 124 of the probe 100C from its proximal region 108 or proximal end 110 to its distal region 104 or distal end 106, the Peltier circuit or circuits can alternatively or additionally positioned within the hub 114 of the electrosurgical device, a handle of the device, etc. as long as a connection exists between the one or more Peltier circuits and the distal end 106 of the probe 100C.

Figure 3D:
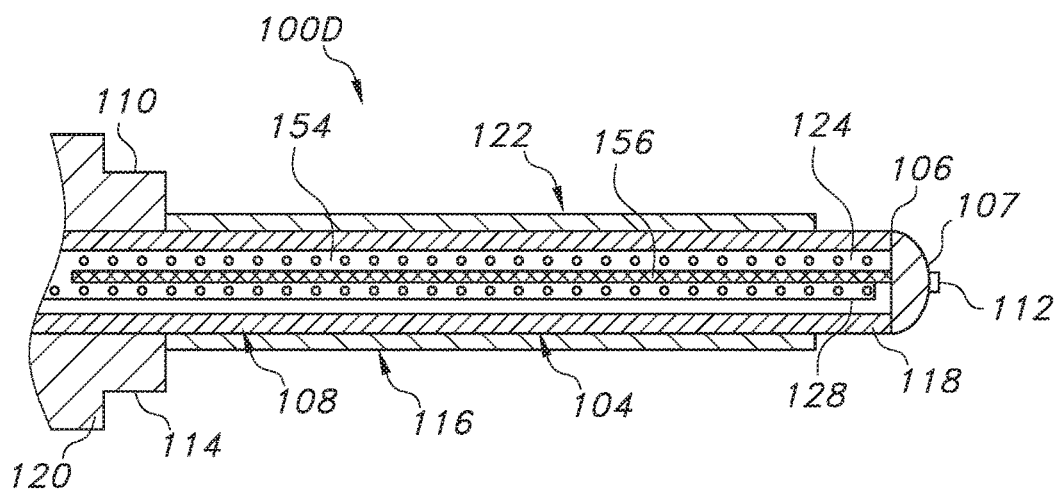

Referring now to FIG. 3D, an electrosurgical device including a probe 100D with another embodiment of a cooling or heat transfer system contemplated by the present invention is shown. In order to facilitate sufficient cooling of the tissue being treated during use of the electrosurgical device, the lumen 124 of the probe 100D can be filled with a phase change material 154, which acts as a heat sink. Cooling of the tissue via a phase change material 154 utilizes a method by which a phase change material is brought up to a temperature when it begins to change phase from either a liquid to a gas or a solid to a liquid. Once the phase change process begins, the temperature of the phase change material 154 will not increase, but the phase change material 154 will continue to absorb heat from the surrounding environment until the entire phase change material 154 has changed phase.

In one particular embodiment, the phase change material 154 can be a wax (e.g., paraffin wax or any other suitable wax) that changes phase at a temperature between about 40° C. and about 100° C., such as a temperature between about 45° C. and about 95° C., such as at a temperature of between about 50° C. and about 90° C. For example, for a phase change material 154 that is a wax having a phase change temperature of 50° C., its temperature will stay at 50° C., but the wax will continue to absorb heat from the probe 100D and tissue at a rate dependent upon the heat of fusion of the particular wax or other phase change material 154 utilized until all such wax has transitioned from the sold state to the liquid state. In one particular embodiment when the phase change material 154 is a paraffin wax, which has a heat of fusion of about 200 J/g, in order to sink 6 Watts of energy from the tissue and probe 100D over a 150 second period, which equals about 900 Joules, about 4.5 grams of the paraffin wax would need to change phase. Thus, depending on the particular phase change material utilized, from about 1 gram to about 12 grams, such as from about 3 grams to about 6 grams, such as from about 3.5 grams to about 5 grams, such as from about 4 grams to about 4.5 grams of the phase change material needs to change phase to sufficiently cool the tissue (e.g., remove from about 2 Watts of energy to about 12 Watts of energy from the tissue and probe) when the phase change material has a heat of fusion ranging from about 150 J/g to about 300 J/g, such as from about 175 J/g to about 275 J/g, such as from about 200 J/g to about 250 J/g.

In any event, the phase change material 154 can be filled in the lumen 124 of the probe 100D so that the phase change material 154 is in contact with the electrically exposed conductive portion 118 of the probe 100D so that there is sufficient thermal contact with the area of tissue being treated. Further, the phase change material 154 can surround a conductor 156 that extends from the electrically exposed conductive portion 118 at the distal face 107 of the probe 100D to the proximal region 108 of the probe 100D, where the conductor runs through the center of the phase change material 154 to provide improved heat transfer away from the distal face 107 of the probe 100D. In addition, it is to be understood that the phase change material 153 can be located on any suitable surface or within any component of the electrosurgical device so long as it is in communication with a thermally conductive region of the probe in order to facilitate cooling of the probe. For instance, the phase change material 154 can be positioned on an exterior surface of the probe 100D, an introducer (see introducer 604 in FIG. 6), or a combination thereof.

Figure 3E:
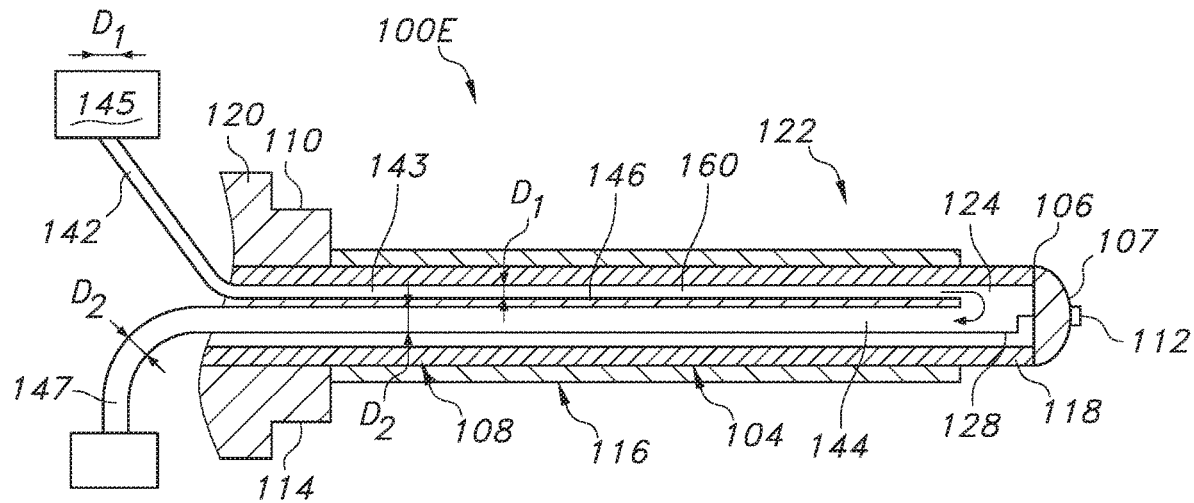

Next, referring to FIG. 3E, an electrosurgical device including a probe 100E with another embodiment of a cooling or heat transfer system contemplated by the present invention is shown. In order to facilitate sufficient cooling of the tissue being treated during use of the electrosurgical device, the lumen 124 of the probe 100E can be filled with gas such as nitrogen or carbon dioxide or a pressurized liquid such as liquid carbon dioxide to as act as a heat sink. As shown in FIG. 3E, the gas or pressurized liquid 160 can be delivered to the lumen 124 of the probe 100E from a gas or pressurized liquid source 145 via an inlet 142 and into an inlet channel 143 inside the lumen 124. Then, the gas or pressurized liquid 160 can travel through the inlet channel 143 from the proximal region 108 of the probe 100E to the distal end 106 of the probe 100E, where the gas or pressurized liquid then enters an outlet channel 144 and travels from the distal end 106 of the probe 100E to the proximal region 108 of the probe 100E, where the gas or pressurized liquid 160 can exit the probe 100E via outlet tubing 147. Referring to FIG. 3E, a separator 146 can be used to form the inlet channel 143 and the outlet channel 144.

The gas or pressurized liquid 160 can be introduced to the probe 100E such that the gas or pressurized liquid 160 expands near the distal face 107 of the probe 100E. As the gas or pressurized liquid 160 expands, the temperature of the tissue and probe 100E at the distal face 107 can be lowered to provide cooling to the tissue and probe 100E according to the ideal gas law $PV=nRT$, where P=Pressure, V=Volume, n=number of moles, R=Universal gas constant, and T=Temperature, where it follows that if the pressure drops due to expansion, the temperature will also drop. In one particular embodiment, the gas or pressurized liquid expands at the distal face 107 due to an increase in diameter D2 of the outlet channel 144 and optional outlet tube 147 as compared to the diameter D1 of the inlet tube 142 and inlet channel 143, which, in turn, results in a decrease in temperature of the gas or pressurized liquid, which, in turn, results in a decrease in temperature at the distal face 107 of the probe 100E. It is to be understood that as the pressurized liquid expands, it changes phase into a gas so that the pressurized liquid leaves the outlet channel 144 as a gas. It is also to be understood that the probe 100C is designed to withstand the increased pressures at the inlet channel 143 as well as the cooling that occurs.

Figure 3F:
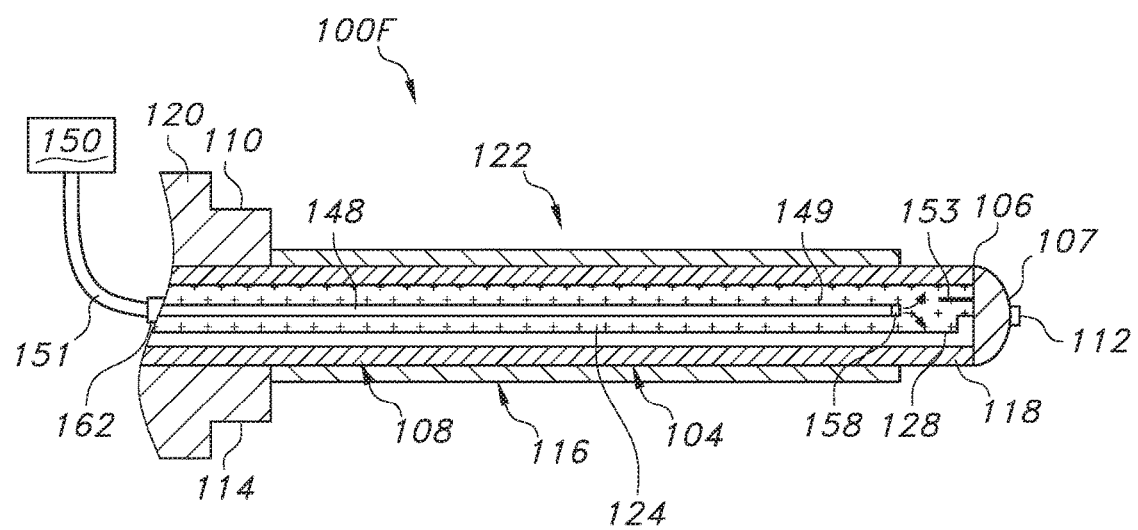

In an alternate embodiment, as shown in FIG. 3F, the present invention contemplates a probe 100F where the tissue being treated may be cooled chemically, such as via an endothermic reaction between two materials, where the reaction between the two materials acts as a heat sink to absorb heat from the tissue. For instance, the two materials can be water and ammonium nitrate. The materials can be stored separately such that when mixed, an endothermic reaction or endothermic mixing occurs. When the materials mix, thermal energy will be absorbed, and the distal region 104 of the probe 100F near the distal face 107 will be cooled, which then facilitates cooling of the tissue being treated with the electrosurgical device. Cooling can be facilitated via a wire 153, which can be made of copper, where the wire 153 can transfer the heat from the active tip at the distal face 107 to the reaction. The product(s) of the endothermic reaction or the resulting mixture may exit the probe 100F via the open proximal end 110.

One example of a suitable reaction for the chemical cooling of the tissue being treated via the probe 100F may be the mixing of water and ammonium nitrate, where the water is contained in water channel 148 that is closed at the distal end 106 of the probe 100F via a seal 158 that can be ruptured via any suitable means, such as by pressing a button 162 or by twisting, to cause the water, which can be stored in water source 150, to mix with the ammonium nitrate, which can be stored in an additional channel 149. In one particular embodiment, in order to sink from about 2 Watts of energy to about 12 Watts of energy from the tissue and probe 100F over up to a 150 second period, from about 0.2 grams to about 5 grams of water, such as from about 0.3 grams to about 4 grams of water, such as from about 0.4 grams of water to about 3 grams of water can be mixed with from about 0.5 grams to about 7 grams of ammonium nitrate, such as from about 0.6 grams to about 6 grams of ammonium nitrate, such as from about 0.7 grams to about 5 grams of ammonium nitrate. In one particular embodiment, 1.4 grams of water and 2.1 grams of ammonium nitrate can be used to remove about 6 Watts of energy from the tissue and probe 100F. The water and ammonium nitrate can be stored in a cartridge that can be inserted into the lumen 124 of the probe 100F just prior to use, or the water can be introduced into water channel 148 via tubing, such as tubing 151 that can deliver water from water source 150 into water channel 148, while the ammonium nitrate can be stored in its channel 149, which can surround the water channel 148 as shown in FIG. 3F. In addition, it is to be understood that the two materials (e.g., water and ammonium nitrate) can be located on any suitable surface or within any component of the electrosurgical device so long as the two materials, upon mixing, are in communication with a thermally conductive region of the probe in order to facilitate cooling of the probe 100F. For example, the two materials (e.g., water and ammonium nitrate) can be positioned on an exterior surface of the probe 100F, an introducer (see introducer 604 in FIG. 6), or a combination thereof.

Regardless of the particular combination of heat transfer materials and heat sink materials utilized, according to an aspect of the invention, it is desirable to absorb or remove thermal energy from the distal region of the probe over a period of time that corresponds to the length of an electrosurgical procedure in order to transfer heat away from a region of tissue. Generally speaking, it is desirable to absorb or remove from about 0.1 Watts to about 50 Watts of energy from the distal region of the probe to transfer heat away from area of tissue over a time period that may range from about 60 seconds to about 300 seconds. For example, it is desirable to absorb or remove from about 1 Watt to about 25 Watts of energy from the distal region of the probe to transfer heat away from area of tissue over a time period that may range from about 90 seconds to about 240 seconds. As another example, it is desirable to absorb or remove from about 2 Watt to about 15 Watts of energy from the distal region of the probe to transfer heat away from area of tissue over a time period that may range from about 100 seconds to about 200 seconds. As yet another example, it is desirable to absorb or remove from about 2 Watt to about 12 Watts of energy from the distal region of the probe to transfer heat away from area of tissue over a time period that may range from about 125 seconds to about 175 seconds. In one particular embodiment, the heat transfer system can remove from about 2 Watts to about 12 Watts of energy over about 150 seconds.

In some embodiments, any of the probes 100A-F discussed above can be sterilizable. The probe 100 can be sterilized by, for example, steam, ethylene oxide, or radiation sterilization without risk of material degradation or discoloration. In order for the probe 100 to be sterilizable, the probe 100 can be made from sterilizable materials. For instance, the shaft 122 can be made from stainless steel and the electrically insulative coating 116 may be made from PTFE.

Figure 4A:
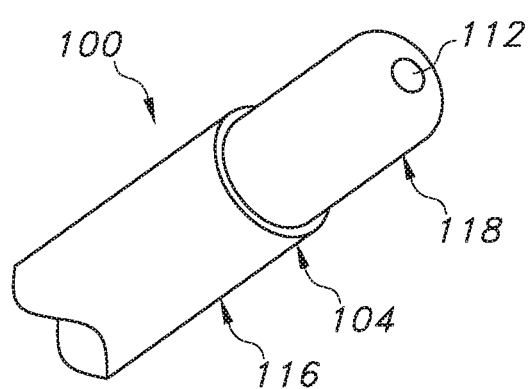
FIGS. 4A to 4C are partial perspective views showing configurations of temperature measuring devices that can be used in several embodiments of the present invention.
Figure 4B:
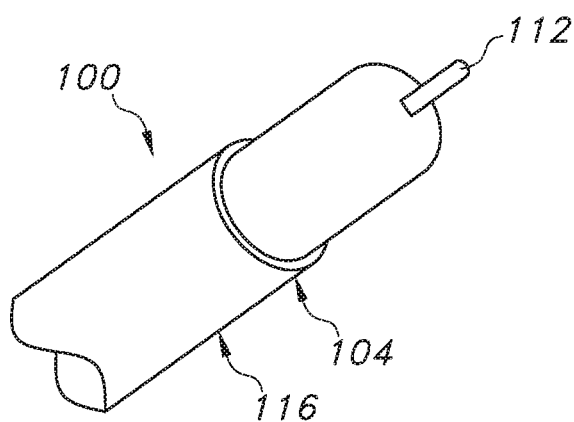
Figure 4C:
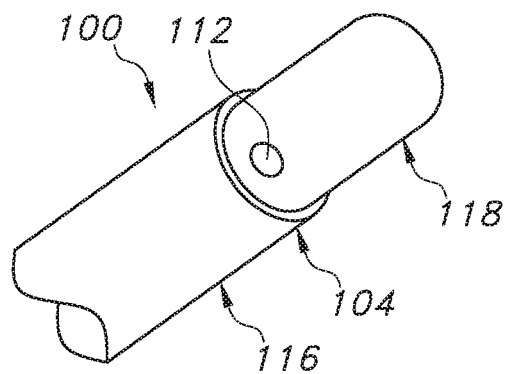

In some embodiments, the probe 100 can include at least one temperature sensing device 112 (i.e., a temperature sensor), as shown in FIGS. 1A-1B, 3A-3F, 4A-4C, and 6. The temperature sensing device 112 can be any means for sensing and/or measuring temperature, including, but not limited to, a thermocouple, a thermistor, an optical fluorescence sensor, or a resistance thermometer. In some embodiments, the temperature sensing device 112 can be positioned at the distal region 104 of the probe 100, for example at distal end 106. As shown in the embodiments of FIGS. 4A to 4C, the temperature sensing device 112 can have various configurations. For example, as shown in FIG. 4A, the temperature sensing device 112 can be disposed at the distal end 106 and can be substantially flush with the distal end 106. In another embodiment, as shown in FIG. 4B, the temperature sensing device 112 can protrude from the distal end 106, such that it may measure the temperature of a material that is located distal to distal end 106, rather than the temperature of the probe 100 itself or of material adjacent to the probe 100. In another embodiment, as shown in FIG. 4C, the temperature sensing device 112 can be located proximally to the distal end 106. In further embodiments, the probe 100 can include additional temperature sensing devices. For example, a first temperature sensing device may be located at the distal end 106 of the probe 100, and a second temperature sensing device may be located distal to the distal end 106 of the probe 100, such that the temperature at the distal end 106 of the probe 100 as well as in the tissue may be measured. In other embodiments, other configurations are possible, and the invention is not limited in this regard. Furthermore, in the embodiments shown in FIGS. 4A and 4C, the temperature sensing device may be located within the probe 100, or on the external surface of the probe 100.

In an alternate embodiment, the temperature sensing device 112 can be located within the lumen 124 of the probe 100 so as to measure the temperature of one or more components of a cooling/heat transfer system contained therein. By monitoring the change in temperature of the cooling fluid, which relates to the amount of heat being drawn away from the probe 100, the temperature of the tissue located adjacent conductive portion 118 can be determined.

In some embodiments, the probe 100 can include means for operatively connecting the temperature sensing device 112 to an external device. For example, such a device can be a display or screen, such that the temperature measured by the temperature sensing device may be viewed by a user. In other embodiments, the external device can be an electrical generator, such that temperature feedback can be provided to the electrical generator. Means for operatively connecting the temperature sensing device 112 to an external device can include an insulated wire 128, which can extend proximally from the temperature sensing device 112, through the lumen 124 of the probe 100, and out of the probe 100 through its proximal end 110. The wire 128 can be any temperature or electrical conductor capable of operatively connecting the temperature sensing device 112 to an external device. Alternatively, the temperature sensing device 112 can be operatively connected to an external device via a wireless connecting means, including, for example, infrared or Bluetooth™. Further details regarding temperature sensing devices can be found in U.S. Patent Application Publication No. 2005/0177209 to Leung, et al., which is incorporated herein by reference.

In some embodiments, the probe 100 can include a sensor for measuring impedance. As the impedance of a tissue may be a characterizing factor, measuring the impedance of tissue proximal to the probe 100 can help confirm placement within a desired tissue type. In some embodiments, the probe 100 can be structured to measure the electrical impedance between, for example, two points on the probe 100 or between a point on the conductive portion 118 and a point on an auxiliary device such as a cannula or a grounding pad. Further details regarding impedance measuring means may be found in U.S. Patent Application Publication 2005/0177209 to Leung, et al., which is incorporated herein by reference.

In some embodiments, the probe 100 can include a sensor for measuring pressure. The means of measuring pressure can include a lumen in fluid communication with fluid in a patient's body as well as with a pressure transducer to record the pressure measurements. In other embodiments, the pressure sensor can include a pressure transducer disposed at a desired location on the probe 100.

As mentioned above with respect to the temperature sensing device, the probe 100 can include means for operatively connecting any impedance or pressure measuring means to an external device. For example, a pressure transducer may be electrically coupled to a wire located within the probe 100, which wire may be further electrically coupled to an external device to transmit a signal from the pressure transducer to the external device.

In some embodiments, probe 100 can include means for enhancing the visualization thereof, for example when viewed under fluoroscopic imaging or another imaging modality. Such means may be a visible marker, a radiopaque marker or markers for use with magnetic resonance imaging or ultrasound, for example. Further details regarding enhanced visualization are disclosed in U.S. Pat. No. 7,593,778 to Chandran, et al. and U.S. Patent Application Publication 2004/0176759 to Krishnamurthy, et al., both of which are incorporated herein by reference.

In some embodiments, the hub 114 can have markings to indicate, for example, the direction/orientation of a bend or curve of the probe 100 or the location of an aperture or a temperature or pressure sensing device on or within the probe 100. These markings may be visual indicators, or tactile indicators, which may be textured or raised so that the user may see or feel the markings while manipulating the probe 100.

In some embodiments, a proximal end of the probe 100 can include a strain relief, which can additionally include a grip running from the proximal end to the distal end of the strain relief. A strain relief can be, for example, a soft flexible bend relief able to support any cable or tubing exiting the proximal end of the probe 100.

As mentioned hereinabove, the size and/or geometry of electrically insulating region 116 and the conductive portion 118 may differ depending on the specific application. As disclosed in U.S. Patent Application Publication No. 2007/0156136 to Godara, et al. and U.S. Pat. No. 7,819,869 to Godara, et al., which are incorporated herein by reference, when sufficient energy is delivered from an energy source through an active electrode to a tissue of a patient's body, a lesion may form in the tissue wherein the size, shape, and location of the lesion are at least partially dependent on the size and/or geometry of the active electrode.

Figure 5A:
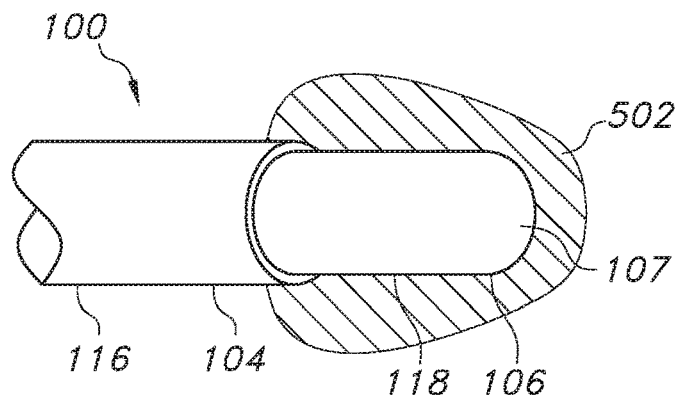
FIGS. 5A to 5D are partial perspective views showing embodiments of a distal region of a probe that can be used in the system contemplated by the present invention and examples of lesions formed therefrom.

Exemplary embodiments of probes 100 having a conductive portion 118 of various geometries, and being of between about 16 AWG and about 19 AWG, and examples of lesions 502 that may be formed therefrom are illustrated in FIGS. 5A to 5D, by way of non-limiting example only. Referring first to FIG. 5A, when conductive portion 118 of probe 100 is elongate, for example having a length of between about 4 mm and about 6 mm a substantially oblate lesion 502 may form around conductive portion 118. Due to edge effects, the distribution of energy may not be equal around all portions of the conductive portion 118, and a large portion of the current may exit the conductive portion 118 in the region closest to the electrically insulated portion 116. Thus, the widest portion of the lesion may form in the area adjacent the electrically insulated portion 116. In use, such a conductive portion may be positioned such that it lies substantially parallel to the surface of the tissue to be lesioned (target site) in order to provide maximum efficacy.

Figure 5B:
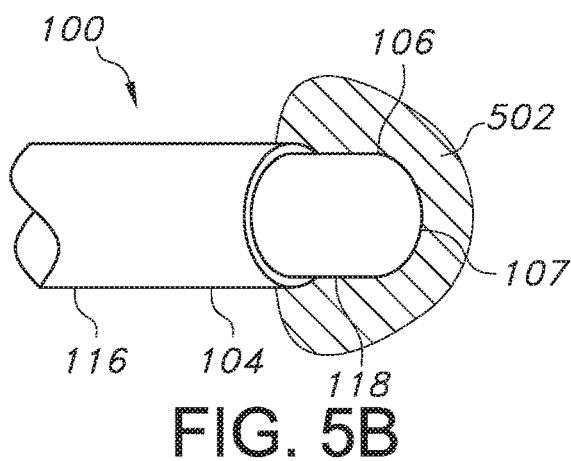

Referring now to FIG. 5B, when the electrically conductive portion 118 of the probe 100 is shortened and, for example, has a length of between about 2 mm and about 4 mm, a substantially more rounded lesion 502 may form around the conductive portion 118. Due to the shorter length of the conductive portion 118, the lesion 502 may extend distally further from the probe 100 than the lesion shown in FIG. 5A.

Figure 5C:
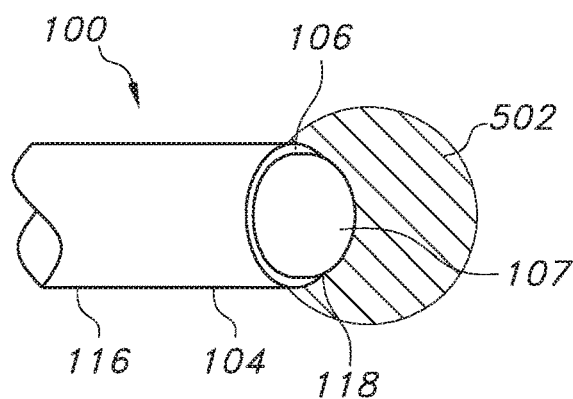
Figure 5D:
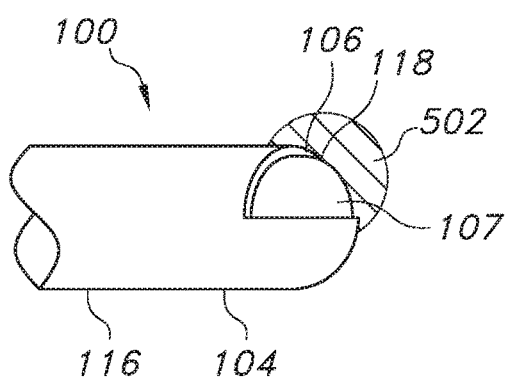
Figure 15:
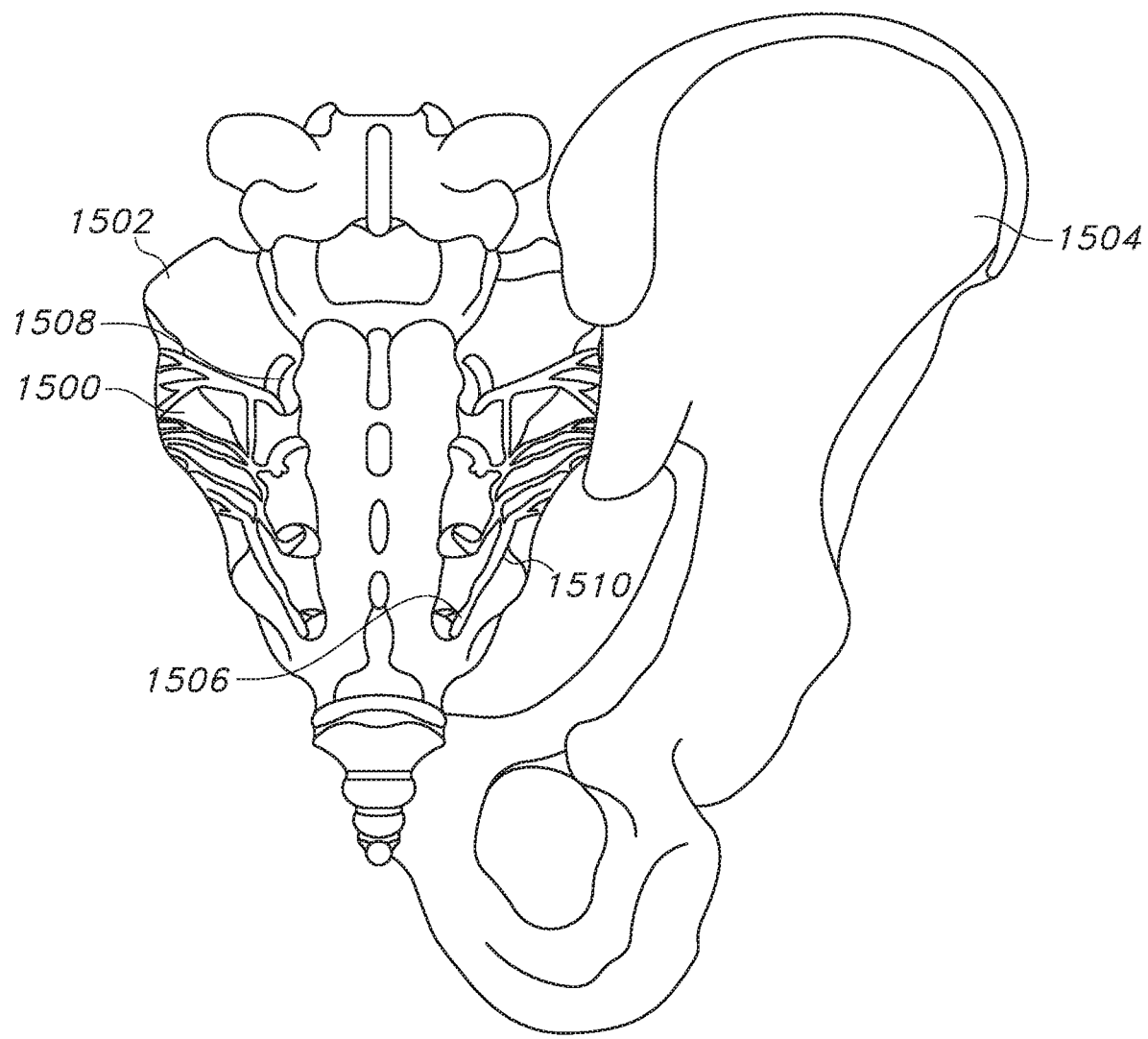
FIG. 15 shows a plan view of the sacroiliac region of a human.
Figure 16A:
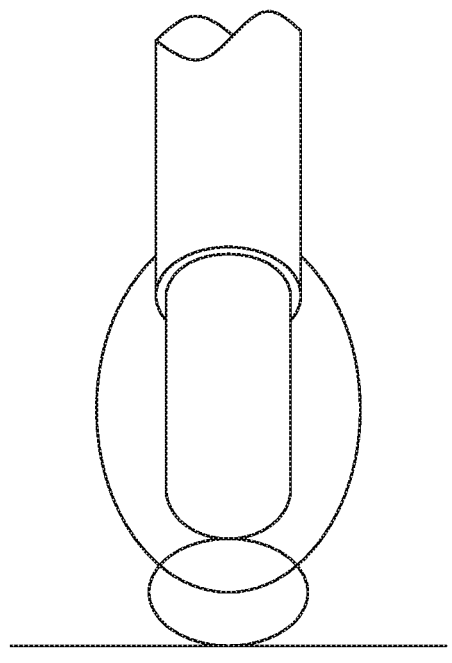
FIGS. 16A-16C show a lesion as would be formed by a probe of the prior art.
Figure 16B:
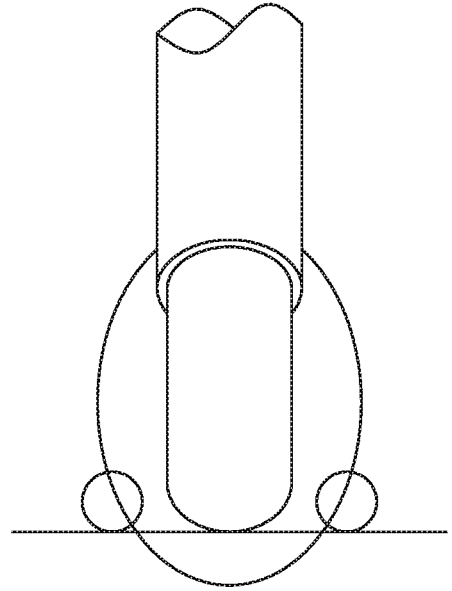
Figure 16C:
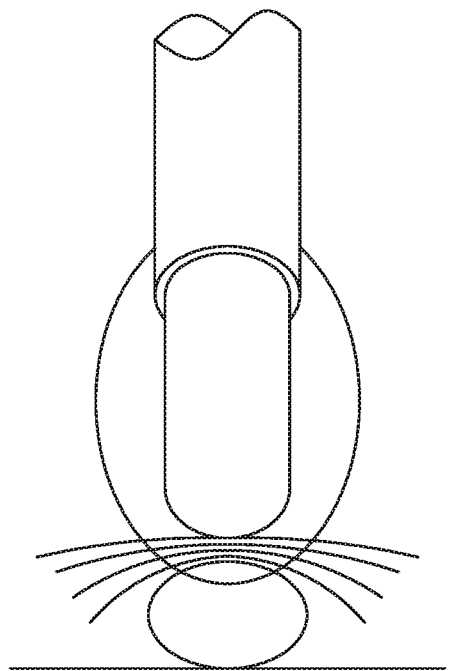

In some embodiments, the electrically insulated portion may extend substantially from the proximal region 108 of the probe 100 to the distal end of probe 100. For example, the electrically insulated portion 116 may terminate at the distal face of the probe such that the distal face 107 of the probe 100 includes at least one electrically exposed conductive portion 118. As will be apparent to the person skilled in the art, depending upon the geometry of the probe, the electrically insulated portion may terminate slightly proximal to the distal face so long as the energy delivery remains substantially distal. In some embodiments, a portion of the distal face 107 can include at least one conductive portion 118 as shown, for example, in FIGS. 2B-2D. Referring now to FIG. 5C, a probe 100 having a distal face 107 that includes electrically exposed conductive portion 118 is shown. In such embodiments, if distal face 107 is rounded (as shown in FIG. 5C), the rounded face or surface can include the conductive portion 118; if the distal face 107 is flat, the flat surface can include the conductive portion 118, and so on. In these embodiments, a lesion 502 may form wherein the lesion forms substantially distal to the distal face 107, for example, such that the majority of the lesion 502 is located distal to the distal face 107 of the probe 100, and the shape of the lesion 502 may be substantially rounded, for example the ratio of the length of the lesion 502 (i.e., the dimension along the longitudinal axis of the probe 100) to the width of the lesion 502 (i.e., the dimension perpendicular to the longitudinal axis of the probe 100) may be about 1:1. In use, such a probe 100 may be positioned such that it is oriented substantially perpendicular or generally upstanding to the target site or surface of the tissue to be lesioned (i.e., such that the tissue to be lesioned is generally distal to the probe 100, whereby the lesion 502 may extend distally from the probe 100 to the target tissue. This can provide significant advantages in a region of the body such as the sacroiliac region (shown in FIG. 15) having a rough or uneven surface, because the conductive portion 118 can be positioned to lesion tissue disposed in rifts and valleys between bony structures, or in fissures or grooves in the surface of a bony structure, as is described in detail below. In further embodiments, the conductive portion 118 may be offset from an axis of the probe 100 such that the electrically exposed conductive portion 118 is not symmetrical about the axis of the probe 100, as shown for example in FIG. 5D.

In some embodiments, the probe 100 may be structured to have a conductive portion 118 of a fixed size. In other embodiments, the size of the conductive portion 118 may be adjustable. For example, in one embodiment, wherein the probe 100 includes a conductive shaft 122 with an electrically insulative sheath or coating 116 disposed thereon, the electrically insulative sheath 116 may be structured such that it may be slid or otherwise moved distally or proximally along the shaft 122. Thus, when the electrically insulative sheath 116 is moved proximally along the shaft 122, the electrically exposed portion 118, or active electrode, would become longer. When the electrically insulative coating 116 is moved distally on the shaft 122, the active electrode 118 would become shorter. As mentioned above, altering the length of the active electrode 118 may affect the geometry of a lesion formed therefrom. In some embodiments, the length of the active electrode 118 may be modified before, during or after a treatment procedure while, in other embodiments, the length of the active electrode 118 may not be modified during the actual course of the procedure. For example, in one such embodiment, the probe 100 may have a safety mechanism, for example a stopping means such as a clamp, to prevent movement of an insulative sheath 116 during the course of a treatment procedure.

In another alternate embodiment of the present invention, a treatment apparatus can include an introducer 604 (see FIG. 6) in addition to a probe. The introducer may be used to deliver energy to the patient's body, as will presently be described, and/or the introducer may be used to facilitate insertion of the probe, as will be described below. In embodiments wherein the introducer is used to deliver energy, the introducer can include at least one electrically exposed conductive portion and at least one electrically insulated portion. In some embodiments, the body of the introducer may be constructed from a conductive material, which is at least partially overlain with an insulating sheath or coating, defining the insulating region; however, in some embodiments, the introducer may be constructed from an insulating material with one or more conductive bodies or electrodes applied externally. The distal end of the introducer may be pointed or sharp. For example, the distal end of the introducer can include a bevel. In one embodiment, the at least one electrically insulated portion may extend from the proximal region of the introducer to the distal end of the introducer, such that the distal face of the introducer includes at least one exposed conductive portion. In embodiments comprising a bevel, the at least one exposed conductive portion can include the bevel. In alternate embodiments, the exposed conductive portion may, alternatively or in addition, be located on a side of the introducer. In some embodiments, the electrical insulation may extend to the heel of the bevel of the introducer, while in others, the insulation may end further proximally along the introducer.

In some embodiments, the introducer is straight, whereas in some other embodiments the introducer may be bent. For example, in some such embodiments, the introducer may have about a 5° to about a 20° bend in the distal region of the introducer. In some embodiments, the introducer may be between about 16 and about 18 AWG, between about 75 and about 150 mm in length, with the electrically exposed conductive portion about 2 mm to 6 mm in length. In these embodiments, the probe may be structured to be disposed within the lumen of the introducer and to be in electrical contact with the introducer when fully disposed within the introducer.

The probe can include an electrically conductive elongated shaft, a connecting means for connecting to an energy source, and a connecting means for connecting to a cooling supply, for example as described herein above. Thus, when energy is supplied by an energy source to the probe, the energy flows along a conductive portion of the introducer and is delivered to the target treatment site, traveling through the tissue or body to a reference or return electrode. In such embodiments, the shaft of the probe may be electrically conductive and exposed along substantially the entire length of the probe. In other words, a probe used in such an embodiment in conjunction with an introducer may not include an electrically insulative coating as described above.

In some embodiments, the distal end of the probe may be substantially flush with the distal end of the introducer when fully disposed in the introducer. In other embodiments, the distal end of the probe may extend distally from the distal end of the introducer when fully disposed in the introducer. In other embodiments, the distal end of the elongate member may be recessed proximally from the distal end of the introducer when fully disposed in the introducer. As used herein, the phrase "fully disposed" refers to a first member being substantially fully received within a second member such that, under normal use, it is not intended to be inserted into the second member any further.

The probe and the introducer may be structured such that when the probe is fully positioned inside or disposed within the introducer, at least a portion of the probe is in electrical and/or thermal contact with at least a portion of the introducer, such that thermal and/or electrical energy may be delivered from the probe to the introducer. This may be accomplished by flushing the introducer with a liquid such as saline prior to inserting the probe, such that a layer of liquid remains between at least a portion of the probe and the introducer. The saline may then serve to conduct electricity and/or heat between the probe and the introducer. Alternatively, the probe and introducer may be structured such that they are in physical contact when the probe is fully disposed within the introducer, thereby also being in electrical and thermal contact. In a further embodiment, a portion of the probe may be in thermal contact with the conductive portion of the introducer. This may be beneficial in that the cooling of the probe would allow for the conductive portion of the introducer to be cooled. The probe may be cooled by a variety of methods, as described above.

Embodiments comprising a cooled probe within an introducer may be advantageous in that pre-existing introducers may be used in conjunction with such embodiments of a cooled probe. Thus, these probe embodiments may allow for use of an introducer that is similar to those currently in use and familiar to practitioners, but which can be used to create larger lesions than presently possible due to the cooling supplied to the probe disposed within the introducer and which can deliver liquid to the target site without removal of the probe due to the arrangement of the T-joint including the liquid delivery side port, as described below with respect to FIGS. 20 and 21. In addition, practitioners may be familiar with a procedure involving positioning the distal region of an introducer at a target site, positioning a probe within the introducer, and delivering energy from the probe to the introducer, and from the introducer to the target site. Thus, a cooled probe of this embodiment, sized to be disposed within an introducer, would allow practitioners to follow a normal procedure with the added benefit of cooling, similar to what they have previously practiced using a similar introducer though without cooling. In still other embodiments, the side port can be part of the introducer itself, as described below with respect to FIGS. 17-18.

With reference now to FIG. 6, systems of the present invention can include one or more of: one or more probes 100; one or more introducer apparatuses 604; one or more obturator apparatuses 606; one or more dispersive return electrodes (not shown); one or more sources of cooling as discussed above; one or more energy sources, for example generators 608; and one or more connecting means, for example cables 612.

The introducer apparatus may aid in inserting the probe 100 into a patient's body. The introducer apparatus can include a hollow elongate introducer 604 and an obturator 606. In this embodiment, as mentioned above, the introducer 604 may be useful for facilitating insertion of the device into the patient's body. For example, the introducer 604 and/or the obturator 606 may be substantially stiff or rigid, such that the introducer apparatus may assist in piercing skin or other body tissues. The obturator 606 may be structured to cooperatively engage the introducer 604. In other words, the obturator 606 may be sized to fit within the lumen of the introducer 604 and can include means for securing the obturator 606 to the introducer 604. In one embodiment, when the obturator 606 is fully disposed within the introducer 604, the obturator 606 sufficiently occludes the lumen of the introducer 604 such that tissue is prevented from entering the lumen when the introducer apparatus is inserted into the body. In some embodiments the distal end of the obturator 606 may be sharp or pointed. In these embodiments, the distal end of the obturator 606 may be conical, beveled, or, more specifically, tri-beveled. The lengths of the obturator 606 and the introducer 604 may vary depending on the application. In one embodiment, the introducer 604 may be sized such that its distal end can reach the target tissue within the body while the proximal end remains outside of the body. In some embodiments, the introducer 604 can be between about 5.5 inches (13.97 cm) and about 7.5 inches (19.05 cm) in length, and obturator 606 may be between about 5.5 inches (13.97 cm) and about 7.5 inches (19.05 cm) in length. More specifically, the introducer 604 may be about 6.4 inches (16.26 cm) in length, and the obturator 606 may be about 6.6 inches (16.76 cm) in length. The obturator 606 may be slightly longer than the introducer 604, so that the distal end of the obturator 606 may protrude from the introducer 604 when fully disposed. In some embodiments, obturator 606 may be substantially longer than the introducer 604, and may be visible under fluoroscopy, such that it may aid in visualizing the location of lesion formation when a cooled probe is used. Further details regarding this embodiment are disclosed in U.S. Patent Application Publication No. 2009/0024124 to Lefler, et al., which is incorporated herein by reference. The lumen of the introducer 604 can also be sized to accommodate the diameter of the probe 100, while remaining as small as possible in order to limit the invasiveness of the procedure. In a specific embodiment, the proximal regions of the introducer 604 and the obturator 606 are structured to be locked together with a hub or lock.

In one embodiment, introducer 604 and the obturator 606 can be made from stainless steel. In other embodiments, the introducer 604, the obturator 606, or both may be made from other materials, such as nickel-titanium alloys for example. Furthermore, in some embodiments, the obturator 606 can include a means for connecting the obturator 606 to the generator 608, for example a wire or cable. In such embodiments, the obturator 606 may be operable to measure the impedance of tissue as the introducer apparatus is inserted into the patient's body. In addition or alternatively, the obturator 606 may be operable to deliver stimulation energy to a target tissue site, as described further herein below.

In some embodiments, the probe 100 may be structured to be operatively connected to an energy source 608, for example a generator 608. The connecting means 612 for connecting the probe 100 to the generator 608 can include any component, device, or apparatus operable to make one or more electrical connections, for example an insulated wire or cable. In one embodiment, the connecting means 612 can include an electrical cable terminating at the hub 114 as well as a connector at a proximal end thereof. The connector may be operable to couple to the energy source 608 directly or indirectly, for example via an intermediate cable. At least one wire or other electrical conductor associated with the cable 612 may be coupled to a conductive portion of the shaft 122, for example by a crimp or solder connection, in order to supply energy from the energy source 608 to the shaft 122. In one specific embodiment, a 4-pin medical connector may be used to connect the cable 612 to an intermediate cable (not shown), which may be further attached to a 14-pin connector capable of being automatically identified when connected to the generator 608.

The generator 608 may produce various types of energy, for example microwave, ultrasonic, optical, or radio-frequency electrical energy. In some embodiments, generator 608 may produce radiofrequency electrical current, having a frequency of between about 10 kHz and about 1000 kHz, at a power of between about 1 Watts and about 50 Watts. In some embodiments, the generator 608 can include a display means incorporated therein. The display means may be operable to display various aspects of a treatment procedure, including but not limited to any parameters that are relevant to a treatment procedure, such as temperature, power or impedance, and errors or warnings related to a treatment procedure. Alternatively, the generator 608 can include means for transmitting a signal to an external display. In one embodiment, the generator 608 may be operable to communicate with one or more devices, for example with one or more probes 100 and/or one or more sources of cooling, for example pumps 610. Such communication may be unidirectional or bidirectional depending on the devices used and the procedure performed. An example of an RF generator that may be used as part of a system of the present invention is the Pain Management Generator (PMG) of Baylis Medical Company Inc. (Montreal, QC, Canada). Further details regarding embodiments of energy sources are disclosed in U.S. Pat. No. 8,882,755 to Leung, et al. and U.S. Pat. No. 7,258,688 to Shah, et al., both of which are previously incorporated herein by reference.

As an example of communication between the generator 608 and other devices in a system of the present invention, the generator 608 may receive temperature measurements from one or more temperature sensing devices 112. Based on the temperature measurements, the generator 608 may perform some action, such as modulating the power that is sent to the probe(s). For example, power to the probe(s) could be increased when a temperature measurement is low or decreased when a measurement is high, relative to a predefined threshold level. If more than one probe is used, the generator may be operable to independently control the power sent to each probe depending on the individual temperature measurements received from the temperature sensing devices associated with each probe. In some cases, the generator 608 may terminate power to one or more probe(s) 100. Thus, in some embodiments, the generator 608 may receive a signal (e.g., temperature measurement) from one or more probe(s), determine the appropriate action, and send a signal (e.g., decreased or increased power) back to one or more probe(s). In addition, when using more than one probe 100, in embodiments where the generator 608 does not control each of the probes 100 independently, the average temperature or a maximum temperature in the temperature sensing devices 112 associated with probe(s) 100 may be used to control the cooling means.

In some embodiments, systems of the present invention can include one probe; in other embodiments, systems of the present invention can include a plurality of, for example two, probes. The system may be operated, for example, in a monopolar mode, a bipolar mode, or a multiphasic/multipolar mode. When operated in a monopolar mode, any number of probes may be used, and the system may further include a dispersive return electrode. The dispersive return electrode may be, for example, a grounding pad for attaching to the patient's skin, or may be a substantially large electrode that is integral with the probe 100. When the system is operated in a bipolar mode, any number of probes, for example two probes, may be used, and current may travel between the probes. Alternatively, when one probe is used, current may travel between a conductive portion 118 and a second electrically conductive and exposed portion on the probe 100. For example, the probe 100 can include a second electrically conductive and exposed portion in the form of a ring that is disposed around probe 100 at a location proximal to the conductive portion 118. The conductive portion 118 and the second electrically conductive and exposed portion may be electrically isolated from each other, and the probe 100 can include means for operatively connecting the second electrically conductive and exposed portion to a source of energy which is at a different electrical potential than the electrode 118, or to a circuit ground.

The operation of the system may be manually controlled by a user, or may be automatically controlled based on certain parameters, for example, based on a measurement of a property of a component of is the system itself or of a property of the tissue being treated. When more than one probe is used, means of controlling the operation of the system may be configured to independently control each probe such that, for example, current flow to any of the probes may be independently adjustable. In embodiments of a system having automatic control, the system can include a controller operable to control one or more devices based on specified criteria. Further details regarding automatic or manual control of the system are provided in U.S. Pat. No. 8,882,755 to Leung, et al.

Figure 17:
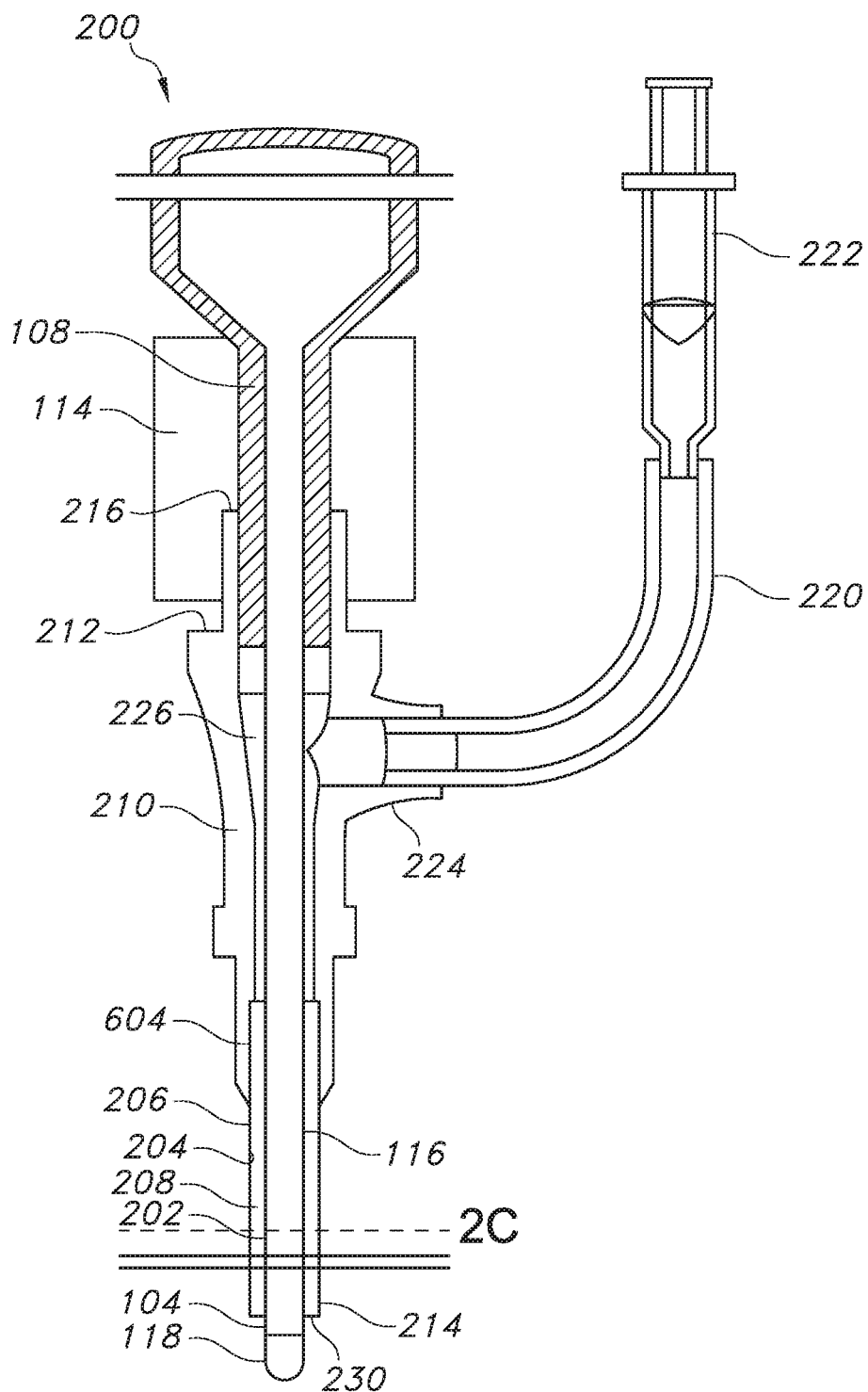
FIG. 17 illustrates a cross-sectional view of a system contemplated by the present invention that includes a probe and an introducer with a side port for liquid delivery to a lesion site.
Figure 18:
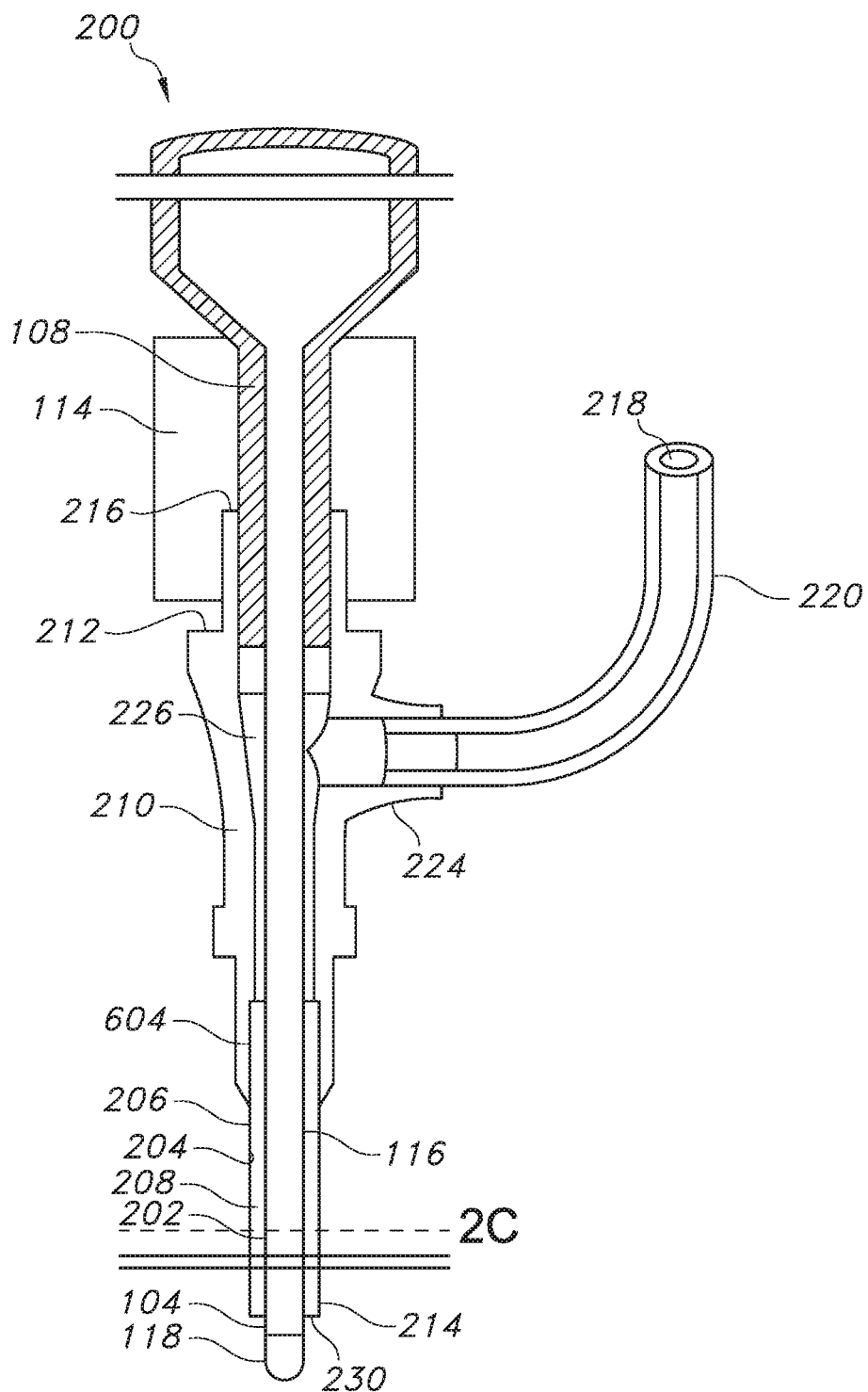
FIG. 18 illustrates a cross-sectional view of a system contemplated by the present invention that includes a probe and an introducer with a side port for venting during treatment (e.g., lesioning)
Figure 19:
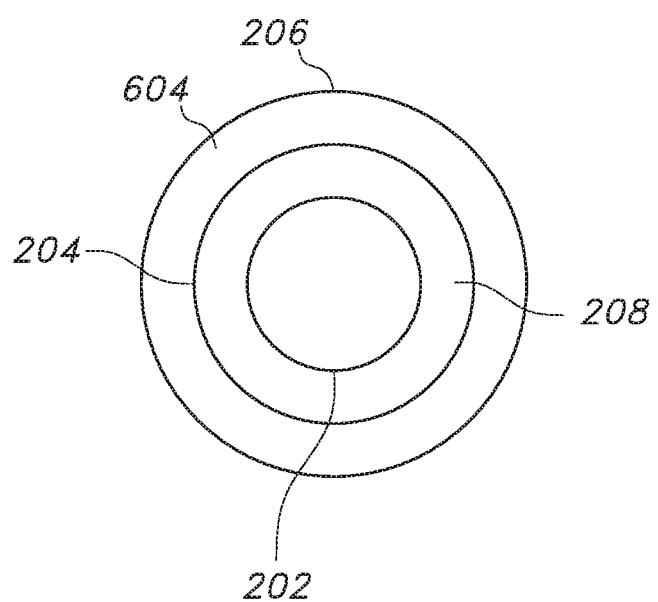
FIG. 19 illustrates a cross-sectional view at point 2C of FIG. 17 showing the lumen created between the outer diameter of the probe and the inner diameter of the introducer.
Figure 20:
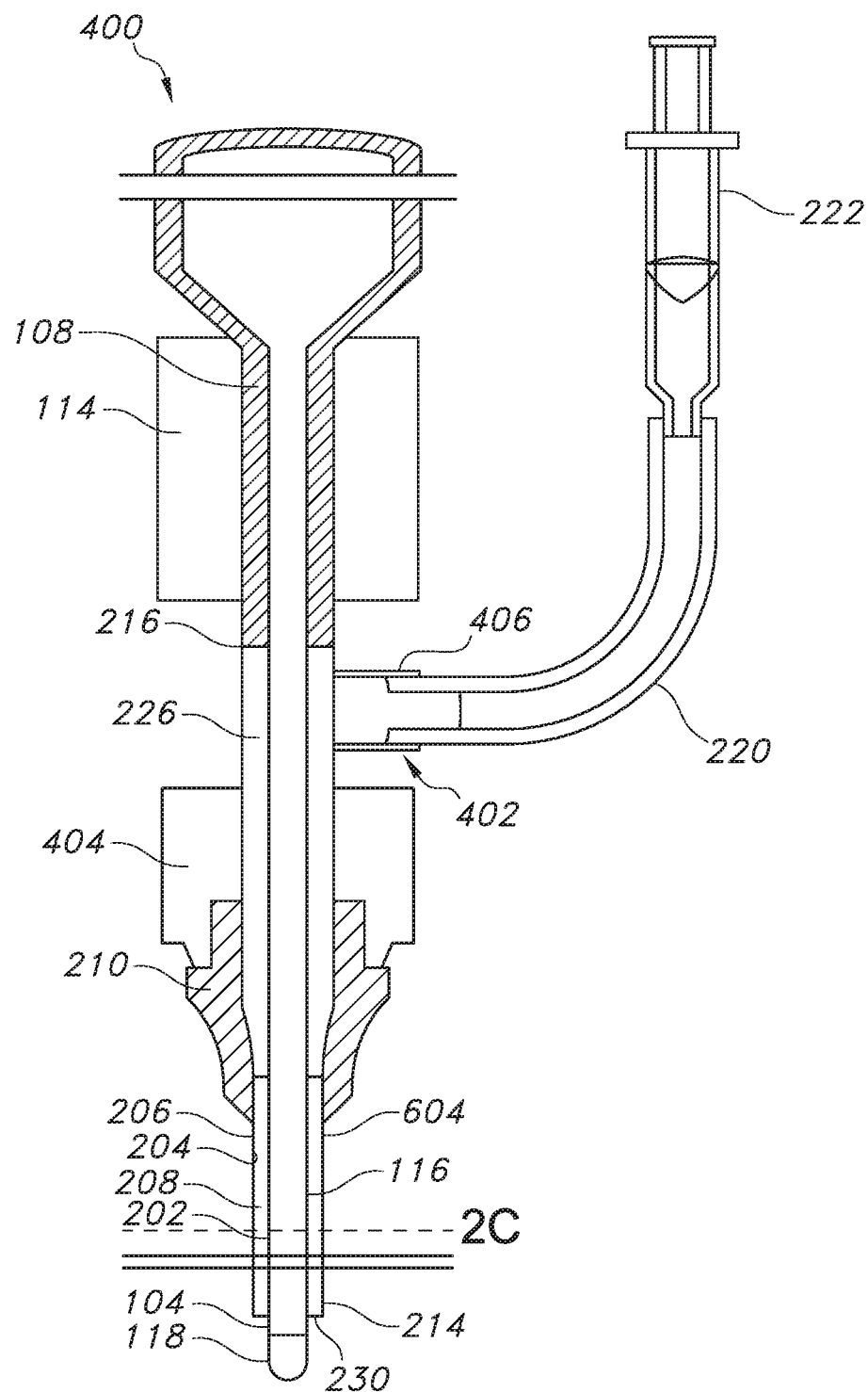
FIG. 20 illustrates a cross-sectional view of a system contemplated by the present invention that includes a probe and an introducer with a T-joint having a side port positioned there between for liquid delivery to a lesion site.
Figure 21:
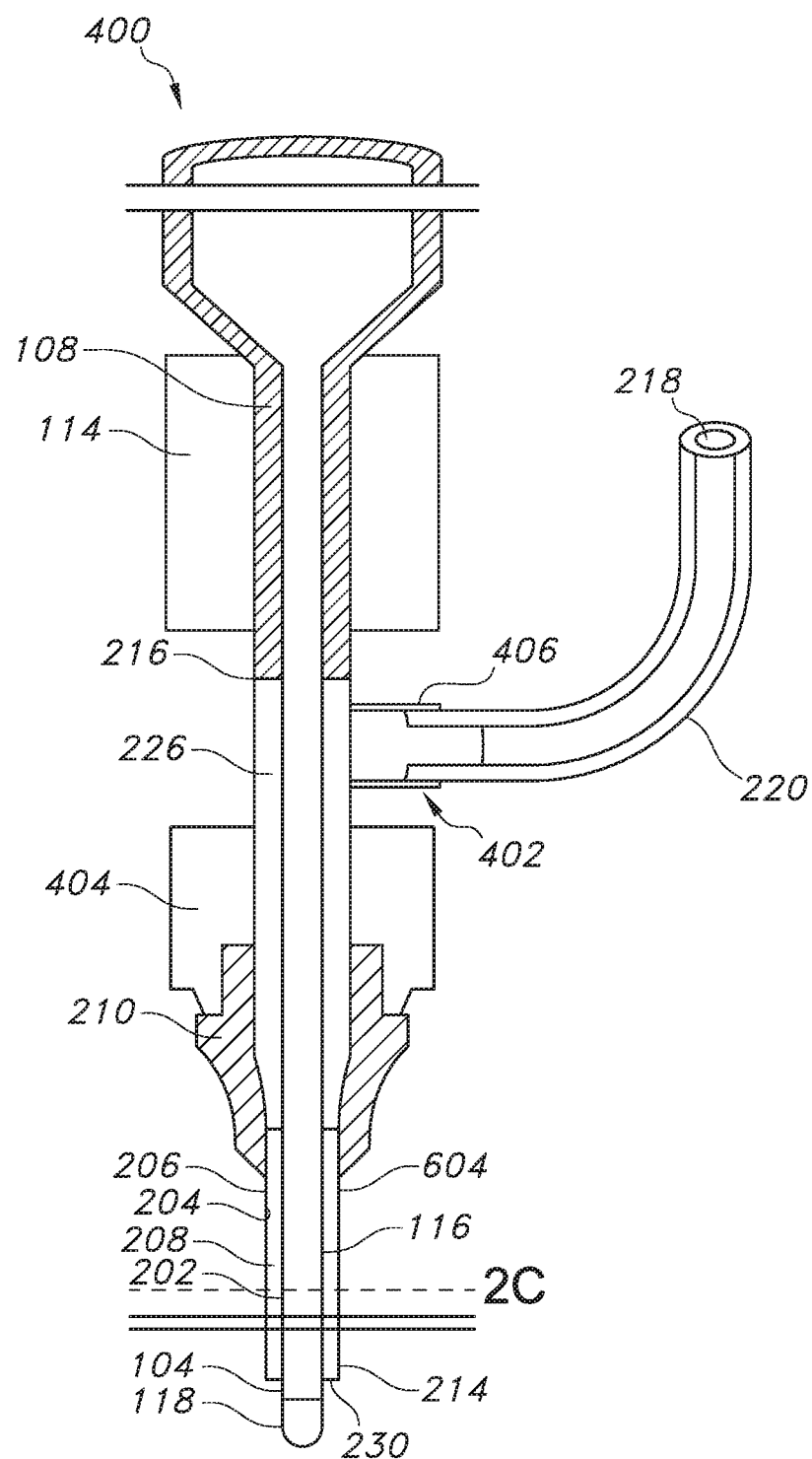
FIG. 21 illustrates a cross-sectional view of a system contemplated by the present invention that includes a probe and an introducer with a T-joint having a side port positioned there between for venting during treatment (e.g., lesioning).

Regardless of the various features described above and referring now to FIGS. 17 to 21, the electrosurgical device contemplated by the present invention can, in some embodiments, include a side port 224 or 406 for the introduction of liquid into a lumen 208 defined by an outer diameter 202 of the probe 100, 100A-F, 200, or 400 and an inner diameter 204 of the introducer 604 (also having an outer diameter 206) when the probe 100, 200, or 400 is positioned inside the introducer 604 such that a distal end 106 of the probe 100, 200, or 400 can contact a target site (e.g., the site near or adjacent tissue to be treated). FIG. 19 shows a cross-sectional view of the lumen 208 defined by the inner diameter 204 of the introducer 604 and the outer diameter 202 of the electrically insulated portion 116 of the probe 200 at cut line 2C. The side port can be connected to a syringe 222 or other suitable liquid introduction apparatus (e.g., an IV bag, etc.) via tubing 220 so that a liquid containing a therapeutic agent, saline, etc. can be injected into the lumen 208 and can exit the distal end 214 of the introducer 604 at or near the target site at liquid exit 230 to bathe an exposed conductive portion 118 of the probe 100, 200, or 400 and the surrounding tissue with the liquid. The side port 224 or 406 can be a component of the introducer hub 210 as shown in FIGS. 17 and 18 or can be disposed between the introducer 604 and the probe 200 as a component of a T-joint 402 as shown in FIGS. 20 and 21. Further, a seal 216 can be formed between the proximal region 108 of the probe 200 or 400 and the introducer hub 210 near the proximal end 212 of the introducer 604 or at the T-joint 402 to prevent the backflow of liquid from the side port 224 or 406 to the proximal region 108 of the probe 200 or 400. Additionally, the syringe 222 can be removed from the tubing 220 so that the tubing 220 can serve as a vent 218 at its open end during treatment with the electrosurgical device, which can, in addition to the cooled probe, reduce the temperature of tissue at the target site, thus minimizing tissue damage.

In one particular embodiment, as shown in FIGS. 17 and 18, the electrosurgical device includes a probe 200 and an introducer 604 that define a lumen 208 for the exit of liquid from the distal end 214 of the introducer 604 at liquid exit 230 to bathe an exposed conductive portion 118 of the probe 200 and the surrounding tissue (i.e., the target site) with a liquid-based therapeutic agent, saline, or any other suitable liquid. In order to prevent the back flow of liquid, a seal 216 is formed between a proximal region 108 of the probe 200 and a proximal end 212 of the introducer 604 at hub 114, which also locks the proximal region 108 of the probe 200 in place with respect to the introducer hub 210. The introducer hub 210 also defines a void 226 in which liquid can be injected from a syringe 222 or any other suitable liquid introduction device via tubing 220 that is connected to a side port 224 that is formed in the introducer hub 210. The liquid can then flow in the lumen 208 formed between the inner diameter 204 of the introducer 604 at its distal end 214 and the outer diameter 202 of the electrically insulated portion 116 of the probe 200. Such an arrangement prevents having to remove the probe 200 from the introducer 604 in order to inject a therapeutic agent or other suitable liquid to the target site or nearby tissue. Further, after the therapeutic agent or other suitable liquid has been delivered to the target site, the syringe 222 or other suitable liquid introduction device can be removed so that the resulting open end of the tubing 220 can serve as a vent 218 during treatment, which, in conjunction with probe 200 cooled via the means discussed above, can cool the tissue near the target site to minimize tissue damage.

In another particular embodiment, as shown in FIGS. 20 and 21, the electrosurgical device also includes a probe 400 and an introducer 604 that define a lumen 208 for the exit of liquid from the distal end 214 of the introducer 604 at liquid exit 230 to bathe and exposed conductive portion 118 of the probe 200 and the surrounding tissue (i.e., the target site) with a liquid-based therapeutic agent, saline, or any other suitable liquid. In order to prevent the back flow of liquid, a seal 216 is formed between a proximal region 108 of the probe 200 and a T-joint 402, where a hub 114 locks the proximal region 108 of the probe 200 in place with respect to T-joint 402. The T-joint 402 also defines a void 226 in which liquid can be injected from a syringe 222 or any other suitable liquid introduction device via tubing 220 that is connected to a side port 406 that is formed in the T-joint 402. The liquid can then flow in the lumen 208 formed between the inner diameter 204 of the introducer 604 at its distal end 214 and the outer diameter 202 of the electrically insulated portion 116 of the probe 200, where the introduce 604 is secured to the T-joint 402 via a hub 404. Such an arrangement prevents having to remove the probe 200 from the introducer 604 in order to inject a therapeutic agent or other suitable liquid to the target site or nearby tissue. Further, as with the embodiment discussed above with respect to FIGS. 17 and 18, after the therapeutic agent or other suitable liquid has been delivered to the target site, the syringe 222 or other suitable liquid introduction device can be removed so that the resulting open end of the tubing 220 can serve as a vent 218 during treatment, which, in conjunction with probe 200 cooled via the means discussed above, can cool the tissue near the target site to minimize tissue damage.

Generally speaking, the lumen 208 defined by an outer diameter 202 of the probe 100, 200, or 400 and an inner diameter 204 of the introducer 604 (also having an outer diameter 206) when the probe 100, 200, or 400 is positioned inside the introducer 604 may have a cross-section perpendicular to a longitudinal axis in the form of an annular ring defining a space having a thickness or width of from about 0.00175 inches (0.045 millimeters) to about 0.003 inches (0.076 millimeters). Desirably, this thickness or width may be from about 0.002 inches (0.051 millimeters) to about 0.00285 inches (0.072 millimeters). More desirably, this thickness or width may be from about 0.0025 inches (0.064 millimeters) to about 0.00275 inches (0.07 millimeters).

While the volume of liquid that may be delivered to the target site over a time period of about 30 seconds may be up to about 2 milliliters, more desirably, the volume of liquid delivered to the target site over a time period of about 30 seconds ranges from about 0.05 milliliters to about 0.75 milliliters. Even more desirably, the volume of liquid delivered to the target site over a time period of about 30 seconds ranges from about 0.1 milliliters to about 0.5 milliliters. For example, the volume of liquid delivered to the target site over a time period of about 30 seconds may be about 0.25 milliliters to about 0.35 milliliters delivered to the target site over about 30 seconds. These values generally apply to delivery of liquids having a viscosity of ranging from about 0.75 centipoise to about 3 centipoise (e.g., about 1 centipoise) at room temperature (e.g., about 20° C.).

The lumen 208 may be sized to accommodate a liquid delivery rate of from about 0.001667 milliliters per second to about 0.0667 milliliters per second without creating significant pressure build-up or flow restrictions. When the liquid delivery flow rate is divided by the cross-sectional area of the lumen (e.g., fluid delivery channel), the result is a liquid velocity. For example, the lumen 208 may provide a liquid velocity of from about 14 inches per minute to about 436 inches per minute or from about 0.23 inches per second to about 7.3 inches per second, which corresponds to a liquid velocity of from about 5.8 mm/sec to about 185 mm/sec. Desirably, the liquid velocity may be from about 25 mm/sec to about 85 mm/sec.

Having a ratio of liquid delivery flow rate to cross-sectional area in this range can be advantageous for lumen cross-sectional areas in the range of about 0.0001 square inch (0.065 mm$^2$) to 0.0003 square inch (0.194 mm$^2$) because it is important to minimize the cross sectional area of the lumen in order to maximize the outer diameter of the probe 100 without interfering with liquid delivery through the lumen 208 defined by an outer diameter 202 of the probe 100, 200, or 400 and an inner diameter 204 of the introducer 604. This configuration is particularly advantageous for cooled probes because the overall diameter of the probe and introducer combination can be reduced while still allowing liquid delivery because it eliminates the need for a separate lumen or channel that extends internally through the probe to an aperture at the distal end or region of the probe to provide for liquid delivery.

In general, embodiments of a method of the present invention involve using a treatment device, for example a probe, in a particular region of a patient's body to form a lesion of sufficient size and suitable geometry to effectively treat the target tissue. For example, in one broad aspect, a method is provided for creating a lesion at a target site within a body of a human or animal using an electrosurgical device having a longitudinal axis.

The desired size and geometry of the lesion may depend on the specific anatomy and tissue being targeted and may be affected by several parameters as described herein, including but not limited to the geometry of the treatment device and the amount of cooling delivered to the treatment device. Thus, in accordance with one aspect of the present invention, steps are provided for creating a lesion with desired characteristics during the course of an electrosurgical procedure. The lesion may function to inhibit neural activity, for example nociception. Alternatively, in some embodiments, the lesion may have other effects, for example the shrinkage of collagen. Method embodiments of the present invention can generally include one or more of the steps of: determining a desired lesion shape, size, and location; selecting an electrosurgical instrument or device, for example a probe, and energy delivery parameters, for example voltage, based on the desired lesion shape, size, and location; inserting the electrosurgical instrument or device into a patient's body; positioning the electrosurgical instrument or device at a target site; delivering energy, for example radiofrequency current, through the electrosurgical instrument or device to the target site to form a lesion; and applying cooling to the electrosurgical instrument or device. As will presently be discussed, embodiments of the method aspect of the present invention may be useful, for example, to allow for more straightforward device placement during electrosurgical procedures than is presently possible.

In one embodiment of the method aspect of the present invention, the step of inserting an electrosurgical instrument or device can include inserting a probe percutaneously into a patient's body, and the step of positioning an electrosurgical instrument or device can include advancing the electrosurgical instrument or device until the active electrode is at or in the vicinity of a target treatment site. The step of inserting a probe may optionally be preceded by one or more additional steps including, for example, inserting an introducer apparatus into the body in the vicinity of the target treatment site, measuring one or more properties of a device or of tissue at or near the target treatment site, inserting or removing material at or near the target treatment site, and performing another treatment procedure at or near the target treatment site.

As described above, in some embodiments, the probe may be used in conjunction with an introducer apparatus, which can include an introducer and an obturator, for example. In use, the obturator may be initially disposed within a lumen of the introducer to facilitate insertion of the introducer apparatus to the target treatment site. Once the introducer apparatus has been properly positioned, the obturator may be removed and replaced within the introducer lumen by the probe. In some embodiments, as described further herein below, the obturator may be operable to measure the impedance of tissue as the introducer apparatus is inserted into the patient's body, which may assist in positioning the introducer apparatus at the target site. Alternatively or in addition, the obturator may be operable to deliver stimulation energy to the target treatment site, as described below. The probe and introducer may be structured such that when the probe is fully disposed within the introducer, the distal end of the probe may be aligned with the distal end of the introducer. In other embodiments, the probe and the introducer may be structured such that when the probe is fully disposed within the introducer the distal end of the probe protrudes or extends from the distal end of the introducer. For example, as described above, if the introducer includes an electrically conductive elongate member covered by electrically insulating material, with a distal portion that is electrically conductive and exposed, then the probe may be operable to deliver energy from an energy source to the conductive distal portion of the introducer. This delivery of energy may be facilitated by physical contact between the tip of the probe and the inner surface of the introducer. In such an embodiment, the probe tip may be aligned with the distal end of the introducer and the length of the exposed conductive portion of the introducer will affect characteristics of the resulting lesion, as has been described above with reference to FIG. 5. Alternatively, in some embodiments, the introducer can include an electrically insulated elongate member not having a conductive and exposed distal portion. In such embodiments, the distal end of the probe may protrude or extend from the distal end of the introducer and the distance that the probe tip extends may be altered by advancing or retracting the probe. The distance that the probe tip extends from the introducer will affect the formation of the lesion, as described above.

During the steps of inserting and positioning the probe, the probe may be inserted and positioned such that the distal end of the probe, comprising the active electrode, is the portion of the probe that is closest to the treatment site. If the treatment site includes a surface, for example, the probe may be inserted and positioned substantially perpendicular or generally upstanding to the surface, for example at an angle between about 80° and about 100° relative to the surface. In other embodiments, the probe may be positioned at an angle between about 45° and 135° or, in alternate embodiments, between about 60° and 120°. The probe may be inserted and positioned such that the distal end of the probe is directly adjacent to, or in contact with the target treatment site, or may be inserted and positioned such that the distal end of the probe is proximal to the target site. For example, in one embodiment, a probe may be inserted and positioned using what may be described as a "perpendicular" or "gun-barrel" approach. In this embodiment, the probe may be directed to the target site such that its longitudinal axis is substantially perpendicular or generally upstanding to the line or plane formed by the target tissue or site. For example, if the target tissue is a nerve, the probe may be positioned such that the probe is substantially perpendicular or generally upstanding relative to the nerve. If the target tissue includes more than one neural structure, such as a nerve or nerve branch, the probe may be inserted and positioned such that it is substantially perpendicular or generally upstanding to a plane containing the neural structures. As will be described in more detail below, embodiments of the present invention may allow for the creation of a lesion that is located primarily distally with respect to the distal end of a probe, thus allowing a probe that has been inserted substantially perpendicularly or generally upstanding relative to a target site to effectively treat the target site by delivering energy to form a lesion distal to the probe.

In alternate embodiments, the probe may be inserted at various angles to the target treatment site, depending on the procedure being performed and the anatomical structures involved. For example, in some embodiments, the probe may be inserted such that it is substantially parallel to a target nerve, for example at an angle of between about 0° and about 20°. In other embodiments, the probe may be inserted such that it is at an angle of between about 20° to about 70° to the target site. In general, embodiments of the present invention allow for various angles of approach by providing an apparatus and method of use thereof for creating a lesion of variable size and at various locations relative to the apparatus.

The step of inserting and positioning a probe may involve the insertion of a single probe to a location in the vicinity of a single target treatment site, the insertion of multiple probes in the vicinity of a single target treatment site, or the insertion of multiple probes to multiple locations in the vicinity of multiple target treatment sites. The probe or probes may be configured to deliver energy in a monopolar, bipolar or multi-polar configuration. If the probe or probes are configured to deliver energy in a monopolar configuration, the method of the current invention may also include a step of placing a reference electrode, such as a grounding pad, at another location on or in the body. The steps of inserting and positioning a probe may optionally be followed by any number of steps, for example prior to the commencement of the step of delivering energy including, but not limited to, one or more of: measuring one or more properties of a device or of tissue at or near the target treatment site; applying a stimulation signal to a tissue (for example, neural tissue) at or near the target treatment site; measuring the reaction to stimulation (for example, the somato-sensory evoked potential, or SSEP) of a tissue (for example, muscular or neural tissue) in response to the application of a stimulation signal at or near the target treatment site; inserting or removing material at or near the target treatment site; and performing another treatment procedure at or near the target treatment site. Further details regarding these steps may be found in U.S. Pat. No. 8,882,755 to Leung, et al., U.S. Pat. No. 7,819,869 to Godara, et al., U.S. Pat. No. 8,951,249 to Godara, et al., U.S. Patent Application Publication No. 2006/0259026 to Godara, et al., and U.S. Pat. No. 8,096,957 to Conquergood, et al. Following the performance of one or more of the above optional steps, one or more probes may be reinserted, moved, or otherwise repositioned and any optional steps may then be repeated.

The step of delivering energy to the target treatment site, for example to create a lesion at the target treatment site, may involve the creation of a lesion of a desired shape and at a desired location relative to the probe. As mentioned hereinabove, lesion shape and location may be affected by the length of the exposed distal end of the probe. The less of the probe that is exposed, the more distally, relative to the probe, the lesion will form. In addition, the shape of the lesion will be generally more spherical if less of the tip is exposed. For example, if the exposed length of the distal end is limited substantially to the distal-most hemisphere (i.e., the face) of the tip, then a substantially spherical lesion may form primarily distally with respect to the probe. Such a probe may be positioned such that the active electrode of the probe lies substantially proximal from the target site, for example a nerve. Energy may then be delivered to the probe such that a lesion may form substantially distal to the active electrode of the probe. Conversely, if more of the tip is exposed, then the lesion will appear more oblate and may form more radially (i.e. perpendicular to the longitudinal axis of the probe) around the distal end and the component of the lesion distal to the distal end will decrease.

The type, parameters, and properties of the energy delivered to the probe may vary depending on the application, and the invention is not limited in this regard. The energy may be one of various types of energy, for example electromagnetic, microwave, or thermal. In some embodiments, radiofrequency electrical current having a frequency of between about 10 kHz and about 1000 kHz, at a power of about 50 Watts, may be delivered to the probe.

In some embodiments of the method of the present invention, the step of delivering energy to the tissue may be preceded by, and/or done coincidently with, a step of utilizing a cooling or heat transfer system as discussed above with respect to FIGS. 3A-3F. Cooling may be used to reduce the temperature of the tissue in the vicinity of the site of energy delivery, allowing more energy to be applied without causing an increase to an unsafe temperature in local tissue. The application of more energy allows regions of tissue further away from the electrode(s) to reach a temperature at which a lesion can form, thus increasing the maximum size/volume of the lesion. Furthermore, depending on the structure of the probe, cooling may allow for a lesion to form at a position that is substantially distal to and, in some embodiments, spaced from the probe. Further details regarding cooled probes are disclosed in U.S. Patent Application Publication No. 2007/0156136 to Godara, et al. and U.S. Pat. No. 7,819,869 to Godara, et al., both of which are incorporated herein by reference. Thus, cooling an electrosurgical probe may change the size, shape, and location of formation of a lesion. As noted above, the theory described herein regarding tissue heating and lesion formation is not intended to limit the present invention in any way.

Figure 7:
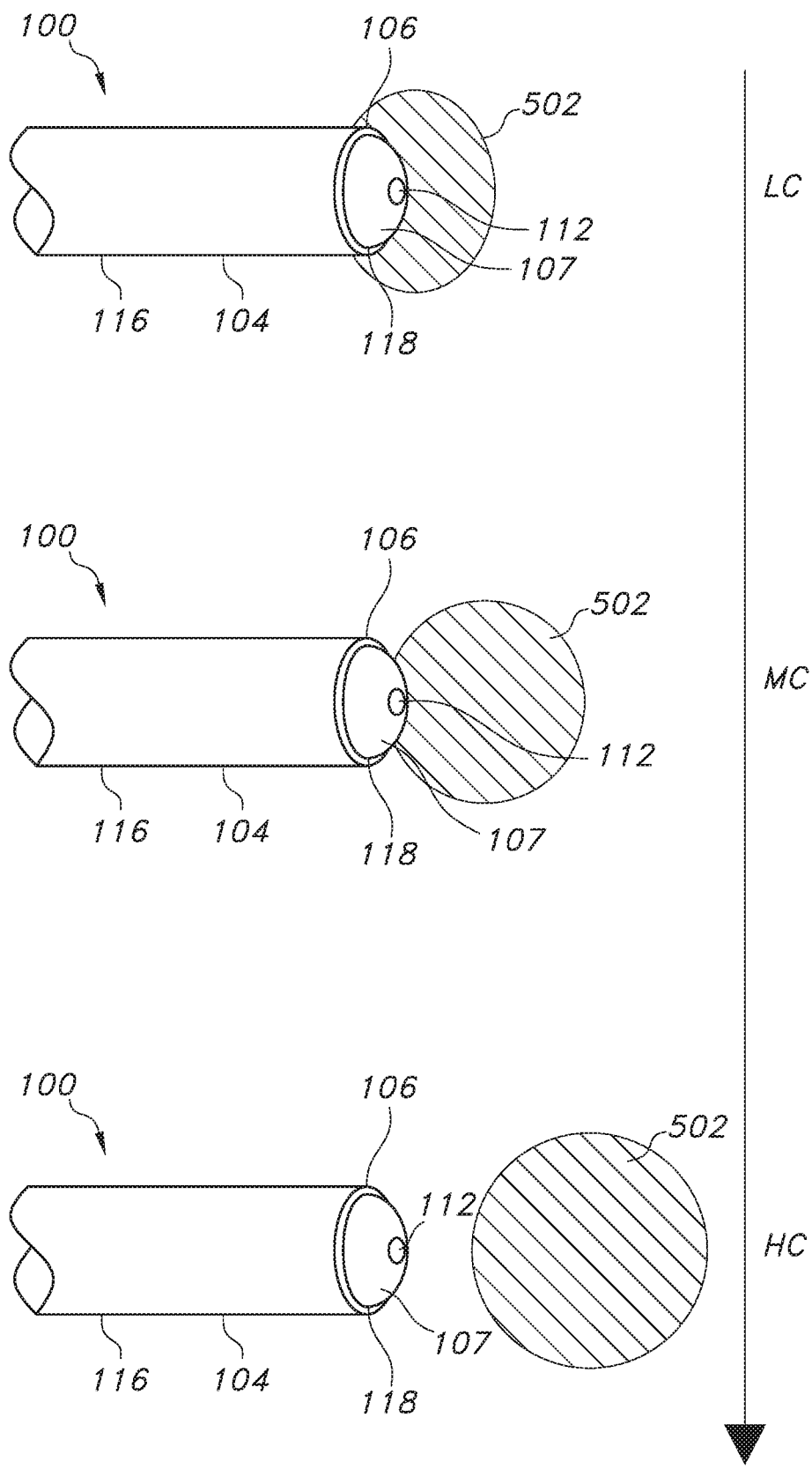
FIG. 7 is a comparative partial perspective view showing the distal region of an embodiment of a probe that can be used in the system of the present invention and examples of lesions that may be formed with various degrees of cooling.

In one embodiment, a step of applying cooling (or, in other words, removal of energy in Watts) may be used to facilitate the creation of a lesion that is distal to the probe 100 and which is spaced from the probe 100, as shown in FIG. 7. As long as a sufficient amount of cooling is applied to maintain the temperature of the tissue surrounding the distal end 106 of the probe 100 below the temperature at which a lesion will form (approximately 42° C.), a sufficient amount of power may be supplied from an energy source to create a lesion at some distance away from, for example distal to, the probe 100. The distance of the lesion from the probe 100 may depend on the amount of cooling delivered. For example, as shown in FIG. 7, if a relatively low amount of cooling is supplied (LC), the lesion may be relatively close to the probe 100. If a higher amount of cooling is supplied (HC), the lesion may form further away from the probe, where a medium amount of cooling (MC) results in a lesion formed in a space in between. This application of the method of the present invention may be used in cases where the target treatment site is not directly accessible by the probe, for example where the target site includes, lies within, or is disrupted by a crevice, fissure, or other uneven surface feature. As discussed previously, the application of cooling can be used to allow the creation of a lesion in a region of tissue further from the probe than might be possible without cooling. Cooling can thus be used to control the position of a lesion more precisely, with increased cooling allowing the creation of a lesion further from the probe.

Additionally, cooling may be modulated during energy delivery (and in some cases, accompanied by modulation of energy delivery) as follows: energy may be delivered initially in conjunction with cooling so that a lesion begins to form at some distance distally spaced apart from the probe; cooling may then be reduced, causing the lesion to extend at least partially in the direction of the probe. Thus, a further aspect of some embodiments of the method aspect of the present invention involves the control of cooling parameters in order to create a lesion at a desired location relative to the probe. As has been mentioned with respect to adjusting the exposed length of the distal end, cooling parameters may be adjusted before, during or after energy delivery.

Thus, the methods contemplated by the present invention provide for creating a lesion having a desired shape, size and location based on one or more factors, including, but not limited to, probe geometry and degree of cooling. The desired lesion parameters may be determined by a user in advance of a treatment procedure based, in some embodiments, on the specific tissue being targeted, as well as individual patient anatomy. For example, in procedures wherein the target site for formation of a lesion is located within a fissure, groove, or rut in a bone, it may not be possible to position the probe at the target site, and thus it may be desired to position the probe 100 at a location spaced from the target site. In this case, the user may select a probe 100 wherein the electrically exposed conductive portion 118 includes only the distal face 107 of the probe 100, and may select a high flow and/or low temperature of cooling fluid. Such a configuration may allow for the formation of a lesion distal to the probe tip 118, thus allowing the probe tip/electrode/conductive portion 118 to be located at some distance from the target site. If the probe 100 is positioned substantially perpendicular to the target site, a lesion may form at a location distal to the distal end of the probe (i.e., within the fissure in the bone). In another example, the target site may be directly on the surface of a bone. In this case, the user may select a probe 100 wherein the conductive portion 118 extends along the shaft proximally from the distal end, and may select a moderate or low amount of cooling. The user may position the distal end of the probe adjacent to the target site, for example about 0.1 mm to about 3 mm from the target site, or may allow the distal end of the probe 100 to touch the bone, and may orient the probe such that the longitudinal axis of the probe 100 is substantially perpendicular to the bone. In this case a lesion may form around the conductive portion of the probe 100, and between the distal end of the probe 100 and the bone. Alternatively, the aforementioned probe 100 having an electrode 118 comprising only the exposed distal face 107 may be used in this case as well. In both of these examples, a probe 100 with an adjustable insulating sheath may be used to provide an appropriately sized exposed the electrode 118 to produce the desired lesion. Alternatively, as mentioned hereinabove, the position of a probe within an introducer may be altered by advancing and/or retracting the probe to provide an appropriately sized exposed the electrode 118 to produce the desired lesion.

Figure 8A:
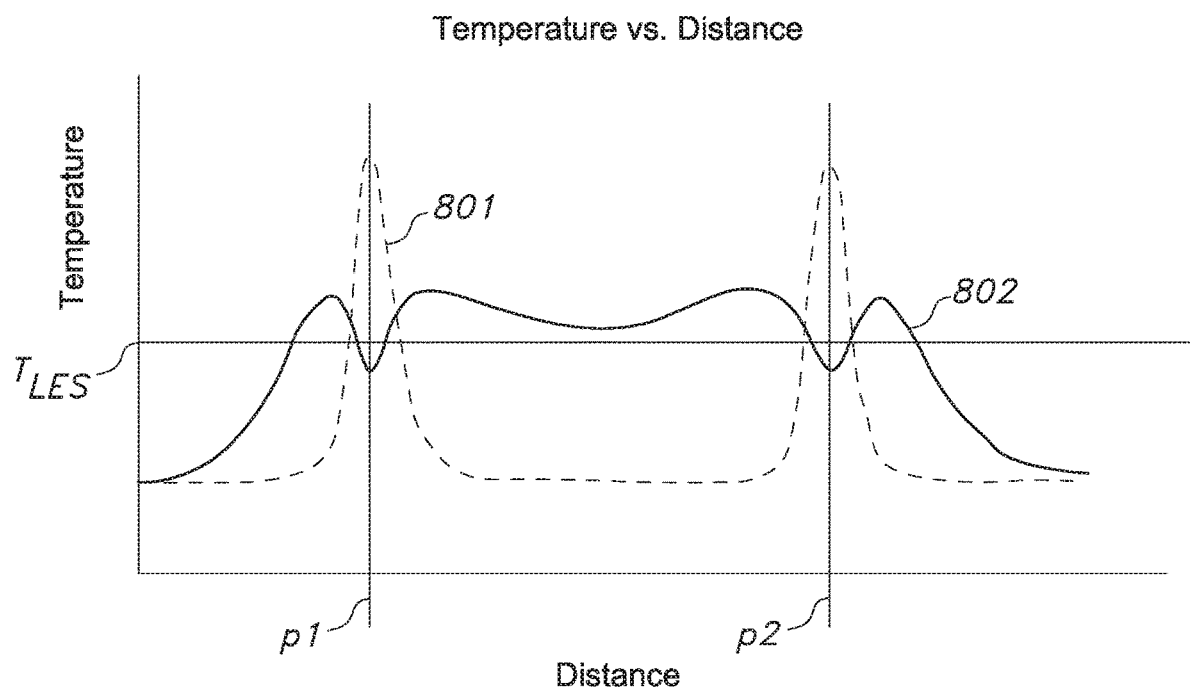
FIG. 8A is a graph of temperature in a uniform tissue vs. relative distance using an embodiment of a probe that can be used in the system of the present invention with cooling and without cooling.
Figure 8B:
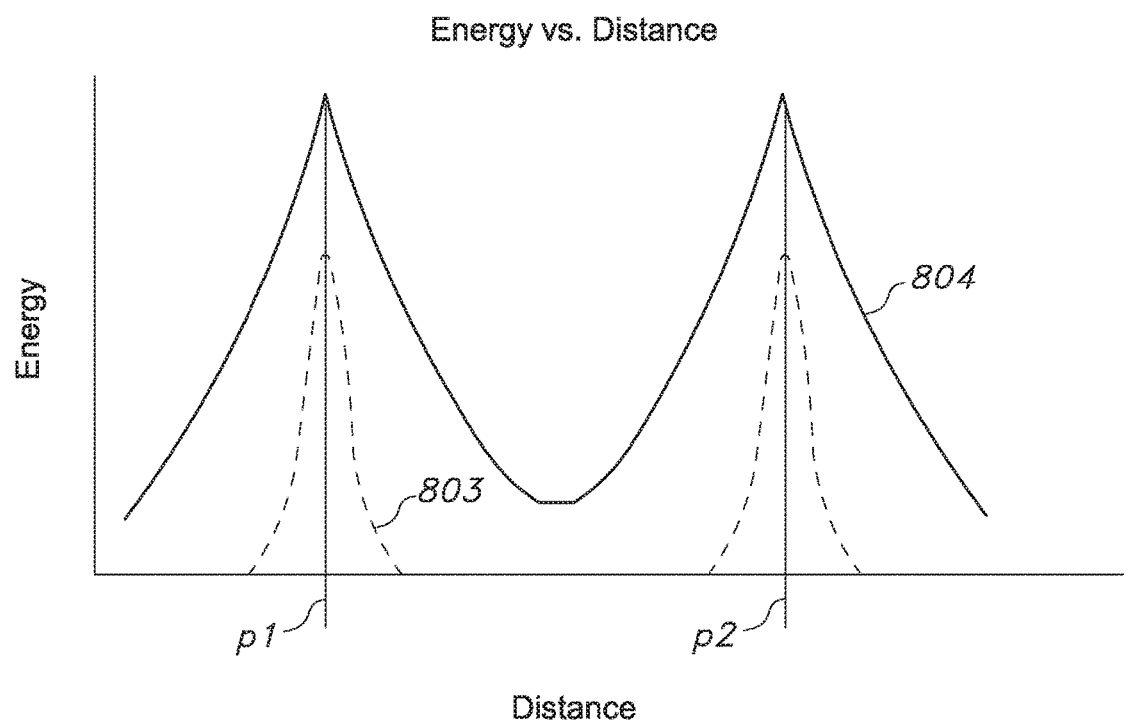
FIG. 8B is a graph of energy in a uniform tissue vs. relative distance using an embodiment of a probe that can be used in the system of the present invention with cooling and without cooling.

In some embodiments, two cooled probes 100 in a bipolar configuration may be used, which may allow for the creation of a substantially uniform lesion between the electrodes 118 of the two probes 100. This concept is illustrated in FIG. 8A, showing a graph of temperature vs. distance in a tissue with uniform thermal/electrical properties. The electrodes 118 of the two probes 100 are located at positions p1 and p2 on the x-axis and the temperature needed to create a lesion is noted as $T_{LES}$ on the y-axis. In FIGS. 8A and 8B, solid lines 802 and 804 represent a cooled probe assembly, while dashed lines 801 and 803 represent a non-cooled probe assembly. Without the benefits of cooling, the higher the power that is supplied to the electrodes 118, the higher the temperature around the electrodes 118 will be. Curve 801 shows a temperature profile, as may be typically achieved using non-cooled probes in a uniform tissue. In such a configuration it is difficult to create a lesion extending from p1 to p2 because by supplying a large amount of power to the electrodes 118, the temperature at the locations p1 and p2 of the electrodes reaches very high levels. High temperatures at the electrodes may cause nearby tissue to char and possibly adhere to distal regions 104. Furthermore, raising the temperature of tissue causes the impedance of the tissue to increase and limits the penetration of current into the tissue, thereby limiting the size of the lesion that can be created. In contrast, cooled probe assemblies may be used to form a desired lesion between p1 and p2 while reducing such temperature effects. Curve 802 shows a typical temperature profile for a uniform tissue as may be seen when using two cooled probe assemblies. The temperatures at the distal end regions, p1 and p2, are reduced relative to the surrounding tissue due to the effect of the cooling. This allows for higher power to be transmitted to the electrodes 118 without concern for tissue charring. In addition, because the temperature of tissue surrounding the electrodes 118 is reduced, the impedance of the surrounding tissue will not increase significantly and therefore current supplied by the electrodes 118 can penetrate more deeply into the tissue. As illustrated in FIG. 8A, a lesion can therefore be created between p1 and p2 using cooled probes due to the lower local temperatures at p1 and p2. Although FIG. 8A shows the temperature at p1 and p2 to be below the lesioning temperature, the cooling supplied to the cooled probes may be reduced or eliminated allowing the temperature of tissue around p1 and p2 to increase in order to complete the lesion between p1 and p2.

In some embodiments, after the creation of a lesion, the probe 100 may be repositioned, and energy may again be delivered in order to form a further lesion. For example, after the formation of a first lesion, the probe 100 may be withdrawn from the target site either partially or fully. In the case of partial withdrawal, energy may be delivered to the site at which the probe 100 has been withdrawn to, such that a further lesion is formed. In the case of full withdrawal, the probe may be re-inserted and re-positioned at a second location, and energy may be delivered to the second location to form a further lesion. The step of repositioning may be performed any number of times, to form any number of lesions, as determined by a user. In embodiments comprising a steerable probe, the probe may be repositioned without withdrawing the probe, by actuating the steering means associated with the probe.

Methods of the present invention may be used for various applications, including for the treatment of pain associated with many conditions. Examples of such conditions include, but are not limited to, Complex Regional Pain Syndrome (CRPS), Trigeminal Neuralgia, Joint Specific Peripheral Neuropathy, Facet Joint Pain, Intervertebral disc pain, Sacroiliac Joint Syndrome (SIJS) and Hypogastric or Pelvic Pain. In general, these conditions may be treated by affecting at least one target neural structure that may be associated with a patient's pain in accordance with method embodiments of the present invention. For example, in the case of trigeminal neuralgia, embodiments of the present invention may be used to form a lesion at the trigeminal nerve. Some embodiments of a method of the present invention may also be used to treat further sources of pain, as will be described in more detail below.

In some embodiments, any or all of the method steps described above may be performed with the aid of imaging. For example, the step of inserting a probe may be performed under X-ray fluoroscopic guidance. In a further embodiment, the imaging may be performed in a gun-barrel manner, wherein the device is visualized along its longitudinal axis.

In some embodiments, rather than being delivered in a continuous manner, energy may be delivered in a series of amplitude or frequency modulated pulses, whereby tissue heating is inhibited by interrupting periods of energy delivery with periods in which energy is delivered at a lower voltage. In one specific embodiment, energy is delivered according to a set duty cycle of signal on time/off time, wherein the signal is "on" less than 100% of the time, as follows: during signal "on time" energy is delivered at a voltage that may beneficially be higher than voltages that can safely be used during continuous energy delivery (100% duty cycle) procedures; during signal "off time," the heat generated in the vicinity of the probe may disperse throughout the tissue, raising the temperature of tissue away from the probe, while tissue in the vicinity of the probe drops; energy is again applied and the delivery is cycled through "on time" and "off time" until a predetermined endpoint (e.g., time or temperature) is reached or until a practitioner decides to end the treatment. The reduction in temperature of tissue in the vicinity of the probe during signal "off time" may allow a higher voltage to be used (during "on time"), than would tend to be used in a continuous energy delivery procedure. In this way, the pulsing of energy delivery, either between signal "on time" and "off time," as described above, or between a higher voltage and a lower voltage (for example, a voltage capable of generating a lesion in the tissue and a voltage not capable of generating a lesion in the tissue, given the frequency of energy being delivered), the total amount of current deposited into the tissue may be sufficient to create a larger lesion, at a further distance from the probe, than would be possible using continuous energy delivery without maintaining the tissue in the vicinity of the probe at a temperature that may cause charring.

As has been mentioned, a system of the present invention may be used to produce a generally uniform or substantially homogeneous lesion substantially between two probes when operated in a bipolar mode. In certain cases, generally uniform or substantially homogeneous lesions may be contraindicated, such as in a case where a tissue to be treated is located closer to one active electrode than to the other. In cases where a uniform lesion may be undesirable, using two or more cooled probes in combination with a suitable feedback and control system may allow for the creation of lesions of varying size and shape. For example, preset temperature and/or power profiles that the procedure should follow may be programmed into a generator prior to commencement of a treatment procedure. These profiles may define parameters (these parameters would depend on certain tissue parameters, such as heat capacity, etc.) that should be used in order to create a lesion of a specific size and shape. These parameters may include, but are not limited to, maximum allowable temperature, ramp rate (i.e., how quickly the temperature is raised) and the rate of cooling fluid flow, for each individual probe. Based on temperature or impedance measurements performed during the procedure, various parameters, such as power or cooling, may be modulated, in order to comply with the preset profiles, resulting in a lesion with the desired dimensions. Similarly, it is to be understood that a uniform lesion can be created, using a system of the present invention, using many different pre-set temperature and/or power profiles which allow the thermal dose across the tissue to be as uniform as possible, and that the present invention is not limited in this regard.

Embodiments of the method aspect of the present invention may be useful for creating a lesion having a desired shape, size and/or location within various tissues of a human or animal. More specifically, some embodiments of the present invention can include treatment procedures for treating one or more target tissue sites associated with a patient's vertebral column. For example, treatment procedures may be performed at various locations external to the vertebrae, including but not limited to target sites at the cervical, thoracic, lumbar and sacral regions of the spine. In addition, treatment procedures may be performed at target sites within the vertebrae themselves, referred to as an intraosseous procedure. Furthermore, treatment procedures may be performed at target sites within one or more intervertebral discs. Although several exemplary embodiments of such procedures will be presently described, the present invention is not limited to such procedures and may be practiced at various target sites within a patient's body. In any or all of the embodiments disclosed herein, a treatment procedure can include a step of determining desired lesion parameters, including, but not limited to, shape, size and location, and selecting probe geometry, location and cooling in order to create the desired lesion.

One application of an embodiment of a method of the present invention is for the treatment of pain within or in the vicinity of an intervertebral disc. As is disclosed in U.S. Pat. No. 6,896,675 to Leung, et al., and U.S. Pat. No. 6,562,033 to Shah, et al., U.S. Pat. No. 8,043,287 to Conguergood, et al., U.S. Pat. No. 8,882,755 to Leung, et al., U.S. Patent Application Publication No. 2005/0277918 to Shah, et al., and U.S. Pat. No. 7,294,127 to Leung, et al., all of which are incorporated herein by reference, RF energy may be delivered through a cooled probe to an intervertebral disc of a patient in order, for example, to treat pain. Treatment of an intervertebral disc may generally include the steps of: inserting at least one probe into the intervertebral disc of a patient; and delivering energy through the probe(s) to the tissue of the intervertebral disc. As described above, the at least one probe may be cooled and the degree of cooling may affect the size, shape and/or location of a lesion formed within the disc.

Figure 9:
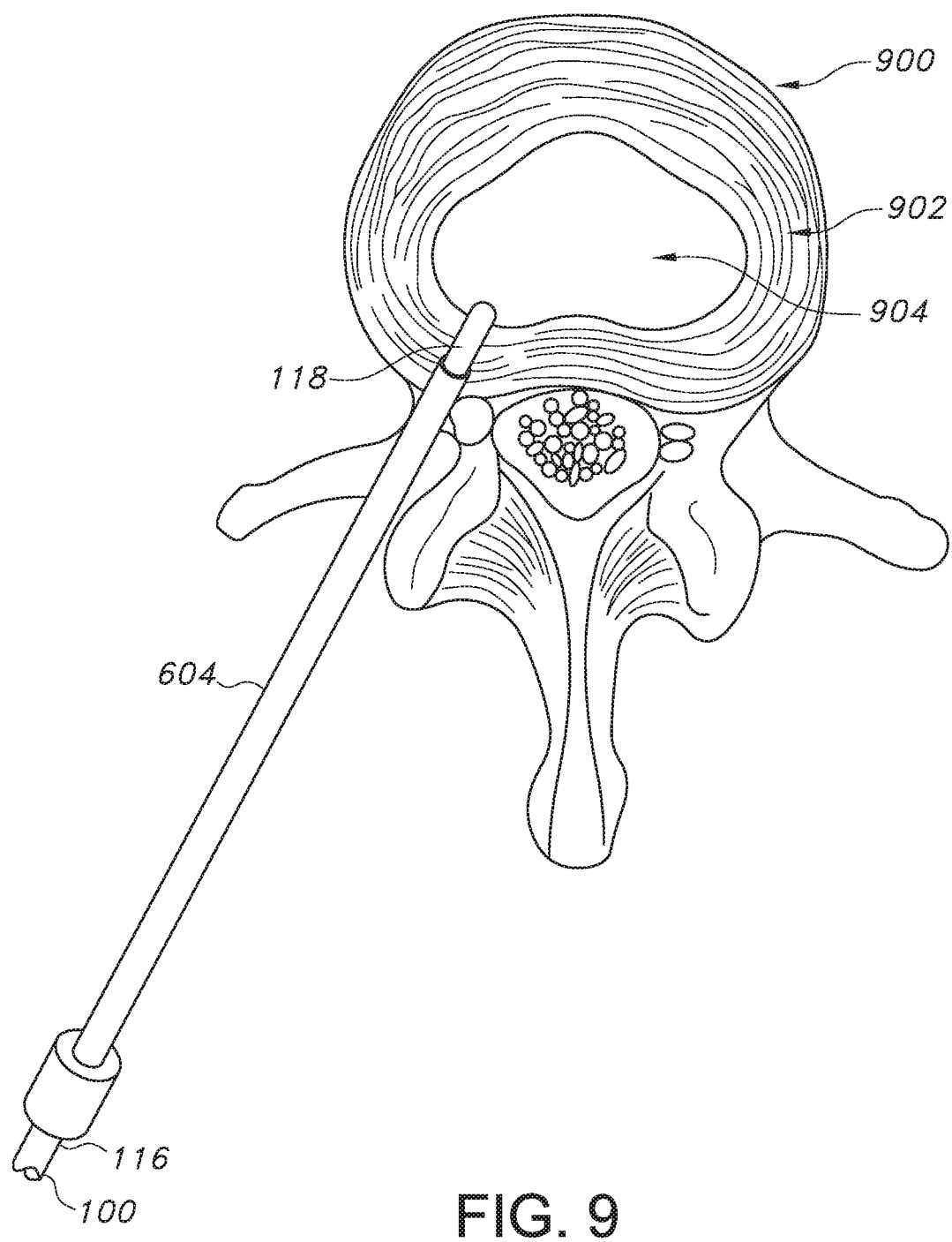
FIG. 9 is a top view of an embodiment of a probe of the present invention positioned within an intervertebral disc of a patient.

Referring to FIG. 9, the step of inserting at least one probe into an intervertebral disc 900 may proceed generally as follows (further details are provided in the aforementioned references): With a patient lying on a radiolucent table, fluoroscopic guidance may be used to insert at least one probe towards the posterior of an intervertebral disc. As mentioned above, the step of insertion can include the use of an introducer apparatus, for example comprising an obturator/stylet disposed within an introducer. One method of accessing the disc is the extrapedicular approach, in which the introducer passes just lateral to the pedicle, but other approaches may be used. In some embodiments, the introducer apparatus may be advanced until the distal end of the stylet penetrates the annulus fibrosis 902 and enters the nucleus pulposus 904. In other embodiments, the introducer apparatus may be advanced until the distal end of the stylet is within the annulus fibrosis 902. In further embodiments, the introducer apparatus may be advanced until the distal end of the stylet is proximal to, but not within, annulus fibrosis 902. In some particular embodiments, the stylet may be electrically connected to the generator such that the stylet forms part of an impedance monitoring circuit, as described above. In such embodiments, monitoring the impedance may assist in positioning the introducer apparatus at a desired location, since different tissues may have different impedances. When the introducer apparatus has been positioned, the stylet may be removed from the introducer. In some embodiments, a second introducer apparatus may then be placed contralateral to the first introducer in the same manner, and the stylet may be removed. After removal of the stylet(s), the probe(s) may be inserted into the introducer(s), placing the active electrodes in the disc such that the distance between active electrodes is, for example, about 1 mm to about 55 mm.

A method embodiment of the present invention may also be used to treat intraosseous target sites, i.e., target sites within a bony structure. Such procedures can be used to, for example, treat a tumor in the bony structure or lesion a neural structure within the bone. In an intraosseous procedure, one or more introducers may generally be used to gain access to the bone to be treated, for example, a vertebra of a spinal column. In such embodiments, the introducers can include a drill or other means for accessing the bone. Alternatively or in addition, a hammer or a reamer may be used to access an intraosseous site. As is the case with procedures related to intervertebral discs, one or more probes may be inserted at a site or sites within a bone and energy may be delivered to active electrodes located at the distal regions of the probes. Energy may be delivered in a bipolar mode, or in a monopolar mode. Furthermore, as mentioned above, one or more of the probes may be cooled to allow for the formation of a lesion having a desired size, shape and location.

Another application of embodiments of the apparatus and method of the present invention is for the treatment of pain emanating from a patient's neck (i.e., the cervical region of the spine) as is disclosed in U.S. Patent Application Publication No. 2007/0156136 to Godara, et al.

Figure 10:
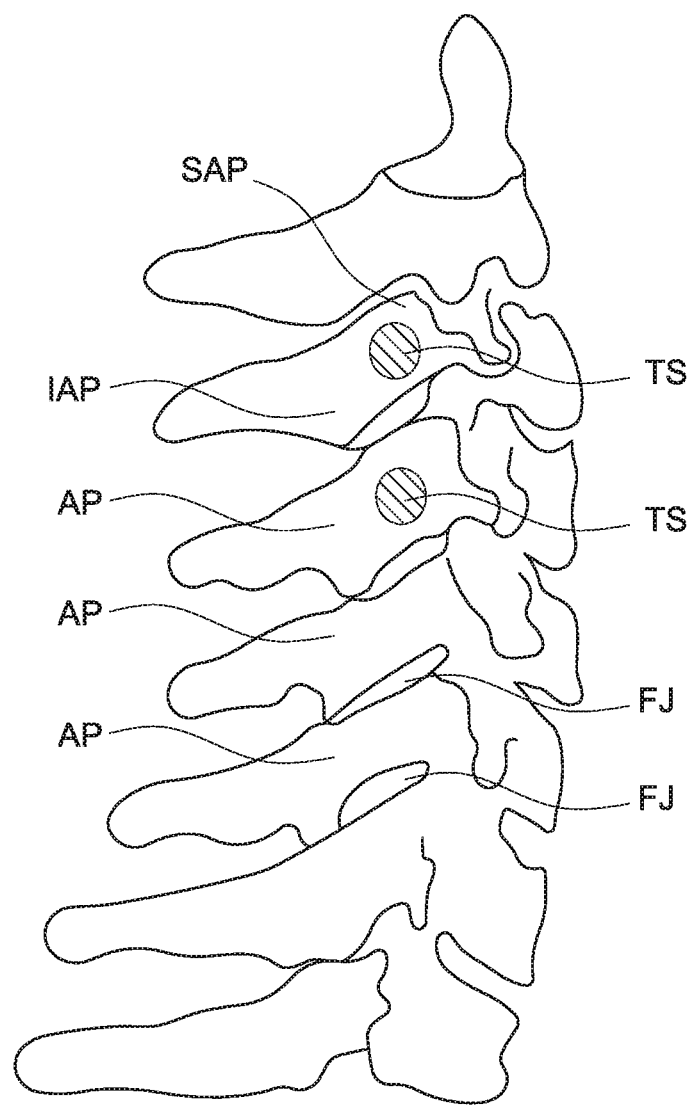
FIG. 10 is a view of the cervical vertebrae of a patient's spine, showing target sites for facet denervation.

Referring now to FIG. 10, a lateral view of the cervical region of the spine is shown. The cervical region of the spine generally includes seven cervical vertebrae and their associated zygapophyseal, or facet, joints. Nerves innervating the facet joints (FJ) are thought to be responsible for certain types of neck/cervical pain. The cervical facet joints are paired, synovial joints found along the back of the cervical vertebral column at intervertebral levels C2-3 to C7-T1. The cervical facet joints (FJ) are planar joints formed between the inferior articular process (IAP) of one vertebra and the superior articular process (SAP) of the adjacent vertebra. Each articular process (AP) bears a circular or ovoid facet that is covered by articular cartilage, and each joint is enclosed by a fibrous joint capsule lined by a synovial membrane. The cervical facet joints are innervated by articular branches derived from the medial branches of the cervical dorsal rami. The medial branches of the typical cervical dorsal rami curve medially and posteriorly as they exit the intervertebral foramen, hugging the articular pillars. Articular branches arise as the nerve approaches the posterior aspect of the articular pillar. An ascending branch innervates the facet joint above, and a descending branch innervates the joint below.

A method of treating cervical/neck pain in accordance with one embodiment of the present invention will be presently described. The description will reference the anatomy of the facet nerve of the fourth cervical vertebra; however persons of skill in the art will recognize that the method may be used to treat other nerves of other cervical vertebrae as well, for example the third occipital nerve of the third cervical vertebra. Variations of the described method may be required in order to accommodate anatomical differences of other cervical vertebrae. In some embodiments, the target site for treating cervical/neck pain can include the nerves innervating the facet joint. As described hereinabove, these nerves may be located substantially adjacent to the articular pillar of the cervical vertebra. Thus the target site (TS) for energy delivery may be the region located slightly cephalad to the centroid of the articular pillar, as shown in FIG. 10.

Figure 11A:
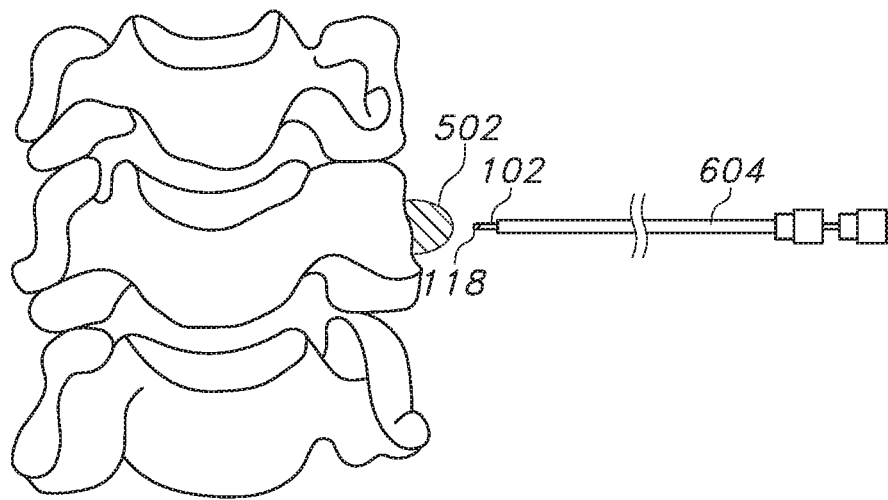
FIGS. 11A and 11B illustrate various positions of a probe that can be used in the system of the present invention with respect to the C3-C5 region of the cervical vertebrae.
Figure 11B:
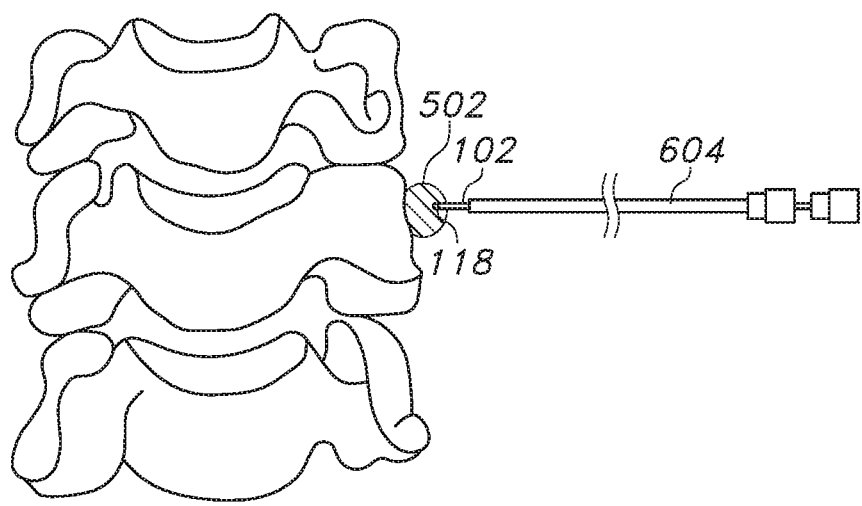

In one specific embodiment, the patient may be placed in the prone position in preparation for the treatment procedure. The user may optionally administer various treatments, such as anesthetics or antibiotics, for example. The user may insert at least one probe, such as probe 100 described hereinabove, percutaneously towards the target site. The step of inserting at least one probe can include the use of an introducer apparatus, as described above. Such an apparatus may be an introducer apparatus that includes an introducer 604 and an obturator 606. The user may insert the introducer apparatus percutaneously into the patient via a lateral approach, such that the longitudinal axis of the introducer is substantially perpendicular or generally upstanding, for example at an angle of about 80° to about 100°, relative to the target site (i.e., the centroid of the articular pillar). In other words, the longitudinal axis of the introducer may be substantially perpendicular or generally upstanding to the anterior-posterior (AP) axis of the body, as shown in FIGS. 11A-B, which show AP views of a portion of the cervical spine. In other embodiments, the probe may be at other angles relative to the AP axis of the body, for example between about 45° and about 135°. In yet further embodiments, the probe may be substantially parallel to the AP axis of the body. The insertion step may be facilitated with the use of fluoroscopic imaging techniques. The user may continue the insertion until a distal end of the introducer apparatus contacts the bony surface of the articular pillar, or may stop the insertion when the distal end lies some distance, for example about 2 to about 4 millimeters, proximal from the bony surface. In other embodiments, the user may contact the bony surface of the articular pillar with the tip of the introducer, and may then retract the introducer apparatus such that the distal end lies some distance proximal from the surface, as has been described. Thus, depending on the configuration and positioning of the probe and/or introducer apparatus, the distal end of the probe may be in contact with the surface of the articular pillar, or may be located some distance away from the bone. The position of the probe may be pre-determined based on the desired lesion size, shape and location, as mentioned above. The position of the probe may be verified using a variety of techniques, for example by using fluoroscopic imaging. In some embodiments, the user may use depth stoppers to aid in the marking and/or maintaining the position of the introducer apparatus within the patient's body.

When the introducer apparatus has been positioned, the user may withdraw the obturator/stylet from the introducer, leaving the introducer in place. Depending on the positioning of the introducer apparatus, the distal end of the introducer may now be touching the bone, or may be some distance proximal from the bony surface, for example about 3 mm away from the bone. The user may then insert a probe into the lumen of the introducer. The probe may be operatively connected to a source of cooling fluid, for example pumps 610, and may further be operatively connected to a source of energy, such as generator 608, in order to deliver energy to the target site.

As described above, depending on the configuration and positioning of the probe, as well as the degree of cooling, the lesion formed at the target site may be of a variety of shapes and sizes, as described above. For example, as shown in FIG. 11A, the conductive portion 118 of the probe can include substantially the distal face 107 of the probe. Thus, if the probe is sufficiently cooled, a lesion 502 may form distal to the probe in a substantially spherical shape. In another example, as shown in FIG. 11B, the conductive portion 118 of the probe may extend proximally along the length of the probe for a short distance, for example between about 2 mm and about 4 mm. In such an embodiment, with a sufficient amount of cooling, a lesion 502 may form around the conductive portion as well as distal to the probe. Thus, the degree of cooling, as well as the probe geometry/configuration and positioning may each affect the lesion that may be formed. Because lesions formed by this method may reach tissue that lies within grooves or other indentations within a bone, or directly on the surface of a bone, this method may be particularly useful for lesioning of the nerves of the medial branch of the dorsal ramus at the cervical region of the spine.

Figure 12:
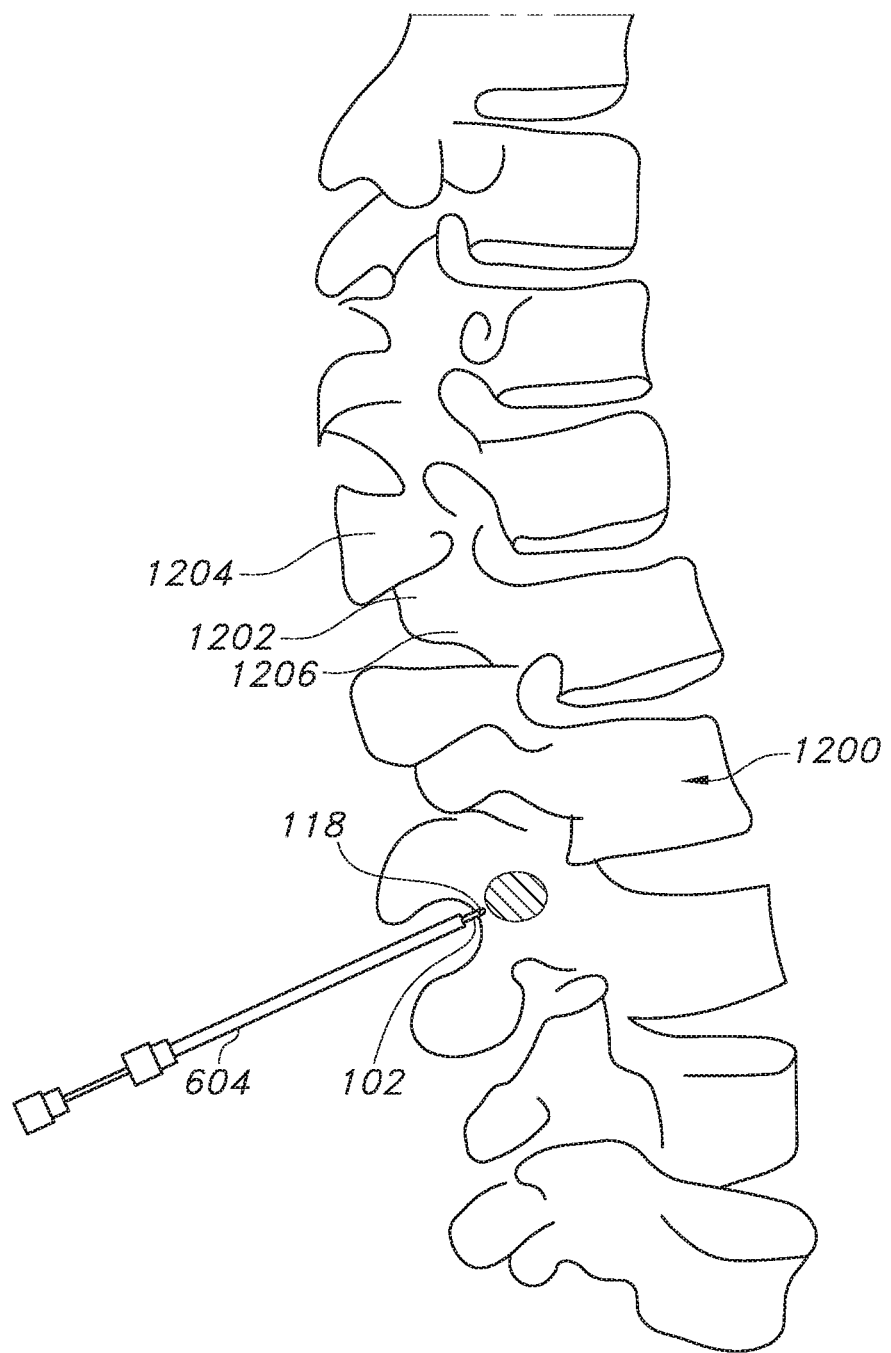
FIG. 12 illustrates a probe that can be used in the system of the present invention, where the probe is positioned at the lumbar region of the spine.

Another application of embodiments of a method of the present invention is for the treatment of pain in the lumbar region of a patient's spine. With reference now to FIG. 12, the lumbar region generally consists of five vertebrae 1200 and their associated facet joints. The lumbar facet joints are formed by the superior 1202 and inferior 1204 articular processes of successive vertebrae. On the dorsolateral surface of each superior articular facet is a prominence known as the mammillary body or process. There is also an accessory process which arises from the dorsal surface of the transverse process 1206 near its junction with the superior articular process. The nerve supply of the lumbar facet joints is derived from the dorsal primary ramus of the nerve root. Each facet joint receives innervation from two successive medial branches of the dorsal primary ramus. At the L1-L4 levels, each dorsal ramus arises from the spinal nerve at the level of the intervertebral disc. About 5 mm from its origin, the dorsal ramus divides into a medial and lateral branch. The medial branch runs caudally and dorsally, lying against bone at the junction of the root of the transverse process with the root of the superior articular process. The medial branch runs medially and caudally just caudal to the facet joint, and becomes embedded in the fibrous tissue surrounding the joint. The medial branch gives off a branch to each of the proximal and distal facet joint. The proximal facet nerve supplies the rostra aspect of the next lower joint. The course of the medial branch of the dorsal ramus is fixed anatomically at two points: at its origin near the superior aspect of the base of the transverse process, and distally where it emerges from the canal formed by the mammillo-accessory ligament.

A method of treating lumbar pain in accordance with an embodiment of the present invention will be presently described. The description will reference the anatomy of the first lumbar vertebra; however persons of skill in the art will recognize that the method may be used to treat other lumber vertebrae as well. Variations of the described method may be required in order to accommodate anatomical differences of other lumbar vertebrae. In some embodiments, the target site for treating lumbar pain can include the nerves innervating the facet joint. As described hereinabove, these nerves may be located substantially adjacent to the articular process of the lumbar vertebra. Thus the target site for energy delivery may be the dorsal surface of the transverse process just caudal to the most medial end of the superior edge of the transverse process.

In one specific embodiment, the patient may be placed in the prone position in preparation for the treatment procedure. The user may optionally administer various treatments, such as anesthetics or antibiotics, for example. The user may insert at least one probe, such as probe 100 described hereinabove, percutaneously toward the target site. In general, due to the large and controllable lesion size afforded by the structure of probe 100, probe 100 may be inserted from a number of angles and positioned at a wide variety of locations to create a lesion at the target site. The step of inserting at least one probe can include the use of an introducer apparatus. Such an apparatus may be an introducer apparatus comprising the introducer 604 and the obturator 606. The user may insert the introducer apparatus percutaneously into the patient via several different approaches. For example, in one embodiment, the introducer may be inserted in the sagittal plane of the medial branch one or two levels caudal to the target site, and may be advanced in a rostral and anterior direction. In another embodiment, the introducer may be advanced from a more lateral position with oblique medial angulation. In other embodiments, the probe may be introduced at other sites, and inserted at other angles. The insertion step may be facilitated with the use of fluoroscopic imaging techniques. The user may continue the insertion until a distal end of the introducer apparatus contacts the dorsal surface of the transverse process just caudal to the most medial end of the superior edge of the transverse process, or may stop the insertion when the distal end lies some distance, for example about 2 to about 4 millimeters, proximal from the surface. In other embodiments, the user may contact the surface of the transverse process with the tip of the introducer, and may then retract the introducer apparatus such that the distal end lies some distance proximal from the surface. In some embodiments, the user may use depth stoppers to aid in the marking and/or maintaining the position of the introducer apparatus within the patient's body.

Depending on the configuration and positioning of the probe, as well as the degree of cooling supplied to the probe, the lesion formed at the target site may be of a variety of shapes and sizes, as described above. For example, as shown in FIG. 12, in embodiments wherein the conductive portion 118 of the probe 100 extends proximally along the length of the probe for a small distance, for example about 2 mm to about 6 mm, for example about 4 mm, and with a sufficient amount of cooling, a lesion 502 may form around the conductive portion as well as distal to the probe. Because lesions formed by this method may reach tissue that lies within grooves or other indentations within a bone or directly on the surface of a bone, this method may be particularly useful for lesioning of the nerves of the medial branch of the dorsal ramus at the lumbar region of the spine.

Figure 13:
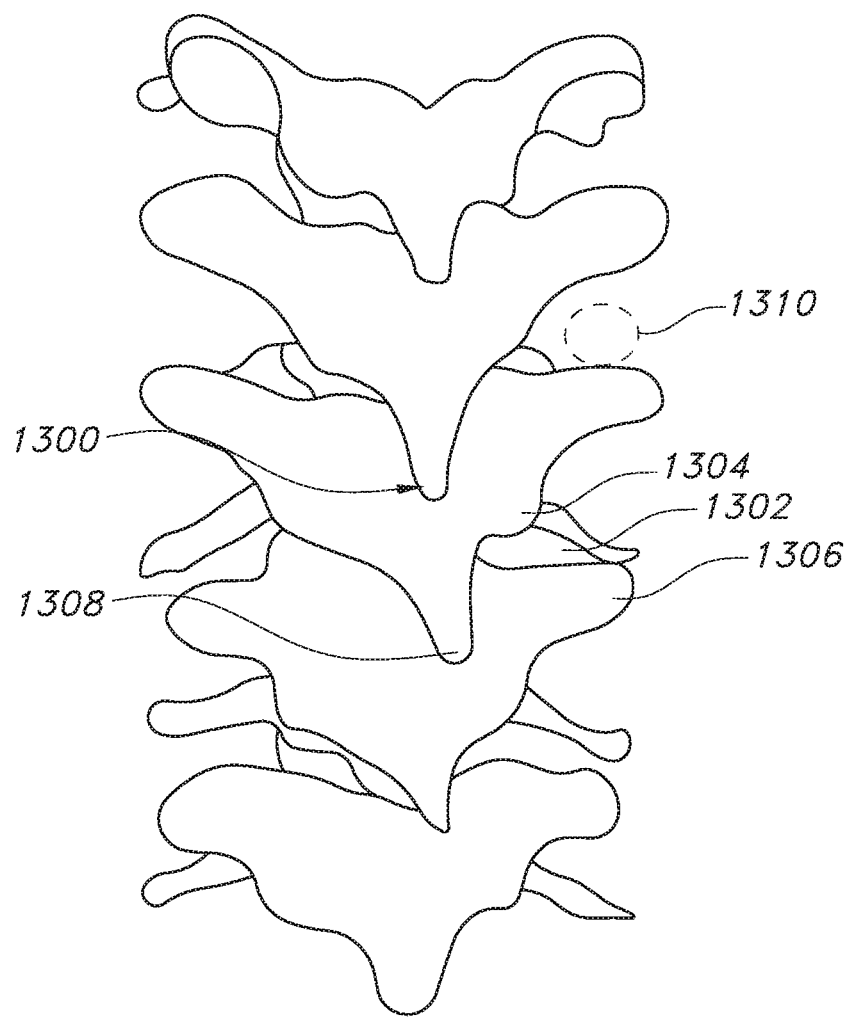
FIG. 13 is a view of the thoracic vertebrae of a patient's spine, showing a target site for energy delivery.

Referring now to FIG. 13, the vertebrae 1300 of the thoracic region are intermediate in size between those of the cervical and lumbar regions, the upper vertebrae being smaller than those in the lower part of the region. The vertebral bodies are generally as broad in the antero-posterior as in the transverse direction. At the ends of the thoracic region the vertebral bodies resemble respectively those of the cervical and lumbar vertebrae. As shown in FIG. 13, the pedicles of the thoracic vertebrae 1300 are directed backward and slightly upward. The spinous process 1308 is long and extends posterior and caudal, and ends in a tuberculated extremity. The thoracic facet joints are paired joints located between the superior articular process 1302 and inferior articular process 1304 of the vertebrae. The superior articular processes are thin plates of bone projecting upward from the junctions of the pedicles and laminae; their articular facets are practically flat, and are directed posteriorly and slightly lateral and upward. The inferior articular processes are fused to a considerable extent with the laminae, and project slightly beyond their lower borders; their facets are directed anteriorly and slightly medial and downward. The transverse processes 1306 arise from the arch behind the superior articular processes and pedicles; they are directed obliquely backward and lateral. The thoracic facet joints are innervated by the medial branches of the dorsal rami. The medial branches pass between consecutive transverse processes and head medially and inferiorly. They then innervate the facet joint at the level of their spinal nerve and the joint below. At T1-3 and T9-10, the medial branches cross the superior-lateral aspect of the transverse process. At T4-8, the medial branches follow a similar course, but may remain suspended within the intertransverse space. At T11-12, the medial branch has a course akin to the lumbar medial branches such that they course posteriorly along the medial aspect of the transverse process, at the root of the superior articular process.

Due to the varied course of the medial branch across the twelve thoracic levels, the lack of bony landmarks associated with the thoracic medial branch, and the anatomic differences among patients, it is often required to create several lesions in order to denervate one thoracic facet joint. Embodiments of the present invention may allow for the formation of a single large lesion for the denervation of a facet joint, for example by using cooling, thus providing a more straightforward and less invasive procedure.

A method of treating thoracic pain in accordance with an embodiment of the present invention will be presently described. The description will reference the anatomy of the first through tenth thoracic vertebrae. Variations of the described method may be required in order to accommodate anatomical differences of other thoracic vertebrae. In some embodiments, the target site for treating thoracic pain can include the nerves innervating the facet joint. As described hereinabove, these nerves may be located substantially laterally between two consecutive transverse processes, or substantially adjacent the superior edge of a transverse process. Thus the target site 1310 for energy delivery may be the superior lateral edge of the transverse process and the region immediately superior thereto.

In one specific embodiment, the patient may be placed in the prone position in preparation for the treatment procedure. The user may optionally administer various treatments, such as anesthetics or antibiotics, for example. The user may insert at least one probe, such as the probe 100 described hereinabove, percutaneously toward the target site. In general, due to the large and controllable lesion size afforded by the structure of the probe 100, the probe 100 may be inserted from a number of angles and positioned at a wide variety of locations to create a lesion at the target site. The step of inserting at least one probe can include the use of an introducer apparatus. Such an apparatus may be an introducer apparatus comprising the introducer 604 and the obturator 606.

Figure 14:
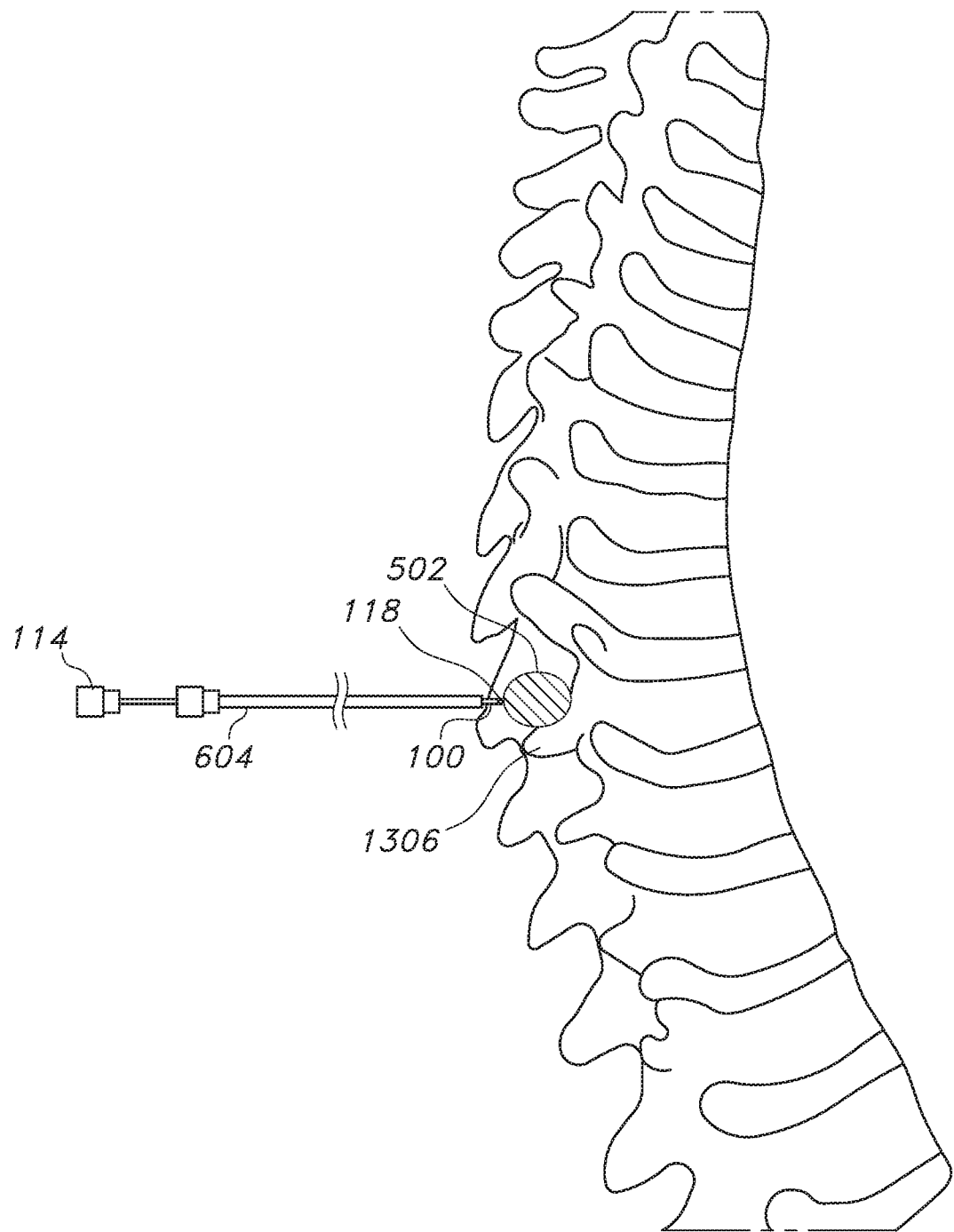
FIG. 14 illustrates a position of a probe that can be used in the system of the present invention with respect to the thoracic vertebrae.

The user may insert the introducer apparatus percutaneously into the patient via several different approaches. For example, as shown in FIG. 14, in one embodiment, the introducer may be inserted slightly medial to the lateral edge of the transverse process 1306, and advanced in the anterior direction. In another embodiment, the introducer may be advanced from a more medial position with oblique lateral angulation. In other embodiments, the probe may be introduced at other sites, and inserted at other angles. In some embodiments, the insertion step may be facilitated with the use of fluoroscopic imaging techniques. The user may continue the insertion until a distal end of the introducer apparatus contacts the transverse process 1306. The user may then "walk" the introducer apparatus in the cranial direction, until the distal end of the introducer begins to slip over the superior edge of the transverse process 1306. The user may then withdraw the introducer slightly, such that the distal end of the introducer is substantially above the superior lateral edge of transverse process 1306. In some embodiments, the user may use depth stoppers to aid in the marking and/or maintaining the position of the introducer apparatus within the patient's body.

Depending, for example, on the configuration and positioning of the probe, as well as the degree of cooling supplied to the probe, the lesion formed at the target site may be of a variety of shapes and sizes, as described hereinabove. For example, as shown in FIG. 14, in embodiments wherein the conductive portion 118 of the probe 100 extends proximally along the length of the probe for a small distance, for example between about 1 mm and about 4 mm, and with a sufficient amount of cooling, for example between about 10 ml/min and about 25 ml/min, a lesion 502 may form around the conductive portion as well as distal to the probe. Because lesions formed by this method may be substantially large, for example between about 150 mm$^3$ and about 500 mm$^3$ in volume, this method may be particularly useful for lesioning of the nerves of the medial branch of the dorsal ramus at the thoracic region of the spine.

A further application of embodiments of the apparatus and method of the present invention is for the treatment of pain emanating from the Sacroiliac (SI) joint and/or the surrounding region. Some details regarding such a treatment procedure are disclosed in U.S. Pat. No. 7,819,869 to Godara, et al. and U.S. Pat. No. 8,951,249 to Godara, et al., which are incorporated herein by reference. The SI joint 1500 is the joint between the sacrum 1502, a large bone at the base of the spine composed of five fused vertebrae, and the ilium 1504 of the pelvis. The SI joint is a relatively immobile joint, serving to absorb shock during locomotion. The structure of the SI joint and surrounding tissues varies significantly between individuals but generally includes an articular cartilaginous surface, a ligamentous aspect and, in most cases, one or more synovial recesses. Though the specific pathways of SI joint innervation have not yet been elucidated, the nerves responsible for SI pain are thought to include, at least in part, nerves emanating from the dorsal sacral plexus, the network of nerves on the posterior surface of the sacrum, extending from the sacral nerves, also referred to as the posterior primary rami 1506, that exit the sacral foramina 1508 (posterior sacral foramen). The lateral branches 1510 branch out from the sacral nerves (and branch out further along the sacrum as well) and are thought to play a role in the innervation of the SI joint. The surface of the sacrum can be very uneven, inhibiting the ability of a small lesion to affect nerves running along crests of the sacrum, as well as those within the grooves or recesses in the sacral surface; furthermore, accessing the sacrum can require penetrating the sacroiliac ligaments, ligaments responsible for bearing a large proportion of the weight of the body and which, desirably, would be severed or weakened as little as possible.

Due to the anatomy of the sacrum, a straight "gun-barrel" approach, substantially perpendicular to the plane of the sacrum or to the target site, may be desirable. However, if a target nerve to be lesioned is running through a narrow groove or fissure that is too narrow to accommodate a probe capable of creating a lesion with the desired volume, the nerve may remain distal to an inserted probe, even if the probe is in contact with the surface of the sacrum. Embodiments of the device of the present invention may be used according to embodiments of the method described above in order to create a lesion that is primarily located distal to the probe 100. This may allow for a substantially perpendicular "gun-barrel" approach and a lesion thus created may encompass the target nerve.

In some embodiments, it may be desired to treat one or more neural structures within a sacral neural crescent. The term "sacral neural crescent" refers to an area lateral to each of the sacral foramina, through which the sacral nerves are believed to pass after exiting the foramina. On the dorsal right side of the sacrum, this window is from about 12 o'clock to about 6 o'clock in a clockwise direction, while on the dorsal left side of the sacrum the window is from about 6 o'clock to about 12 o'clock in a clockwise direction. Similar (but in the counter-clockwise direction) areas exist on the ventral side of the sacrum. The clock positions are referenced as if the foramen is viewed as a clock face, and the view is taken looking towards the sacrum. For reference, the 12 o'clock position of the clock face would be the most cephalad (towards the head) point of the foramen.

In other embodiments, methods of the present invention may be used to treat other conditions at various regions within the body, which may be external to the patient's spine. Examples of such conditions include, but are not limited to, pain-causing conditions such as Complex Regional Pain Syndrome (CRPS), Trigeminal Neuralgia, Joint Specific Peripheral Neuropathy, Facet Joint Pain, Fibrotic pain or pain due to scar tissue, and Hypogastric or Pelvic Pain. In general, these conditions may be treated by lesioning at least one target nerve that may be associated with a patient's pain in accordance with method embodiments of the present invention. For example, in the case of trigeminal neuralgia, devices and methods of the present invention may be used to form a lesion at the trigeminal nerve. In the case of CRPS, devices and methods of the present invention may be used to form a lesion at a sympathetic nerve chain.

In addition to the treatment of pain-causing conditions, methods and devices of the present invention may be used for other applications, such as cardiac ablation, for example in cases of atrial tachycardia, is removal or treatment of scar tissue, treatment of varicose veins, treatment of hyperparathyroidism, and ablation of malignancies or tumors, for example in the lung, liver, or bone. In general, these conditions may be treated by lesioning at least one target site associated with a symptom or cause of a patient's condition. For example, in the case of atrial tachycardia, devices and methods of the present invention may be used to form a lesion at the His Bundle region of the heart. In the case of hyperparathyroidism, devices and methods of the present invention may be used to form a lesion at one or more parathyroid glands.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An electrosurgical device comprising:
   a probe extending along a longitudinal axis, wherein the probe includes a proximal region and a distal region, wherein an inner diameter of the probe defines a lumen, wherein the probe has an electrically insulated portion extending from the proximal region to the distal region and an electrically exposed conductive portion located at the distal region, wherein the electrically exposed conductive portion delivers radiofrequency energy to an area of tissue adjacent the distal region of the probe; and
   a heat transfer system for removing thermal energy from the area of tissue, wherein the heat transfer system is in thermal contact with the area of tissue, wherein the heat transfer system removes from about 0.1 Watts to about 50 Watts of energy from the area of tissue, the heat transfer system comprising:
      at least two Peltier circuits positioned within the lumen and spaced apart along the longitudinal axis of the probe, each of the at least two Peltier circuits including a hot side formed from a first material and a cold side formed from a second material; and
      a heat sink positioned at a proximal region of the probe and thermally coupled to the plurality of Peltier circuits.

2. The electrosurgical device of claim 1, wherein the heat transfer system removes from about 2 Watts to about 12 Watts of energy from the area of tissue.

3. The electrosurgical device of claim 1, wherein the heat transfer system is at least partially disposed within the lumen.

4. The electrosurgical device of claim 1, the heat transfer system is configured to absorb or remove thermal energy over a time period ranging from about 60 seconds to about 300 seconds.

5. The electrosurgical device of claim 1, wherein the heat transfer system comprises a heat removal material in thermal contact with the area of tissue.

6. The electrosurgical device of claim 5, wherein the heat removal material is disposed within the lumen.

7. The electrosurgical device of claim 5, wherein the heat removal material comprises a heat transfer material, a heat sink, or a combination thereof.

8. The electrosurgical device of claim 7, wherein the heat transfer material comprises a thermally conductive material, one or more additional Peltier circuits, or a combination thereof.

9. The electrosurgical device of claim 7, wherein the heat sink comprises a phase change material.

10. The electrosurgical device of claim 9, wherein the phase change material changes phase at a temperature between about 40° C. and 100° C.

11. The electrosurgical device of claim 9, wherein the phase change material has a heat of fusion ranging from about 150 Joules/gram to about 300 Joules/gram.

12. The electro surgical device of claim 9, wherein from about 1 gram to about 12 grams of the phase change material is required to remove from about 2 Watts to about 12 Watts of energy from the probe over a 150 second time period.

13. The electrosurgical device of claim 12, wherein the phase change material comprises a paraffin wax.

14. The electrosurgical device of claim 9, wherein the phase change material surrounds a conductor extending from the electrically exposed conductive portion of the probe at the distal region of the probe towards a proximal end of the probe.

15. The electro surgical device of claim 7, wherein the heat sink comprises a gas or a pressurized liquid, wherein the gas or the pressurized liquid is contained within the lumen.

16. The electrosurgical device of claim 15, wherein the gas is carbon dioxide or nitrogen and the liquid is liquid carbon dioxide.

17. The electro surgical device of claim 15, wherein the lumen contains an inlet channel, wherein the gas or pressurized liquid is introduced into the lumen, and an outlet channel where the gas or pressurized liquid exits the lumen, wherein the inlet channel and the outlet channel are defined by a separator, wherein the inlet channel has a diameter that is smaller than a diameter of the outlet channel.

18. The electrosurgical device of claim 7, wherein the heat sink comprises an endothermic reaction system, wherein the endothermic reaction system comprises a first material separated from a second material, wherein an endothermic reaction occurs when the first material contacts the second material.

19. The electro surgical device of claim 18, wherein the first material comprises water and the second material comprises ammonium nitrate.

20. The electro surgical device of claim 19, wherein the first material and the second material are stored in a cartridge that is inserted into the lumen prior to use of the electrosurgical device.

21. The electro surgical device of claim 18, wherein the heat transfer system further comprises a wire, wherein the wire facilitates the transfer of heat from the electrically exposed conductive portion of the probe to the endothermic reaction between the first material and the second material.

22. The electrosurgical device of claim 7, wherein the heat removal material includes the heat transfer material and the heat sink, wherein the heat transfer material is in thermal communication with the heat sink.

23. The electrosurgical device of claim 22, wherein the heat sink is an external heat sink.

24. The electrosurgical device of claim 22, wherein the heat transfer material is in communication with the heat sink via one or more conductive wires or conduits.

25. The electrosurgical device of claim 7, wherein the heat sink comprises a series of fins, etchings, particulates, or a combination thereof.

26. The electrosurgical device of claim 1, wherein a connection exists between the at least two Peltier circuits and the distal region of the probe.

27. The electrosurgical device of claim 26, wherein the hot side of each of the at least two Peltier circuits faces the proximal region of the probe and wherein the cold side of each of the at least two Peltier circuits faces the distal region of the probe.

28. The electrosurgical device of claim 1, wherein the area of tissue adjacent the distal region of the probe is maintained at a temperature of less than about 90° C.

29. The electrosurgical device of claim 1, wherein the heat transfer system is free of a circulating liquid.

30. The electrosurgical device of claim 1, wherein the heat transfer system is free of a pump.

* * * * *